United States Patent [19]

Sato et al.

[11] Patent Number: 5,380,461
[45] Date of Patent: Jan. 10, 1995

[54] TRANS-DIHALOGENOSTILBENE COMPOUNDS AND LIQUID CRYSTAL ELECTRO-OPTICAL DEVICES USING THEM

[75] Inventors: Kikumasa Sato; Seiichi Inoue, both of Yokohama; Jun Ishihara, Tokyo; Katsutoshi Machida, Kanagawa, all of Japan

[73] Assignee: Seimi Chemical Co., Ltd., Chigasaki, Japan

[21] Appl. No.: 767,803

[22] Filed: Sep. 30, 1991

Related U.S. Application Data

[63] Continuation-in-part of Ser. No. 649,061, Feb. 1, 1991, abandoned.

[30] Foreign Application Priority Data

Apr. 13, 1990 [JP] Japan .................................. 2-96259

[51] Int. Cl.$^6$ ...................... C09K 19/34; C09K 19/06; C09K 19/30; C09K 19/12
[52] U.S. Cl. ................ 252/299.61; 252/299.5; 252/299.6; 252/299.63; 252/299.64; 252/299.66; 252/299.67
[58] Field of Search ............. 252/299.01, 299.5, 299.6, 252/299.61, 299.63, 299.66, 299.64, 299.67

[56] References Cited

U.S. PATENT DOCUMENTS

3,767,289 10/1973 Aviram et al. ................... 252/299.6

FOREIGN PATENT DOCUMENTS

341037 2/1991 Japan .

OTHER PUBLICATIONS

Kremlev, Zhurnal Org. Khim. pp. 279–283, (1981).

*Primary Examiner*—Philip Tucker
*Attorney, Agent, or Firm*—Oblon, Spivak, McClelland, Maier & Neustadt

[57] ABSTRACT

A trans-dihalogenostilbene compound of the formula:

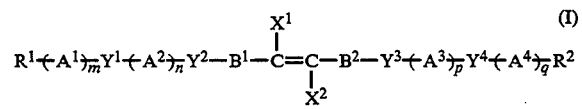

wherein each of $A^1$ to $A^4$, which are independent from one another, is a trans-1,4-cyclohexylene group or a 1,4-phenylene group, which is unsubstituted or substituted by one or more halogen atoms, methyl groups or nitrile groups and in which one or more CH groups may be substituted by nitrogen atoms, and one or more $CH_2$ groups may be substituted by oxygen atoms or sulfur atoms; each of $B^1$ and $B^2$, which are independent from each other, is a 1,4-phenylene group, which is unsubstituted or substituted by one or more halogen atoms, methyl groups or nitrile groups and in which one or more CH groups may be substituted by nitrogen atoms; each of $Y^1$ to $Y^4$, which are independent from one another, is —COO—, —O—, —OCO—, —$CH_2CH_2$—, —$CH_2$—, —CH=CH—, —$OCH_2$—, —$CH_2O$—, —CH=N—, —NO=N—, —N=ON—, —C≡C—, —N=N— or a single bond; each of $X^1$ and $X^2$, which are independent from each other, is a fluorine atom, a chlorine atom, a bromine atom or a trifluoromethyl group; each of m, n, p and q is 0 or 1; and each of $R^1$ and $R^2$, which are independent from each other, is a $C_1$–$C_{10}$ alkyl group, a halogen atom, a nitrile group or an isothiacyanate group, provided that in the case of the alkyl group, an oxygen atom may be interposed in a carbon-carbon bond of the group or in a carbon-carbon bond between this group and the adjacent ring, and in a case where $R^1$ or $R^2$ is the alkyl group, some of hydrogen atoms in the group may be substituted by fluorine atoms.

18 Claims, 8 Drawing Sheets

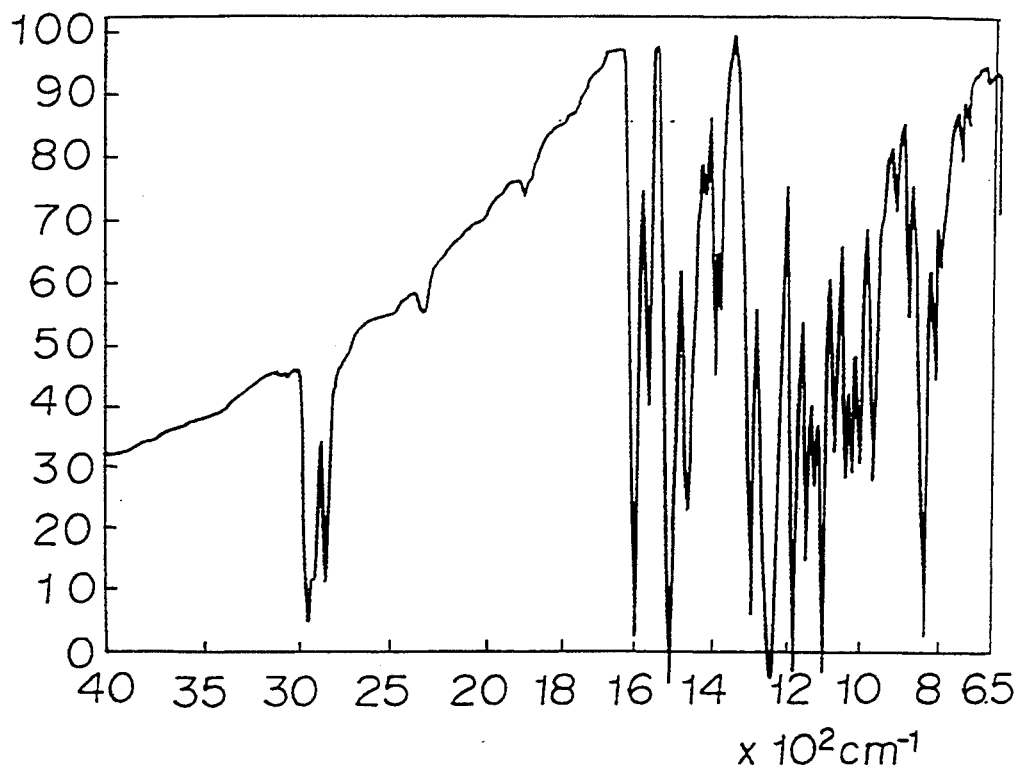
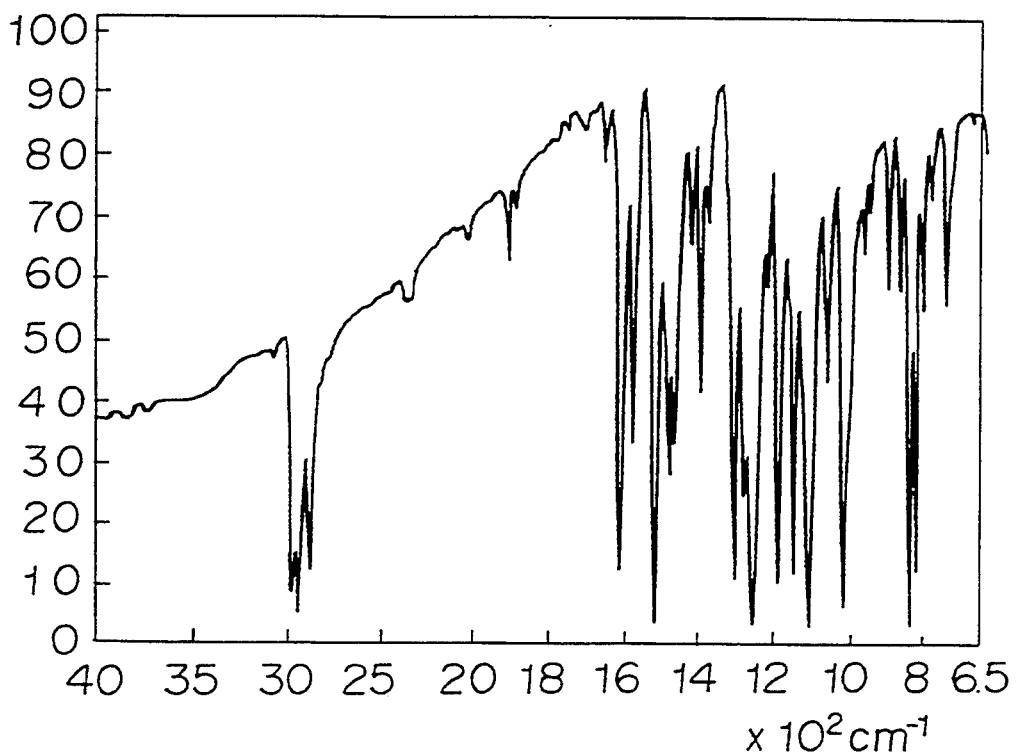

TRANS-DIHALOGENOSTILBENE COMPOUNDS AND LIQUID CRYSTAL ELECTRO-OPTICAL DEVICES USING THEM

This application is a continuation-in-part application of the application Ser. No. 07/649,061 having a filing date of Feb. 1, 1991 now abandoned.

BACKGROUND OF THE INVENTION

1. Field of the Invention

The present invention relates to trans-dihalogenostilbene compounds useful for liquid crystal electro-optical devices, liquid-crystal compositions containing them and liquid crystal electro-optical devices using them.

2. Discussion of Background

Liquid crystal display devices have been used for watches and electronic calculators and in recent years for various applications including measuring devices, automobile meters, copying machines and cameras. Accordingly, various functions including a wide temperature range for operation, a low voltage for driving, a quick response and chemical stability, are required for such liquid display devices.

However, at present, there is no single material which by itself satisfies all of such requirements, and it is a common practice to satisfy such requirements by a liquid crystal composition prepared by mixing a plurality of liquid crystals and non-liquid crystal materials. Accordingly, it is desired to develop a liquid crystal material or a non-liquid crystal material which is excellent in one or more functions, if not in all the required functions.

For a twisted nematic (TN) type liquid crystal cell in the field of display devices using liquid crystal, in order to prevent formation of an interference fringe on the cell surface which causes deterioration of the outer appearance of the liquid crystal cell, it is necessary to set a certain specific value for the product of the anisotropy of refractive index ($\Delta n$) of the liquid crystal material filled in the cell and the thickness (d) of the cell. Since the value of $\Delta n d$ is set at a certain specific level, it is possible to minimize the value d by using a material having a large value $\Delta n$. If the value of d is minimized, the response time ($\tau$) can be minimized in accordance with a well known formula of $\tau \alpha d^2$.

Thus, a liquid crystal material having a large value of $\Delta n$ is a very important material useful for the preparation of a liquid crystal cell having a high response speed and yet free from an interference fringe.

On the other hand, practically feasible liquid crystal material is in many cases prepared by mixing several or more components comprising compounds having a nematic phase around room temperature and compounds having a nematic phase in a temperature range higher than room temperature, and is usually used in the form of a liquid crystal composition.

Further, it is known that the response time is positively interrelated with the viscosity of the liquid crystal material.

Accordingly, it is an important object to provide a material which has a large value of $\Delta n$, small viscosity and excellent compatibility with other liquid crystal materials or non-liquid crystal materials and which is chemically stable.

SUMMARY OF THE INVENTION

It is an object of the present invention to provide a novel material which is capable of solving the above-mentioned problems.

The present invention provides a trans-dihalogenostilbene compound of the formula:

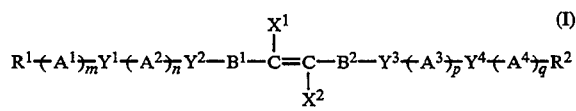

wherein each of $A^1$ to $A^4$, which are independent from one another, is a trans-1,4-cyclohexylene group or a 1,4-phenylene group, which is unsubstituted or substituted by one or more halogen atoms, methyl groups or nitrile groups and in which one or more CH groups may be substituted by nitrogen atoms, and one or more $CH_2$ groups may be substituted by oxygen atoms or sulfur atoms; each of $B^1$ and $B^2$, which are independent from each other, is a 1,4-phenylene group, which is unsubstituted or substituted by one or more halogen atoms, methyl groups or nitrile groups and in which one or more CH groups may be substituted by nitrogen atoms; each of $Y^1$ to $Y^4$, which are independent from one another, is —COO—, —O—, —OCO—, —$CH_2CH_2$—, —$CH_2$—, —CH=CH—, —$OCH_2$—, —$CH_2O$—, —CH=N—, —NO=N—, —N=ON—, —C≡C—, —N=N— or a single bond; each of $X^1$ and $X^2$, which are independent from each other, is a fluorine atom, a chlorine atom, a bromine atom or a trifluoromethyl group; each of m, n, p and q is 0 or 1; and each of $R^1$ and $R^2$, which are independent from each other, is a $C_1$–$C_{10}$ alkyl group, a halogen atom, a nitrile group or an isothiacyanate group, provided that in the case of the alkyl group, an oxygen atom may be interposed in a carbon-carbon bond of the group or in a carbon-carbon bond between this group and the adjacent ring, and in a case where $R^1$ or $R^2$ is the alkyl group, some of hydrogen atoms in the group may be substituted by fluorine atoms.

The present invention also provides a liquid crystal composition containing at least one of such compounds of the formula (I) and a liquid crystal electro-optical device having such a liquid crystal composition interposed between a pair of substrates.

BRIEF DESCRIPTION OF THE DRAWINGS

FIGS. 1 to 15 are graphs showing the infrared (IR) spectra of the compounds of the Examples of the present invention.

DETAILED DESCRIPTION OF THE PREFERRED EMBODIMENTS

Figure 1:
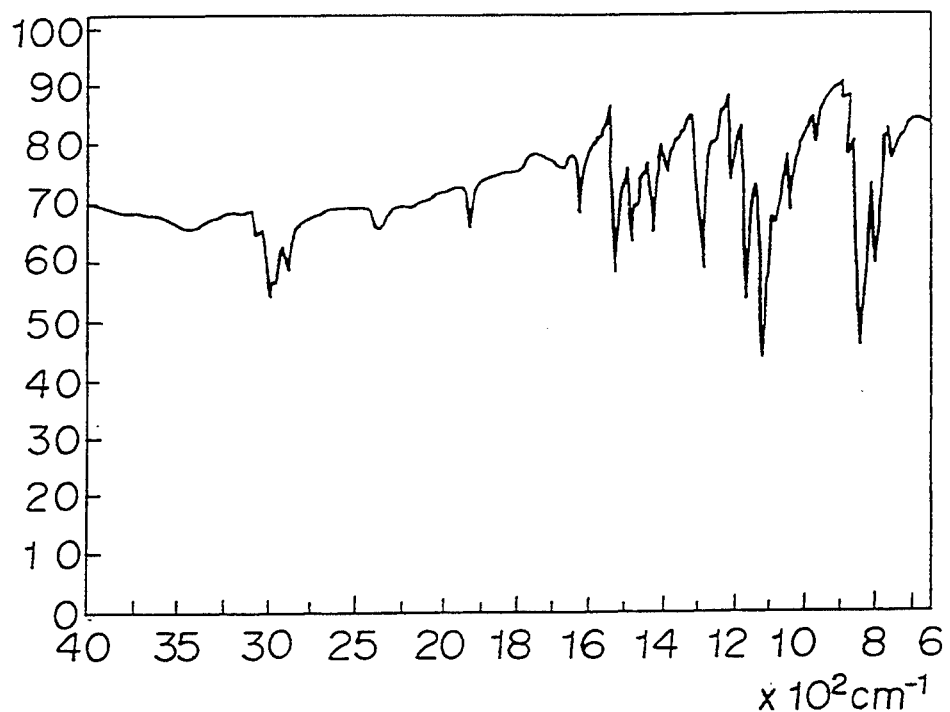

The compounds of the formula (I) of the present invention are novel materials having large values of $\Delta n$, and when mixed with other liquid crystal materials or non-liquid crystal materials to form liquid crystal compositions, the compounds of the formula (I) serve to increase $\Delta n$ of such liquid crystal compositions. They have low viscosity and are chemically stable materials excellent in the compatibility with other liquid crystal materials or non-liquid crystal materials.

The compounds of the formula (I) of the present invention are useful for liquid crystal compositions. A liquid crystal composition may be prepared by mixing at least one of them with other liquid materials or non-liquid materials.

The substances which may be mixed with the compounds of the present invention, include, for example, the following compounds. In the following formulas, each of R and R' represents a group such as an alkyl group, an alkoxy group, a halogen atom or a cyano group, as is different from R in the formula (I) of the present invention.

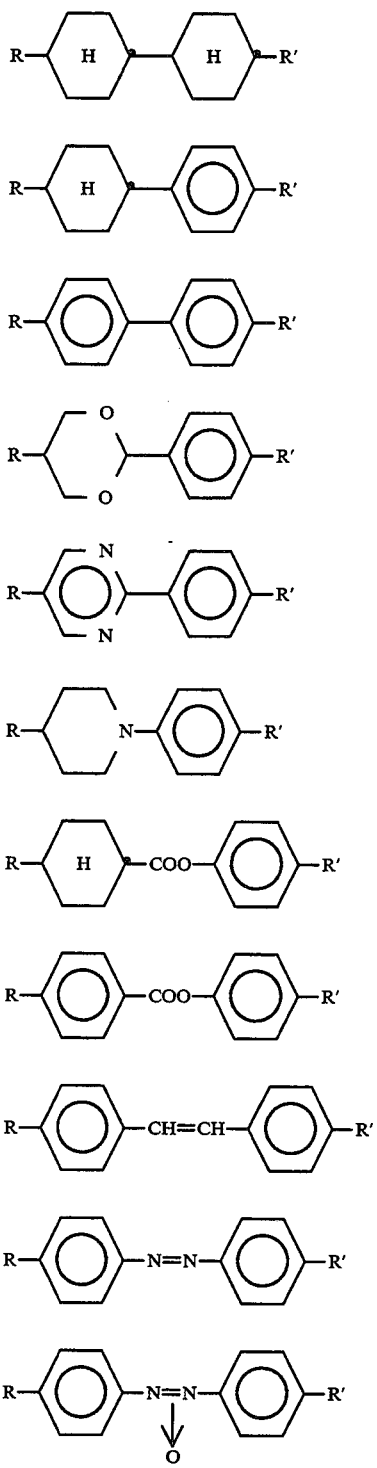

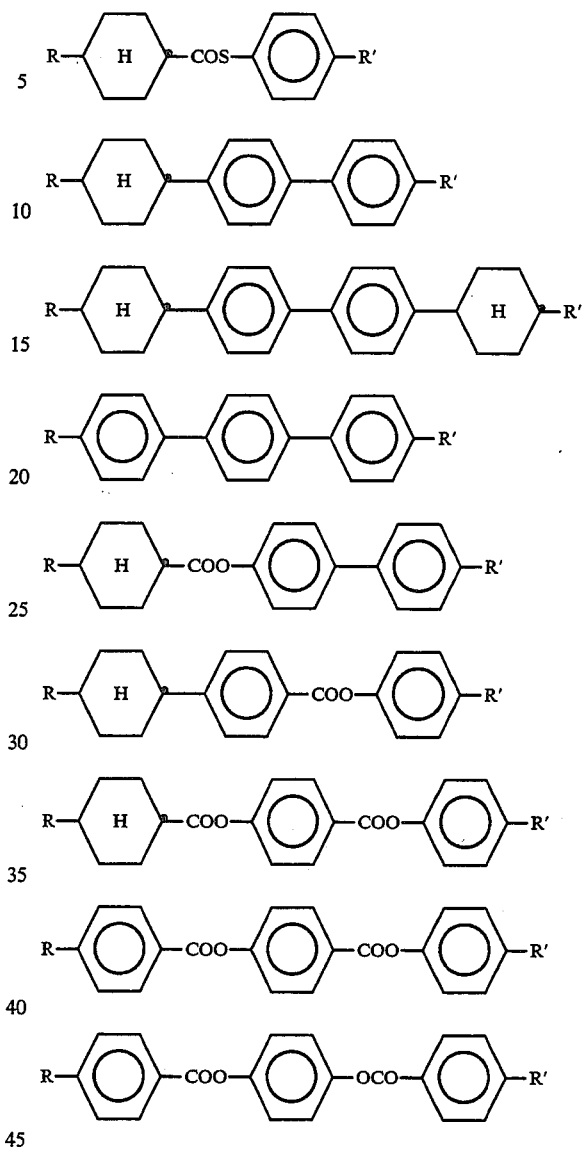

These compounds are presented merely as examples, and various materials may be selected for use including those modified by replacing a hydrogen atom with a halogen atom, a cyano group or a methyl group, by changing a cyclohexane ring or a benzene ring to other six-membered ring or a five-membered ring, or by changing the linking group between the rings.

The liquid crystal composition of the present invention is used by injecting it into a liquid crystal cell.

As a typical liquid crystal cell, a twisted nematic (TN) liquid crystal device may be mentioned, which is prepared by forming a transparent electrode of e.g. $In_2O_3$—$SnO_2$ in a desired pattern on an inner surface of a transparent substrate of e.g. glass or plastic, applying an overcoat of e.g. $SiO_2$ or polyimide, as the case requires, disposing a pair of such substrates having horizontally oriented layers to face each other, sealing the periphery of the substrates, injecting a liquid crystal and then sealing the injection inlet, and a polarizing plate is laminated on each side of the cell for use. Other than this, a super twisted nematic (STN) type having a large twist angle which has attracted an attention in recent years, a phase transfer type, a guest-host type, a dynamic scattering type or a combination thereof may be employed. Further, the liquid crystal composition of the present invention may also be employed for a liquid crystal cell of a type whereby writing is conducted not electrically but thermally.

Further, with respect to the cell structure, various types are applicable including those wherein an undercoating layer of e.g. $SiO_2$ or $Al_2O_3$ is provided between the transparent substrate and the transparent electrode, wherein a reflective electrode is employed, wherein a double-layer electrode is employed, wherein a colored polarizing plate is employed, wherein a color filter is employed, wherein a semiconductor substrate is employed, and wherein the cell is constructed as a double-layer device. Thus, such cells are useful for various applications including watches, electronic calculators, measuring devices, various meters for automobiles, games and computer terminals.

The compound of the formula (I) of the present invention can be produced, for example, by the following process. In the following formulas, $R^1$, $R^2$, $A^1$ to $A^4$, $Y^1$ to $Y^4$, $B^1$, $B^2$, $X^1$, $X^2$, m, n, p and q are as defined above with respect to the formula (I), and each of $X^3$ and $X^5$ represents a halogen atom.

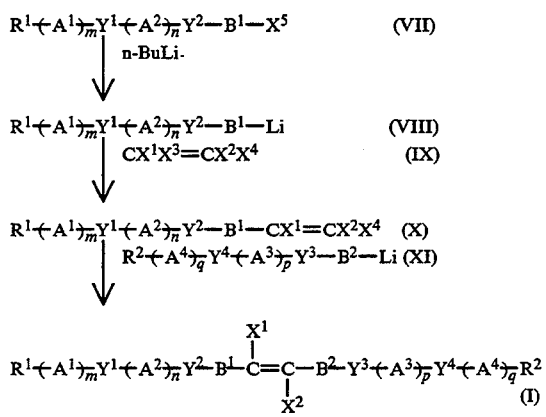

Namely, a halide such as an iodide of the formula (VII) is converted to a lithium compound (VIII) by means of n-butyl lithium. The obtained compound (VIII) and a tetrahalogenoethylene of the formula (IX) are reacted at $-80°$ C. to obtain a compound of the formula (X). The compound of the formula (X) is reacted with a lithium compound of the formula (XI) obtained in the same manner as the compound (VIII), to obtain a trans-dihalogenostilbene compound of the formula (I).

In the present invention, the compound of the following formula (II) is particularly preferred, since it has a low viscosity and excellent properties. This compound of the formula (II) can be prepared, for example, by the following process in the same manner as the compound of the formula (I). In the following formulas, $R^1$, $R^2$, $X^1$, $X^2$, $Z^1$ and $Z^2$ are as defined above with respect to the formula (II), and each of $X^3$ to $X^5$ is a halogen atom.

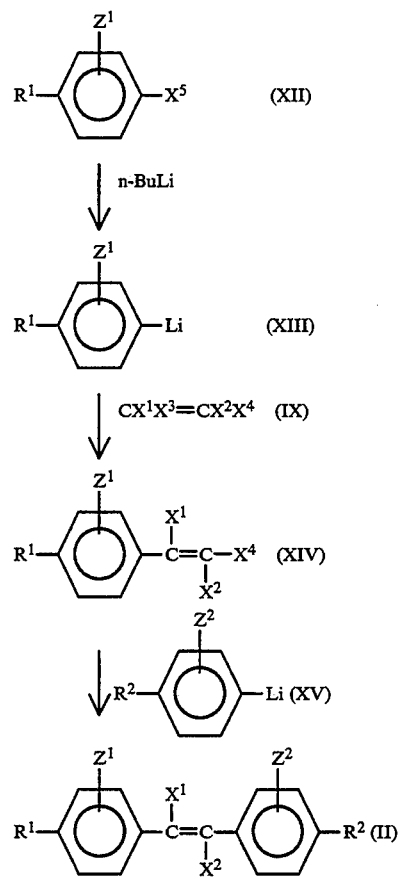

Further, the compound of the formula (I) of the present invention wherein $R^1$ or $R^2$ is a nitrile group or a nitrile group is introduced in $A^1$-$A^4$, $B^1$ or $B^2$ may be produced, for example, by reacting with CuCN the compound of the formula (I) of the present invention wherein a position to which the nitrile group is introduced, is bromine or iodine.

Furthermore, the compound of the formula (I) of the present invention wherein $Y^1$-$Y^4$ is —COO— or —OCO— may be produced, for example, by preparing the compound of the formula (I) wherein $R^1$ or $R^2$ is a hydroxyl group and then reacting an acid chloride thereto.

These processes are given merely as examples, and various other processes may be employed.

In the present invention, when each of $R^1$ and $R^2$ is an alkyl group, some of hydrogen atoms in such an alkyl group may be substituted by fluorine atoms, whereby it is possible to increase $\Delta\epsilon$ and thereby to improve the response speed during multiplex drive. Further, as mentioned above, this alkyl group may have an oxygen atom interposed in a carbon-carbon bond in the group or in a carbon-carbon bond between the group and the adjacent ring.

The compound of the present invention and the liquid crystal composition using it has a low viscosity as mentioned above, and is expected to provide a high speed response during multiplex drive without imparing other properties. Therefore, it is suitable for use in STNLCD wherein a layer of a liquid crystal composition is disposed in a fashion twisted at an angle of from 180° to 360° between a pair of substrates.

Typical and specific structures of the compounds of the present invention are as follows. In the following formulas, $Z^1$, $Z^2$, $R^1$, $R^2$, $X^1$ and $X^2$ are as defined above with respect to the formula (I) or (II), and each of $Z^3$ and $Z^4$, which are independent from each other, is a fluorine atom, a chlorine atom or a hydrogen atom, and $X^6$ is a fluorine atom or a chlorine atom.

(1)
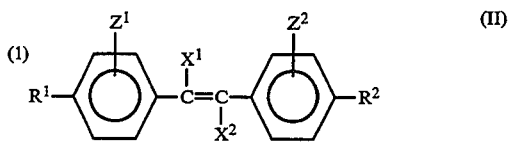
(II)

This compound is the most basic compound and has a low viscosity. This may be further specified as follows:

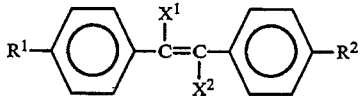
(IIA)

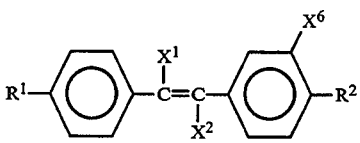
(IIB)

Further, when it is desired to improve the properties at a high temperature by increasing the clearing point over the compound of the formula (II), the following compounds may preferably be employed. Further, since they have a characteristic of low viscosity, such compounds having three or more rings, may be used taking the compatibility with other liquid crystals and other properties into consideration.

(2)
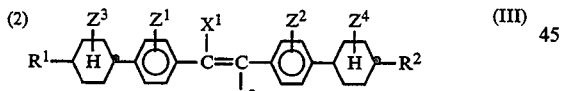
(III)

This compound may be further specified as follows:

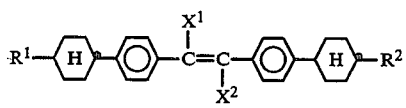
(IIIA)

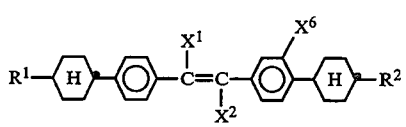
(IIIB)

(3)
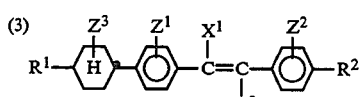
(IV)

This compound may be further specified as follows.

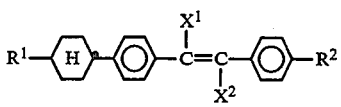
(IVA)

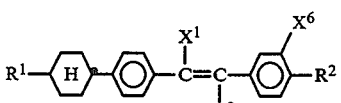
(IVB)

(4)
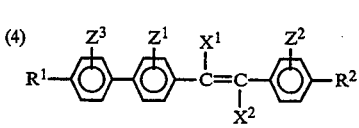
(V)

This compound may be further specified as follows.

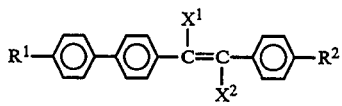
(VA)

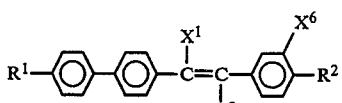
(VB)

(5)
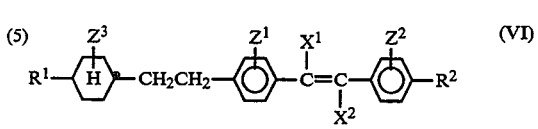
(VI)

This compound may be further specified as follows.

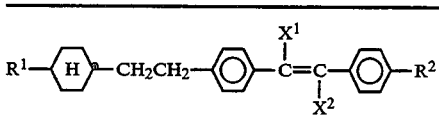
(VIA)

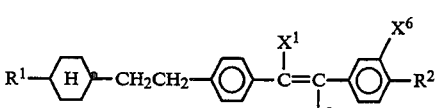
(VIB)

(6)
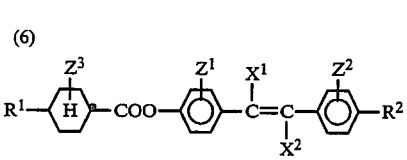
(XVI)

(7)
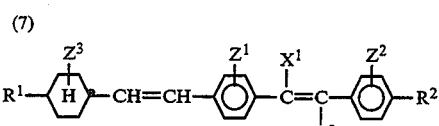
(XVII)

(8)
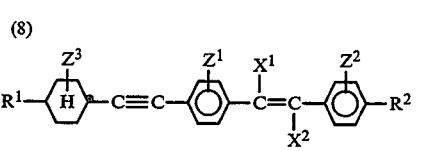
(XVIII)

(9)

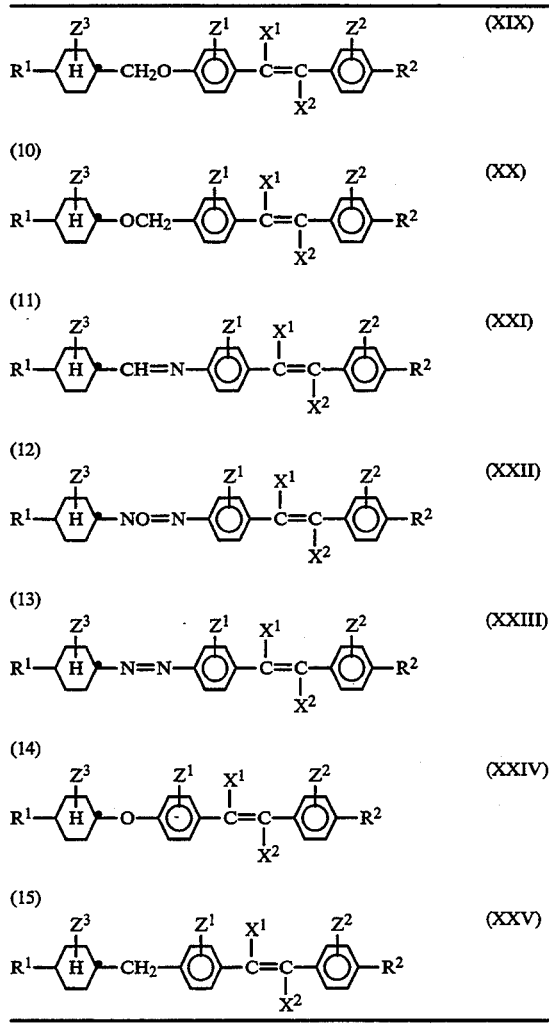

The compound of the formula (I) of the present invention is preferably such that at least one of $R^1$ and $R^2$ is a $C_1$-$C_{10}$ alkyl group, provided that an oxygen atom may be interposed between a carbon-carbon bond of the alkyl group or in a carbon-carbon bond between this group and the adjacent phenylene group. Further, a linear group is usually preferred. However, in a case where it is desired to impart a chiral nature, it may be a branched group. Specifically, an alkyl group, an alkoxy group and an alkoxyalkyl group may be mentioned. Further, when $R^1$ and $R^2$ are other than these groups, it is convenient to use a compound wherein $R^1$ or $R^2$ are cyano groups.

By the substitution some of hydrogen atoms of an alkyl group in such a broad sense by fluorine atoms, anisotropy of dielectric constant ($\Delta\epsilon$) tends to increase.

When incorporated to a liquid crystal composition, the compound of the present invention is effective for improving the response speed and thus us suitable for use in a liquid crystal electro-optical display device operated by multiplex drive. Its effects are remarkable particularly when used in a liquid crystal electro-optical display device to be operated under a high duty drive at a level of 1/200 or 1/400 (scanning electrode number of 200 or 400).

Thus, its effects are substantial when it is applied to STNLCD. Namely, as a liquid crystal composition, a liquid crystal composition having a chiral compound to impart natural twist to liquid crystal or a cholesteric liquid crystal incorporated, is employed. Such a liquid crystal composition is used for a liquid crystal electro-optical display device wherein a pair of electrodes on the substrates or coating layers on such electrodes are treated by rubbing treatment so that liquid crystal molecules are twisted at an angle of from 180° to 360°.

As a coating layer on such an electrode, a coating layer of e.g. an inorganic material such as $SiO_2$ or $Al_2O_3$, a polyimide, a polyamide or a silicon resin, may be used as mentioned above. Polyimide is preferred since the alignment of liquid crystals is thereby excellent.

Now, the present invention will be described in further detail with reference to Examples. However, it should be understood that the present invention is by no means restricted by such specific Examples.

In the following Examples, "m.p." means "melting point", and "c.p." means "clearing point".

EXAMPLE 1

Air in a dried four-necked flask was replaced with nitrogen, and 10 ml of n-hexane and 2.86 g (0.0116 mol) of p-n-propyliodobenzene were introduced. Then, 10 ml of a hexane solution of n-butyl lithium (0.0116 mol) was gradually added thereto under stirring to obtain a hexane solution of n-propylphenyl lithium.

On the other hand, the same operation was conducted using another dried four-necked flask to obtain a hexane solution of n-propylphenyl lithium.

Into one of the four-necked flasks for the n-propylphenyl lithium hexane solutions, 2.5 ml of diethyl ether was added, and the mixture was cooled to −80° C. Then, the system was vacuumed, and 1.4 g (0.014 mol) of tetrafluoroethylene gas was introduced from a gas buret. Then, the interior of the system was returned to atmospheric pressure with nitrogen gas, and the mixture was reacted at −80° C. for one hour. Then, the reaction mixture was returned to room temperature and unreacted tetrafluoroethylene gas was purged with nitrogen gas. Then, the interior of the system was cooled to −80° C., and the other n-propylphenyl lithium hexane solution was gradually dropwise added thereto. After completion of the dropwise addition, the mixture was reacted at −80° C. for one hour. The reaction mixture was returned to room temperature and poured into ice water and neutralized with dilute hydrochloric acid, and then the organic layer was separated. The aqueous layer was extracted with ethyl ether, and the extract was combined to the organic layer. The combined organic layer was dried over anhydrous magnesium sulfate. The solvent was distilled off, and the residue was purified by silica gel column chromatography to obtain 0.5 g of the following desired compound (trans-4,4'-bis-(n-propyl)difluorostilbene). m.p.: 74.6° C., c.p.: 83.8° C.

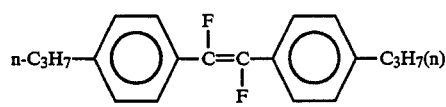

$^1$H NMR ($CDCl_3$ solvent, TMS internal standard) $\delta$(ppm) 0.95 (t,—$CH_3$, 6H) 1.67 (m,—$CH_2CH_3$, 4H) 2.62 (t,$CH_2CH_2CH_3$, 4H) 7.33 (d,d,aromatic,8H)

Further, the IR spectrum (KBr tablet) of this compound is shown in FIG. 1.

EXAMPLE 2

In 1 l four-necked flask having a gas supplying tube, 200 ml of n-hexane, 75 ml of dry diethyl ether and 24.6 g (0.1 mol) of 4-(n-propyl)iodobenzene were introduced under a nitrogen atmosphere, and then 86.2 ml of a hexane solution of n-butyl lithium (1.16 mol) was dropwise added thereto under stirring at −80° C. Then, while the reaction system was maintained at −80° C., 10 g (0.1 mol) of tetrafluoroethylene was introduced under vigorously stirring in 30 minutes. The reaction solution was stirred further for one hour and poured into ice water and neutralized with dilute hydrochloric acid, and then the organic layer was separated. The aqueous layer was extracted with methylene chloride, and the extract was combined to the organic layer, followed by drying. The solvent was distilled off to obtain 12 g (yield: 60%) of 1-(4-n-propylphenyl)-1,2,2-trifluoroethylene.

On the other hand, in 500 ml of four-necked flask, 100 ml of n-hexane, 40 ml of dry diethyl ether and 17.0 g (0.06 mol) of 4-iodobromobenzene were introduced under a nitrogen atmosphere, and 51.7 ml of a hexane solution of n-butyl lithium (1.16 mol) was dropwise added thereto under stirring at −80° C. The reaction solution was stirred further for one hour and then dropwise added to a dry diethyl ether solution of 1-(4-n-propylphenyl)-1,2,2-trifluoroethylene (12 g) prepared above at −80° C. The reaction solution was stirred at room temperature further for one hour. The reaction solution was poured into ice water and neutralized with dilute hydrochloric acid, and then the organic layer was separated. The aqueous layer was extracted with methylene chloride, and the extract was combined to the organic layer, followed by drying. The solvent was distilled off to obtain 15.2 g (yield: 75%) of trans-(4-bromo-4'-n-propyl)difluorostilbene.

Then, 4.03 g (0.045 mol) of CuCN was dissolved in 30 ml of anhydrous dimethyl sulfoxide (DMSO) by heating to 90° C. Then a DMSO solution of trans-(4-bromo-4'-n-propyl) difluorostilbene (15.2 g, 0.045 mol) prepared above was dropwise added thereto under stirring. The reaction solution was stirred at 150° C. for one hour and cooled to room temperature. 100 ml of water was poured thereto and the reaction mixture was extracted with methylene chloride. The organic layer was washed with a saturated sodium chloride aqueous solution and dried over $CaCl_2$, followed by filtration. The solvent was distilled off, and the solid thus obtained was purified by silica gel column chromatography to obtain 11.5 g (yield: 90%) of trans-(4-cyano-4'-n-propyl)difluorostilbene.

The analytical results of the compound are as follows:
$^{19}F$ NMR (($CD_3)_2CO$) −145.7 ppm (d, 119.4 Hz) −156.5 ppm (d, 119.4 Hz) MS (mass spectrum) m/e 283 (M+) IR (infrared spectrum) 2228 $cm^{-1}$ (C≡N)

In the following formulas, Ph means a phenylene group

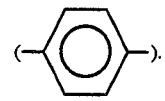

n-C$_3$H$_7$—Ph—CF=CF—Ph—CN
Trans-4-propyl-4'-cyano-α,α'-difluorostilbene

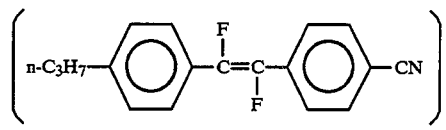

Figure 2:
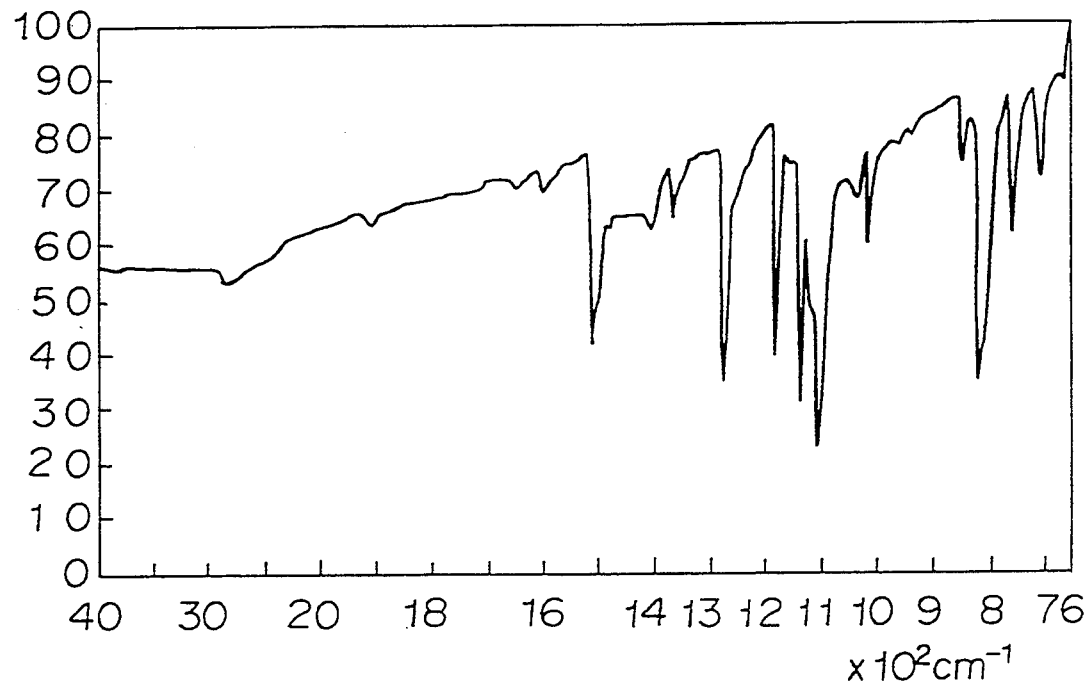

CH$_3$—Ph—CF=CF—Ph—CN
n-C$_4$H$_9$—Ph—CF=CF—Ph—CN
n-C$_6$H$_{13}$—Ph—CF=CF—Ph—CN
n-C$_8$H$_{17}$—Ph—CF=CF—Ph—CN
n-C$_{10}$H$_{21}$—Ph—CF=CF—Ph—CN
CH$_3$—Ph—CF=CF—Ph—CH$_3$ (m.p. 109.3° C., c.p. 111.9° C., IR spectrum: shown in FIG. 2)

Figure 3:
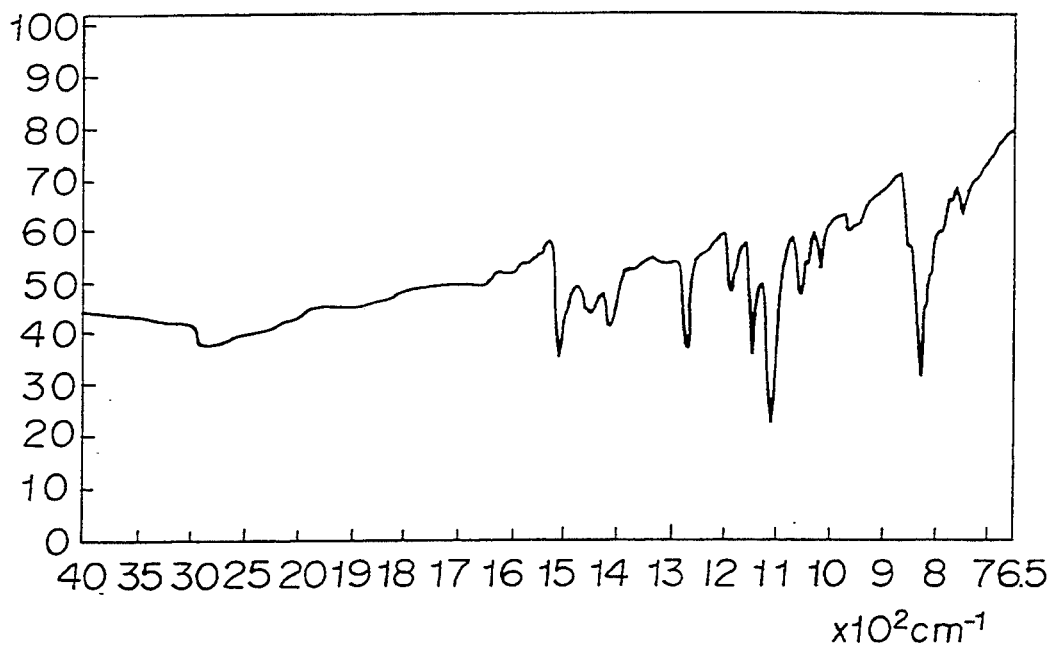

CH$_3$—Ph—CF=CF—Ph—C$_2$H$_5$
CH$_3$—Ph—CF=CF—Ph—C$_4$H$_9$(n)
CH$_3$—Ph—CF=CF—Ph—C$_6$H$_{13}$(n)
CH$_3$—Ph—CF=CF—Ph—C$_8$H$_{17}$(n)
CH$_3$—Ph—CF=CF—Ph—C$_{10}$H$_{21}$(n)
C$_2$H$_5$—Ph—CF=CF—Ph—C$_2$H$_5$ (m.p. 39.3° C., c.p. 41.3° C., IR spectrum: shown in FIG. 3)

C$_2$H$_5$—Ph—CF=CF—Ph—C$_3$H$_7$(n)
C$_2$H$_5$—Ph—CF=CF—Ph—C$_5$H$_{11}$(n)
C$_2$H$_5$—Ph—CF=CF—Ph—C$_7$H$_{15}$(n)
C$_2$H$_5$—Ph—CF=CF—Ph—C$_9$H$_{19}$(n)
n-C$_3$H$_7$—Ph—CF=CF—Ph—C$_4$H$_9$(n)
n-C$_3$H$_7$—Ph—CF=CF—Ph—C$_6$H$_{13}$(n)
n-C$_3$H$_7$—Ph—CF=CF—Ph—C$_8$H$_{17}$(n)
n-C$_3$H$_7$—Ph—CF=CF—Ph—C$_{10}$H$_{21}$(n)
n-C$_4$H$_9$—Ph—CF=CF—Ph—C$_4$H$_9$(n)

Figure 4:
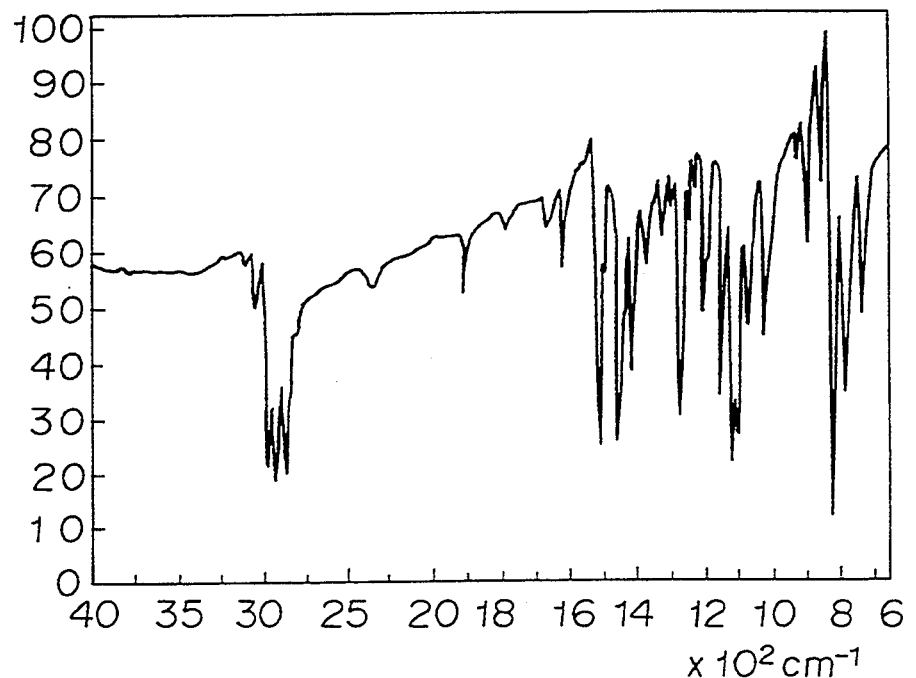

(m.p. 47.1° C., c.p. 57.8° C., IR spectrum: shown in FIG. 4)

n-C$_4$H$_9$—Ph—CF=CF—Ph—C$_5$H$_{11}$(n)
n-C$_4$H$_9$—Ph—CF=CF—Ph—C$_7$H$_{15}$(n)
n-C$_4$H$_9$—Ph—CF=CF—Ph—C$_9$H$_{19}$(n)
n-C$_5$H$_{11}$—Ph—CF=CF—Ph—C$_5$H$_{11}$(n)

C$_2$H$_5$—Ph—CF=CF—Ph—CN
n-C$_5$H$_{11}$—Ph—CF=CF—Ph—CN
n-C$_7$H$_{15}$—Ph—CF=CF—Ph—CN
n-C$_9$H$_{19}$—Ph—CF=CF—Ph—CN

CH$_3$—Ph—CF=CF—Ph—C$_3$H$_7$(n)
CH$_3$—Ph—CF=CF—Ph—C$_5$H$_{11}$(n)
CH$_3$—Ph—CF=CF—Ph—C$_7$H$_{15}$(n)
CH$_3$—Ph—CF=CF—Ph—C$_9$H$_{19}$(n)

C$_2$H$_5$—Ph—CF=CF—Ph—C$_4$H$_9$(n)
C$_2$H$_5$—Ph—CF=CF—Ph—C$_6$H$_{13}$(n)
C$_2$H$_5$—Ph—CF=CF—Ph—C$_8$H$_{17}$(n)
C$_2$H$_5$—Ph—CF=CF—Ph—C$_{10}$H$_{21}$(n)
n-C$_3$H$_7$—Ph—CF=CF—Ph—C$_5$H$_{11}$(n)
n-C$_3$H$_7$—Ph—CF=CF—Ph—C$_7$H$_{15}$(n)
n-C$_3$H$_7$—Ph—CF=CF—Ph—C$_9$H$_{19}$(n)

n-C$_4$H$_9$—Ph—CF=CF—Ph—C$_6$H$_{13}$(n)
n-C$_4$H$_9$—Ph—CF=CF—Ph—C$_8$H$_{17}$(n)
n-C$_4$H$_9$—Ph—CF=CF—Ph—C$_{10}$H$_{21}$(n)

Figure 5:
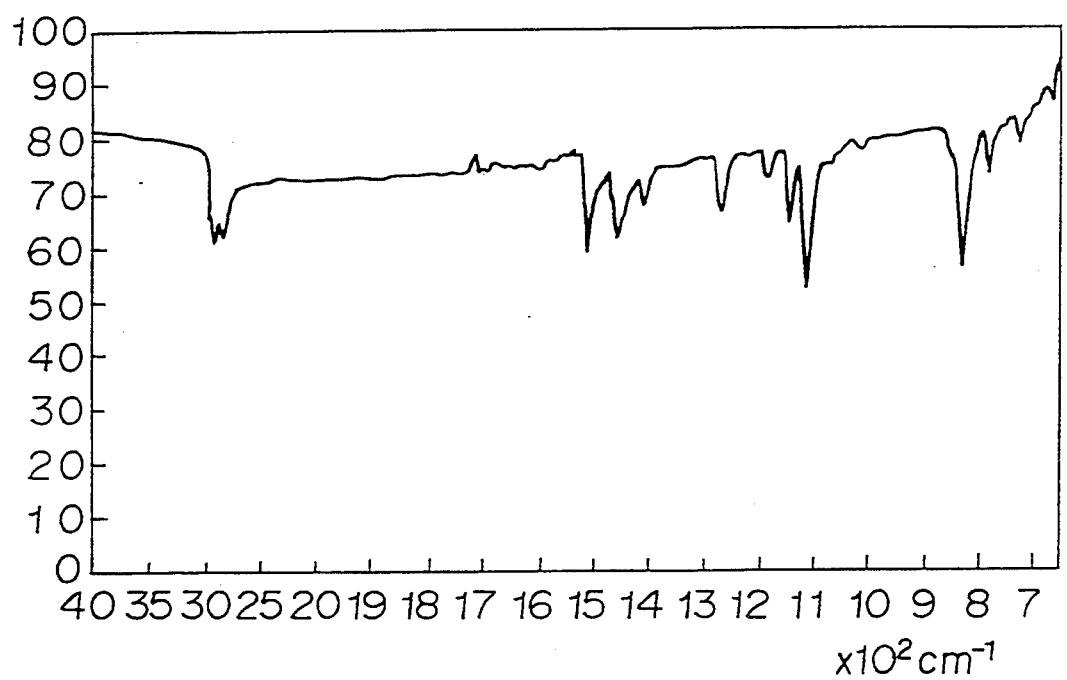

(m.p. 32.1° C., c.p. 86.1° C., IR spectrum: shown in FIG. 5)

n-$C_5H_{11}$—Ph—CF=CF—Ph—$C_6H_{13}$(n)
n-$C_5H_{11}$—Ph—CF=CF—Ph—$C_8H_{17}$(n)
n-$C_5H_{11}$—Ph—CF=CF—Ph—$C_{10}H_{21}$(n)
n-$C_6H_{13}$—Ph—CF=CF—Ph—$C_6H_{13}$(n)
n-$C_6H_{13}$—Ph—CF=CF—Ph—$C_8H_{17}$(n)
n-$C_6H_{13}$—Ph—CF=CF—Ph—$C_{10}H_{21}$(n)
n-$C_7H_{15}$—Ph—CF=CF—Ph—$C_7H_{151}$(n)
n-$C_7H_{15}$—Ph—CF=CF—Ph—$C_9H_{19}$(n)
n-$C_8H_{17}$—Ph—CF=CF—Ph—$C_8H_{17}$(n)
n-$C_8H_{17}$—Ph—CF=CF—Ph—$C_{10}H_{21}$(n)
n-$C_9H_{19}$—Ph—CF=CF—Ph—$C_9H_{19}$(n)
n-$C_{10}H_{21}$—Ph—CF=CF—Ph—$C_{10}H_{21}$(n)

-continued

The following compounds can be prepared by changing the raw material of Example 1, or Example 2:

n-$C_5H_{11}$—Ph—CF=CF—Ph—$C_7H_{15}$(n)
n-$C_5H_{11}$—Ph—CF=CF—Ph—$C_9H_{19}$(n)

n-$C_6H_{13}$—Ph—CF=CF—Ph—$C_7H_{15}$(n)
n-$C_6H_{13}$—Ph—CF=CF—Ph—$C_9H_{19}$(n)

n-$C_7H_{15}$—Ph—CF=CF—Ph—$C_8H_{17}$(n)
n-$C_7H_{15}$—Ph—CF=CF—Ph—$C_{10}H_{21}$(n)
n-$C_8H_{17}$—Ph—CF=CF—Ph—$C_9H_{19}$(n)

n-$C_9H_{19}$—Ph—CF=CF—Ph—$C_{10}H_{21}$(n)

CH₃O—Ph—CF=CF—Ph—CN (m.p. 118.1° C, c.p. 173.8° C.)
C₂H₅O—Ph—CF=CF—Ph—CN
n-C₄H₉O—Ph—CF=CF—Ph—CN (m.p. 70.8° C, c.p. 163.6° C.)
n-C₅H₁₁O—Ph—CF=CF—Ph—CN
n-C₇H₁₅O—Ph—CF=CF—Ph—CN
n-C₉H₁₉O—Ph—CF=CF—Ph—CN
CH₃O—Ph—CF=CF—Ph—CH₃

Figure 6:
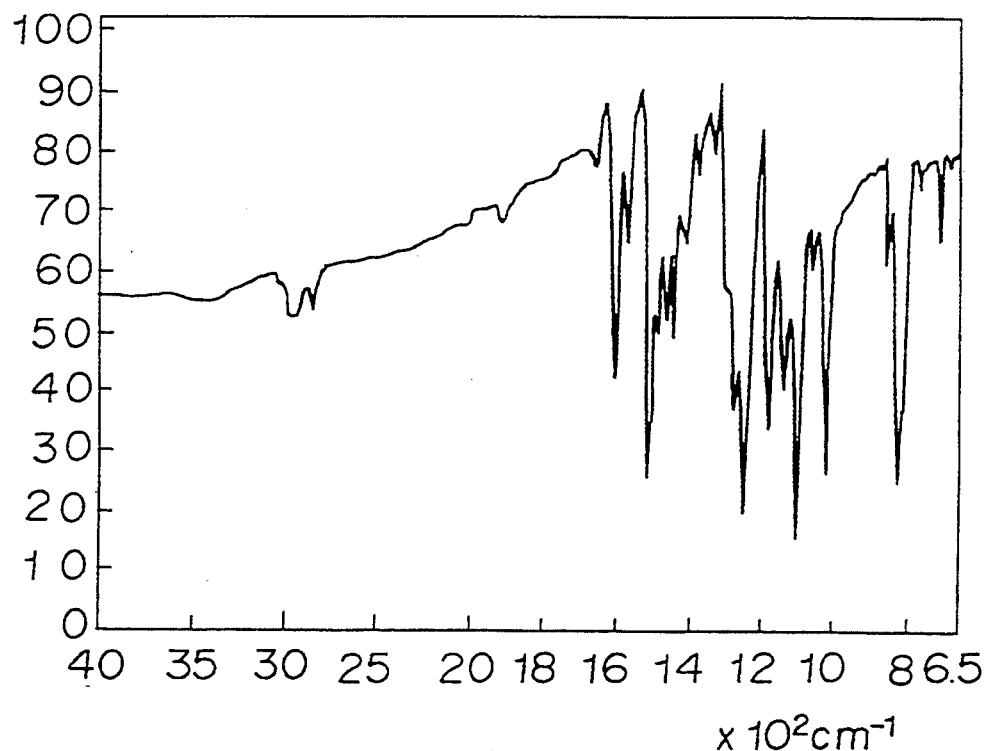

(m.p. 70.0° C, IR spectrum: shown in FIG. 6)
CH₃O—Ph—CF=CF—Ph—C₂H₅
CH₃O—Ph—CF=CF—Ph—C₄H₉(n)
CH₃O—Ph—CF=CF—Ph—C₆H₁₃(n)
CH₃O—Ph—CF=CF—Ph—C₈H₁₇(n)
CH₃O—Ph—CF=CF—Ph—C₁₀H₂₁(n)
C₂H₅O—Ph—CF=CF—Ph—CH₃
C₂H₅O—Ph—CF=CF—Ph—C₃H₇(n)
C₂H₅O—Ph—CF=CF—Ph—C₅H₁₁(n)
C₂H₅O—Ph—CF=CF—Ph—C₇H₁₅(n)
C₂H₅O—Ph—CF=CF—Ph—C₉H₁₉(n)
n-C₃H₇O—Ph—CF=CF—Ph—CH₃
n-C₃H₇O—Ph—CF=CF—Ph—C₃H₇(n)
n-C₃H₇O—Ph—CF=CF—Ph—C₅H₁₁(n)
n-C₃H₇O—Ph—CF=CF—Ph—C₇H₁₅(n)
n-C₃H₇O—Ph—CF=CF—Ph—C₉H₁₉(n)
n-C₄H₉O—Ph—CF=CF—Ph—CH₃
n-C₄H₉O—Ph—CF=CF—Ph—C₃H₇(n)
n-C₄H₉O—Ph—CF=CF—Ph—C₅H₁₁(n)
n-C₄H₉O—Ph—CF=CF—Ph—C₇H₁₅(n)
n-C₄H₉O—Ph—CF=CF—Ph—C₉H₁₉(n)
n-C₅H₁₁O—Ph—CF=CF—Ph—CH₃
n-C₅H₁₁O—Ph—CF=CF—Ph—C₃H₇(n)
n-C₅H₁₁O—Ph—CF=CF—Ph—C₅H₁₁(n)
n-C₅H₁₁O—Ph—CF=CF—Ph—C₇H₁₅(n)
n-C₅H₁₁O—Ph—CF=CF—Ph—C₉H₁₉(n)
n-C₆H₁₃O—Ph—CF=CF—Ph—CH₃
n-C₆H₁₃O—Ph—CF=CF—Ph—C₃H₇(n)
n-C₆H₁₃O—Ph—CF=CF—Ph—C₅H₁₁(n)
n-C₆H₁₃O—Ph—CF=CF—Ph—C₇H₁₅(n)
n-C₆H₁₃O—Ph—CF=CF—Ph—C₉H₁₉(n)
n-C₇H₁₅O—Ph—CF=CF—Ph—CH₃
n-C₇H₁₅O—Ph—CF=CF—Ph—C₃H₇(n)
n-C₇H₁₅O—Ph—CF=CF—Ph—C₅H₁₁(n)
n-C₇H₁₅O—Ph—CF=CF—Ph—C₇H₁₅(n)
n-C₇H₁₅O—Ph—CF=CF—Ph—C₉H₁₉(n)
n-C₈H₁₇O—Ph—CF=CF—Ph—CH₃
n-C₈H₁₇O—Ph—CF=CF—Ph—C₃H₇(n)
n-C₈H₁₇O—Ph—CF=CF—Ph—C₅H₁₁(n)
n-C₈H₁₇O—Ph—CF=CF—Ph—C₇H₁₅(n)
n-C₈H₁₇O—Ph—CF=CF—Ph—C₉H₁₉(n)
n-C₉H₁₉O—Ph—CF=CF—Ph—CH₃
n-C₉H₁₉O—Ph—CF=CF—Ph—C₃H₇(n)
n-C₉H₁₉O—Ph—CF=CF—Ph—C₅H₁₁(n)
n-C₉H₁₉O—Ph—CF=CF—Ph—C₇H₁₅(n)

n-C₃H₇O—Ph—CF=CF—Ph—CN n-C₆H₁₃O—Ph—CF=CF—Ph—CN
n-C₈H₁₇O—Ph—CF=CF—Ph—CN
n-C₁₀H₂₁O—Ph—CF=CF—Ph—CN

CH₃O—Ph—CF=CF—Ph—C₃H₇(n)
CH₃O—Ph—CF=CF—Ph—C₅H₁₁(n)
CH₃O—Ph—CF=CF—Ph—C₇H₁₅(n)
CH₃O—Ph—CF=CF—Ph—C₉H₁₉(n)
C₂H₅O—Ph—CF=CF—Ph—C₂H₅
C₂H₅O—Ph—CF=CF—Ph—C₄H₉(n)
C₂H₅O—Ph—CF=CF—Ph—C₆H₁₃(n)
C₂H₅O—Ph—CF=CF—Ph—C₈H₁₇(n)
C₂H₅O—Ph—CF=CF—Ph—C₁₀H₂₁(n)
n-C₃H₇O—Ph—CF=CF—Ph—C₂H₅
n-C₃H₇O—Ph—CF=CF—Ph—C₄H₉(n)
n-C₃H₇O—Ph—CF=CF—Ph—C₆H₁₃(n)
n-C₃H₇O—Ph—CF=CF—Ph—C₈H₁₇(n)
n-C₃H₇O—Ph—CF=CF—Ph—C₁₀H₂₁(n)
n-C₄H₉O—Ph—CF=CF—Ph—C₂H₅
n-C₄H₉O—Ph—CF=CF—Ph—C₄H₉(n)
n-C₄H₉O—Ph—CF=CF—Ph—C₆H₁₃(n)
n-C₄H₉O—Ph—CF=CF—Ph—C₈H₁₇(n)
n-C₄H₉O—Ph—CF=CF—Ph—C₁₀H₂₁(n)
n-C₅H₁₁O—Ph—CF=CF—Ph—C₂H₅
n-C₅H₁₁O—Ph—CF=CF—Ph—C₄H₉(n)
n-C₅H₁₁O—Ph—CF=CF—Ph—C₆H₁₃(n)
n-C₅H₁₁O—Ph—CF=CF—Ph—C₈H₁₇(n)
n-C₅H₁₁O—Ph—CF=CF—Ph—C₁₀H₂₁(n)
n-C₆H₁₃O—Ph—CF=CF—Ph—C₂H₅
n-C₆H₁₃O—Ph—CF=CF—Ph—C₄H₉(n)
n-C₆H₁₃O—Ph—CF=CF—Ph—C₆H₁₃(n)
n-C₆H₁₃O—Ph—CF=CF—Ph—C₈H₁₇(n)
n-C₆H₁₃O—Ph—CF=CF—Ph—C₁₀H₂₁(n)
n-C₇H₁₅O—Ph—CF=CF—Ph—C₂H₅
n-C₇H₁₅O—Ph—CF=CF—Ph—C₄H₉(n)
n-C₇H₁₅O—Ph—CF=CF—Ph—C₆H₁₃(n)
n-C₇H₁₅O—Ph—CF=CF—Ph—C₈H₁₇(n)
n-C₇H₁₅O—Ph—CF=CF—Ph—C₁₀H₂₁(n)
n-C₈H₁₇O—Ph—CF=CF—Ph—C₂H₅
n-C₈H₁₇O—Ph—CF=CF—Ph—C₄H₉(n)
n-C₈H₁₇O—Ph—CF=CF—Ph—C₆H₁₃(n)
n-C₈H₁₇O—Ph—CF=CF—Ph—C₈H₁₇(n)
n-C₈H₁₇O—Ph—CF=CF—Ph—C₁₀H₂₁(n)
n-C₉H₁₉O—Ph—CF=CF—Ph—C₂H₅
n-C₉H₁₉O—Ph—CF=CF—Ph—C₄H₉(n)
n-C₉H₁₉O—Ph—CF=CF—Ph—C₆H₁₃(n)
n-C₉H₁₉O—Ph—CF=CF—Ph—C₈H₁₇(n)

-continued n-C9H19O—Ph—CF=CF—Ph—C9H19(n)
n-C10H21O—Ph—CF=CF—Ph—CH3
n-C10H21O—Ph—CF=CF—Ph—C3H7(n)
n-C10H21O—Ph—CF=CF—Ph—C5H11(n)
n-C10H21O—Ph—CF=CF—Ph—C7H15(n)
n-C10H21O—Ph—CF=CF—Ph—C9H19(n)
CH3O—Ph—CF=CF—Ph—OCH3

Figure 7:
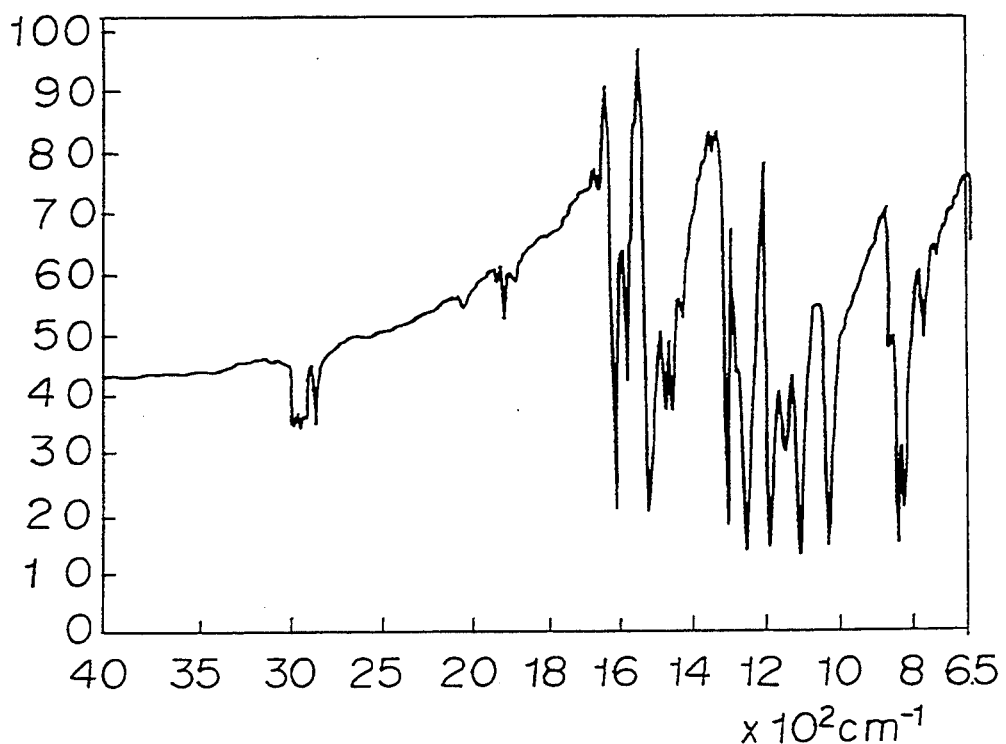

(m.p. 143.6° C., c.p. 154.3° C., IR spectrum: shown in FIG. 7)
CH3O—Ph—CF=CF—Ph—OC2H5
CH3O—Ph—CF=CF—Ph—OC4H9(n)
CH3O—Ph—CF=CF—Ph—OC6H13(n)
CH3O—Ph—CF=CF—Ph—OC8H17(n)
CH3O—Ph—CF=CF—Ph—OC10H21(n)
C2H5O—Ph—CF=CF—Ph—OC2H5

Figure 8:
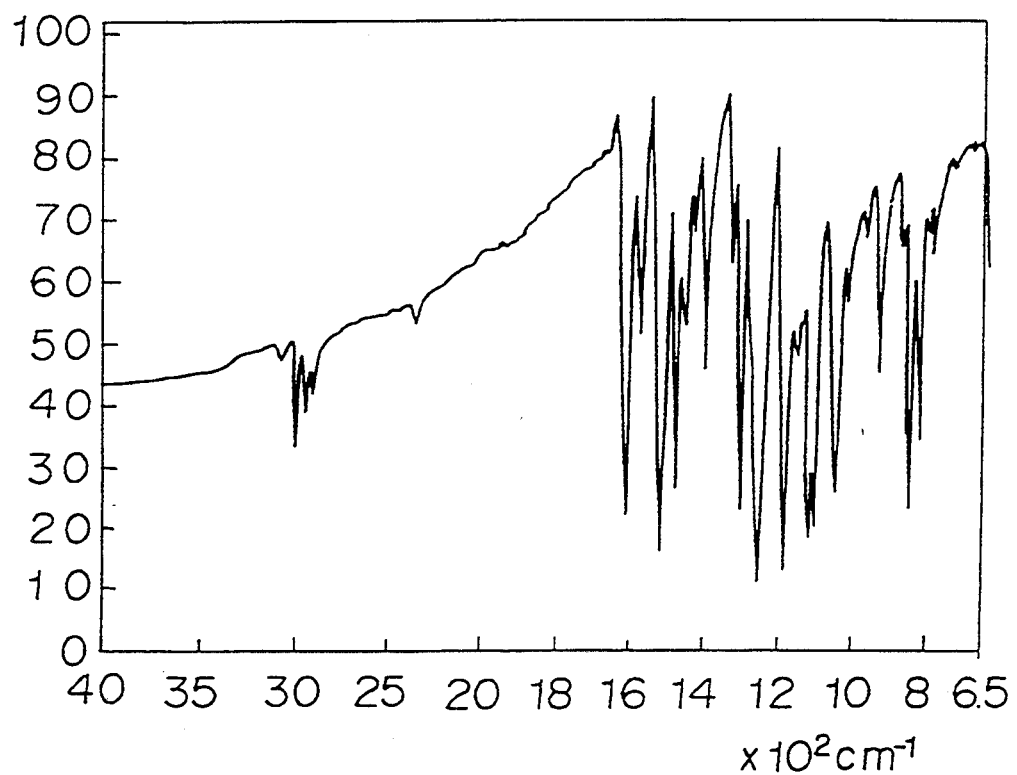

(m.p. 157.5° C., c.p. 173.0° C., IR spectrum: shown in FIG. 8)
C2H5O—Ph—CF=CF—Ph—OC3H7(n)
C2H5O—Ph—CF=CF—Ph—OC5H11(n)
C2H5O—Ph—CF=CF—Ph—OC7H15(n)
C2H5O—Ph—CF=CF—Ph—OC9H19(n)
C2H5O—Ph—CF=CF—Ph—OC10H21(n)
n-C3H7O—Ph—CF=CF—Ph—OC3H7(n)

Figure 9:
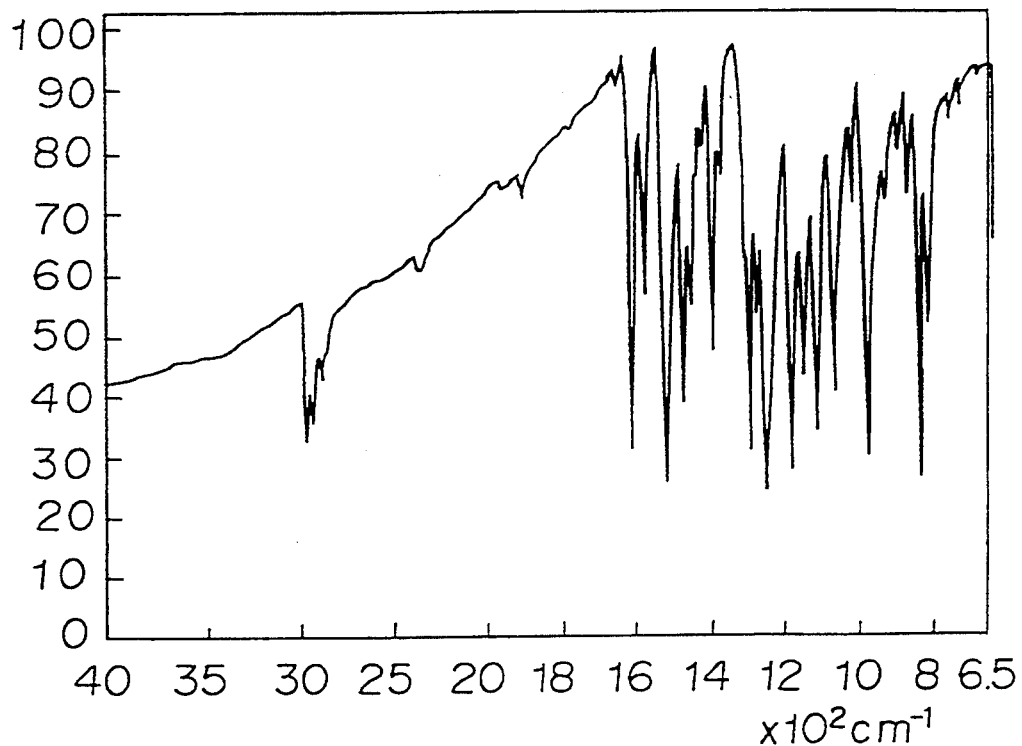

(m.p. 128.5° C., (c.p. 137.5° C., IR spectrum: shown in FIG. 9)
n-C3H7O—Ph—CF=CF—Ph—OC4H9(n)
n-C3H7O—Ph—CF=CF—Ph—OC6H13(n)
n-C3H7O—Ph—CF=CF—Ph—OC8H17(n)
n-C3H7O—Ph—CF=CF—Ph—OC10H21(n)
n-C4H9O—Ph—CF=CF—Ph—OC4H9(n)

(m.p. 109.3° C., c.p. 146.0° C., IR spectrum: shown in FIG. 10)
n-C4H9O—Ph—CF=CF—Ph—OC5H11(n)
n-C4H9O—Ph—CF=CF—Ph—OC7H15(n)
n-C4H9O—Ph—CF=CF—Ph—OC9H19(n)
n-C5H11O—Ph—CF=CF—Ph—OC5H11(n)

(m.p. 97.7° C., c.p. 150.3° C., IR spectrum: shown in FIG. 11)
n-C5H11O—Ph—CF=CF—Ph—OC6H13(n)
n-C5H11O—Ph—CF=CF—Ph—OC8H17(n)
n-C5H11O—Ph—CF=CF—Ph—OC10H21(n)
n-C6H13O—Ph—CF=CF—Ph—OC6H13(n)

Figure 12:
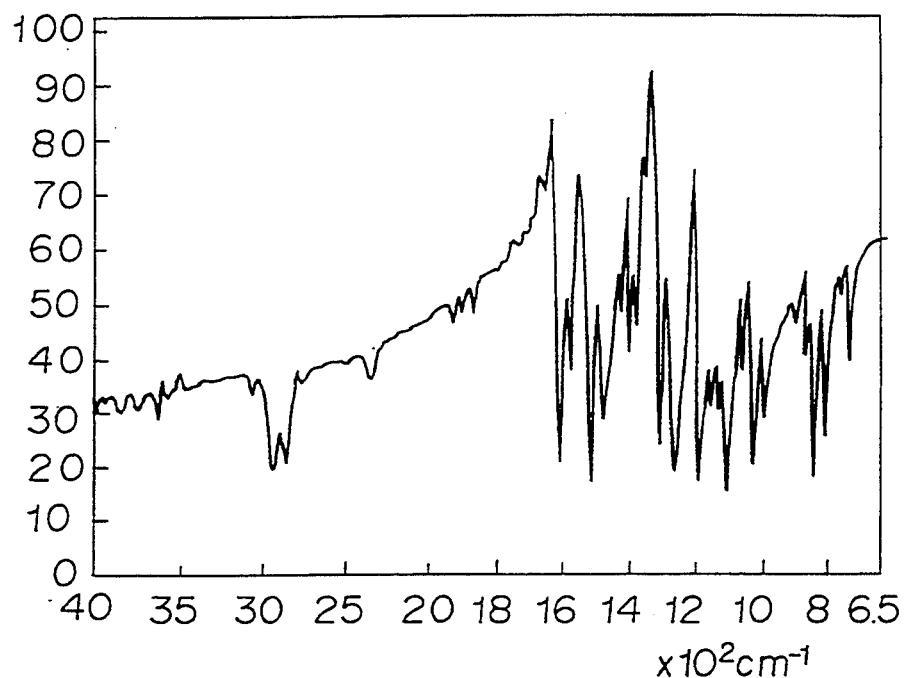

(m.p. 87.6° C., c.p. 130.2° C., IR spectrum: shown in FIG. 12)
n-C6H13O—Ph—CF=CF—Ph—OC7H15(n)
n-C6H13O—Ph—CF=CF—Ph—OC9H19(n)
n-C7H15O—Ph—CF=CF—Ph—OC8H17(n)
n-C7H15O—Ph—CF=CF—Ph—OC10H21(n)
n-C8H17O—Ph—CF=CF—Ph—OC8H17(n)
n-C8H17O—Ph—CF=CF—Ph—OC9H19(n)
n-C9H19O—Ph—CF=CF—Ph—OC9H19(n)
n-C10H21O—Ph—CF=CF—Ph—OC10H21(n)

n-C9H19O—Ph—CF=CF—Ph—C10H21(n)
n-C10H21O—Ph—CF=CF—Ph—C2H5
n-C10H21O—Ph—CF=CF—Ph—C4H9(n)
n-C10H21O—Ph—CF=CF—Ph—C6H13(n)
n-C10H21O—Ph—CF=CF—Ph—C8H17(n)
n-C10H21O—Ph—CF=CF—Ph—C10H21(n)
CH3O—Ph—CF=CF—Ph—OC3H7(n)
CH3O—Ph—CF=CF—Ph—OC5H11(n)
CH3O—Ph—CF=CF—Ph—OC7H15(n)
CH3O—Ph—CF=CF—Ph—OC9H19(n)

C2H5O—Ph—CF=CF—Ph—OC4H9(n)
C2H5O—Ph—CF=CF—Ph—OC6H13(n)
C2H5O—Ph—CF=CF—Ph—OC8H17(n)
C2H5O—Ph—CF=CF—Ph—OC10H21(n)

n-C3H7O—Ph—CF=CF—Ph—OC5H11(n)
n-C3H7O—Ph—CF=CF—Ph—OC7H15(n)
n-C3H7O—Ph—CF=CF—Ph—OC9H19(n)

n-C4H9O—Ph—CF=CF—Ph—OC6H13(n)
n-C4H9O—Ph—CF=CF—Ph—OC8H17(n)
n-C4H9O—Ph—CF=CF—Ph—OC10H21(n)

n-C5H11O—Ph—CF=CF—Ph—OC7H15(n)
n-C5H11O—Ph—CF=CF—Ph—OC9H19(n)

n-C6H13O—Ph—CF=CF—Ph—OC8H17(n)
n-C6H13O—Ph—CF=CF—Ph—OC10H21(n)
n-C7H15O—Ph—CF=CF—Ph—OC8H17(n)
n-C7H15O—Ph—CF=CF—Ph—OC10H21(n)
n-C8H17O—Ph—CF=CF—Ph—OC9H19(n)
n-C9H19O—Ph—CF=CF—Ph—OC9H19(n)
n-C10H21O—Ph—CF=CF—Ph—OC10H21(n)

The following compounds can be prepared by changing tetrafluoroethylene to tetrachloroethylene:

CH₃—Ph—CCl=CCl—Ph—CN
Trans-4-methyl-4'-cyano-α,α'-dichlorostilbene

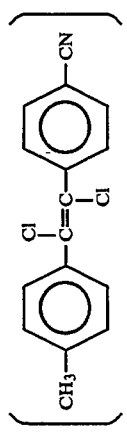

C₂H₅—Ph—CCl=CCl—Ph—CN
n-C₄H₉—Ph—CCl=CCl—Ph—CN
n-C₆H₁₃—Ph—CCl=CCl—Ph—CN
n-C₈H₁₇—Ph—CCl=CCl—Ph—CN
n-C₁₀H₂₁—Ph—CCl=CCl—Ph—CN
CH₃—Ph—CCl=CCl—Ph—C₂H₅
CH₃—Ph—CCl=CCl—Ph—C₄H₉(n)
CH₃—Ph—CCl=CCl—Ph—C₆H₁₃(n)
CH₃—Ph—CCl=CCl—Ph—C₈H₁₇(n)
CH₃—Ph—CCl=CCl—Ph—C₁₀H₂₁(n)
C₂H₅—Ph—CCl=CCl—Ph—C₃H₇(n)
C₂H₅—Ph—CCl=CCl—Ph—C₅H₁₁(n)
C₂H₅—Ph—CCl=CCl—Ph—C₇H₁₅(n)
C₂H₅—Ph—CCl=CCl—Ph—C₉H₁₉(n)
n-C₃H₇—Ph—CCl=CCl—Ph—C₃H₇(n)
n-C₃H₇—Ph—CCl=CCl—Ph—C₅H₁₁(n)
n-C₃H₇—Ph—CCl=CCl—Ph—C₇H₁₅(n)
n-C₃H₇—Ph—CCl=CCl—Ph—C₉H₁₉(n)
n-C₄H₉—Ph—CCl=CCl—Ph—C₄H₉(p)
n-C₄H₉—Ph—CCl=CCl—Ph—C₆H₁₃(n)
n-C₄H₉—Ph—CCl=CCl—Ph—C₈H₁₇(n)
n-C₄H₉—Ph—CCl=CCl—Ph—C₁₀H₂₁(n)
n-C₅H₁₁—Ph—CCl=CCl—Ph—C₅H₁₁(n)
n-C₅H₁₁—Ph—CCl=CCl—Ph—C₇H₁₅(n)
n-C₅H₁₁—Ph—CCl=CCl—Ph—C₈H₁₇(n)
n-C₆H₁₃—Ph—CCl=CCl—Ph—C₇H₁₅(n)
n-C₆H₁₃—Ph—CCl=CCl—Ph—C₉H₁₉(n)
n-C₇H₁₅—Ph—CCl=CCl—Ph—C₇H₁₅(n)
n-C₈H₁₇—Ph—CCl=CCl—Ph—C₉H₁₉(n)
n-C₈H₁₇—Ph—CCl=CCl—Ph—C₁₀H₂₁(n)
n-C₉H₁₉—Ph—CCl=CCl—Ph—C₁₀H₂₁(n)

n-C₃H₇—Ph—CCl=CCl—Ph—CN
n-C₅H₁₁—Ph—CCl=CCl—Ph—CN
n-C₇H₁₅—Ph—CCl=CCl—Ph—CN
n-C₉H₁₉—Ph—CCl=CCl—Ph—CN
CH₃—Ph—CCl=CCl—Ph—CH₃
CH₃—Ph—CCl=CCl—Ph—C₃H₇(n)
CH₃—Ph—CCl=CCl—Ph—C₅H₁₁(n)
CH₃—Ph—CCl=CCl—Ph—C₇H₁₅(n)
CH₃—Ph—CCl=CCl—Ph—C₉H₁₉(n)
C₂H₅—Ph—CCl=CCl—Ph—C₂H₅
C₂H₅—Ph—CCl=CCl—Ph—C₄H₉(n)
C₂H₅—Ph—CCl=CCl—Ph—C₆H₁₃(n)
C₂H₅—Ph—CCl=CCl—Ph—C₈H₁₇(n)
C₂H₅—Ph—CCl=CCl—Ph—C₁₀H₂₁(n)
n-C₃H₇—Ph—CCl=CCl—Ph—C₄H₉(n)
n-C₃H₇—Ph—CCl=CCl—Ph—C₆H₁₃(n)
n-C₃H₇—Ph—CCl=CCl—Ph—C₈H₁₇(n)
n-C₃H₇—Ph—CCl=CCl—Ph—C₁₀H₂₁(n)
n-C₄H₉—Ph—CCl=CCl—Ph—C₅H₁₁(n)
n-C₄H₉—Ph—CCl=CCl—Ph—C₇H₁₅(n)
n-C₄H₉—Ph—CCl=CCl—Ph—C₉H₁₉(n)
n-C₅H₁₁—Ph—CCl=CCl—Ph—C₆H₁₃(n)
n-C₅H₁₁—Ph—CCl=CCl—Ph—C₈H₁₇(n)
n-C₅H₁₁—Ph—CCl=CCl—Ph—C₁₀H₂₁(n)
n-C₆H₁₃—Ph—CCl=CCl—Ph—C₆H₁₃(n)
n-C₆H₁₃—Ph—CCl=CCl—Ph—C₈H₁₇(n)
n-C₆H₁₃—Ph—CCl=CCl—Ph—C₁₀H₂₁(n)
n-C₇H₁₅—Ph—CCl=CCl—Ph—C₈H₁₇(n)
n-C₇H₁₅—Ph—CCl=CCl—Ph—C₁₀H₂₁(n)
n-C₈H₁₇—Ph—CCl=CCl—Ph—C₈H₁₇(n)
n-C₉H₁₉—Ph—CCl=CCl—Ph—C₉H₁₉(n)
n-C₁₀H₂₁—Ph—CCl=CCl—Ph—C₁₀H₂₁(n)

The following compounds can be prepared by changing the raw material of Example 1 or Example 2.

| | |
|---|---|
| CH₃O—Ph—CCl=CCl—Ph—CN | C₂H₅O—Ph—CCl=CCl—Ph—CN |
| n-C₃H₇O—Ph—CCl=CCl—Ph—CN | n-C₄H₉O—Ph—CCl=CCl—Ph—CN |
| n-C₅H₁₁O—Ph—CCl=CCl—Ph—CN | n-C₆H₁₃O—Ph—CCl=CCl—Ph—CN |
| n-C₇H₁₅O—Ph—CCl=CCl—Ph—CN | n-C₈H₁₇O—Ph—CCl=CCl—Ph—CN |
| n-C₉H₁₉O—Ph—CCl=CCl—Ph—CN | n-C₁₀H₂₁O—Ph—CCl=CCl—Ph—CN |
| CH₃O—Ph—CCl=CCl—Ph—CH₃ | CH₃O—Ph—CCl=CCl—Ph—C₂H₅ |
| CH₃O—Ph—CCl=CCl—Ph—C₃H₇(n) | CH₃O—Ph—CCl=CCl—Ph—C₄H₉(n) |
| CH₃O—Ph—CCl=CCl—Ph—C₅H₁₁(n) | CH₃O—Ph—CCl=CCl—Ph—C₆H₁₃(n) |
| CH₃O—Ph—CCl=CCl—Ph—C₇H₁₅(n) | CH₃O—Ph—CCl=CCl—Ph—C₈H₁₇(n) |
| CH₃O—Ph—CCl=CCl—Ph—C₉H₁₉(n) | CH₃O—Ph—CCl=CCl—Ph—C₁₀H₂₁(n) |
| C₂H₅O—Ph—CCl=CCl—Ph—CH₃ | C₂H₅O—Ph—CCl=CCl—Ph—C₂H₅ |
| C₂H₅O—Ph—CCl=CCl—Ph—C₃H₇(n) | C₂H₅O—Ph—CCl=CCl—Ph—C₄H₉(n) |
| C₂H₅O—Ph—CCl=CCl—Ph—C₅H₁₁(n) | C₂H₅O—Ph—CCl=CCl—Ph—C₆H₁₃(n) |
| C₂H₅O—Ph—CCl=CCl—Ph—C₇H₁₅(n) | C₂H₅O—Ph—CCl=CCl—Ph—C₈H₁₇(n) |
| C₂H₅O—Ph—CCl=CCl—Ph—C₉H₁₉(n) | C₂H₅O—Ph—CCl=CCl—Ph—C₁₀H₂₁(n) |
| n-C₃H₇O—Ph—CCl=CCl—Ph—CH₃ | n-C₃H₇O—Ph—CCl=CCl—Ph—C₂H₅ |
| n-C₃H₇O—Ph—CCl=CCl—Ph—C₃H₇(n) | n-C₃H₇O—Ph—CCl=CCl—Ph—C₄H₉(n) |
| n-C₃H₇O—Ph—CCl=CCl—Ph—C₅H₁₁(n) | n-C₃H₇O—Ph—CCl=CCl—Ph—C₆H₁₃(n) |
| n-C₃H₇O—Ph—CCl=CCl—Ph—C₇H₁₅(n) | n-C₃H₇O—Ph—CCl=CCl—Ph—C₈H₁₇(n) |
| n-C₃H₇O—Ph—CCl=CCl—Ph—C₉H₁₉(n) | n-C₃H₇O—Ph—CCl=CCl—Ph—C₁₀H₂₁(n) |
| n-C₄H₉O—Ph—CCl=CCl—Ph—CH₃ | n-C₄H₉O—Ph—CCl=CCl—Ph—C₂H₅ |
| n-C₄H₉O—Ph—CCl=CCl—Ph—C₃H₇(n) | n-C₄H₉O—Ph—CCl=CCl—Ph—C₄H₉(n) |
| n-C₄H₉O—Ph—CCl=CCl—Ph—C₅H₁₁(n) | n-C₄H₉O—Ph—CCl=CCl—Ph—C₆H₁₃(n) |
| n-C₄H₉O—Ph—CCl=CCl—Ph—C₇H₁₅(n) | n-C₄H₉O—Ph—CCl=CCl—Ph—C₈H₁₇(n) |
| n-C₄H₉O—Ph—CCl=CCl—Ph—C₉H₁₉(n) | n-C₄H₉O—Ph—CCl=CCl—Ph—C₁₀H₂₁(n) |
| n-C₅H₁₁O—Ph—CCl=CCl—Ph—CH₃ | n-C₅H₁₁O—Ph—CCl=CCl—Ph—C₂H₅ |
| n-C₅H₁₁O—Ph—CCl=CCl—Ph—C₃H₇(n) | n-C₅H₁₁O—Ph—CCl=CCl—Ph—C₄H₉(n) |
| n-C₅H₁₁O—Ph—CCl=CCl—Ph—C₅H₁₁(n) | n-C₅H₁₁O—Ph—CCl=CCl—Ph—C₆H₁₃(n) |
| n-C₅H₁₁O—Ph—CCl=CCl—Ph—C₇H₁₅(n) | n-C₅H₁₁O—Ph—CCl=CCl—Ph—C₈H₁₇(n) |
| n-C₅H₁₁O—Ph—CCl=CCl—Ph—C₉H₁₉(n) | n-C₅H₁₁O—Ph—CCl=CCl—Ph—C₁₀H₂₁(n) |
| n-C₆H₁₃O—Ph—CCl=CCl—Ph—CH₃ | n-C₆H₁₃O—Ph—CCl=CCl—Ph—C₂H₅ |
| n-C₆H₁₃O—Ph—CCl=CCl—Ph—C₃H₇(n) | n-C₆H₁₃O—Ph—CCl=CCl—Ph—C₄H₉(n) |
| n-C₆H₁₃O—Ph—CCl=CCl—Ph—C₅H₁₁(n) | n-C₆H₁₃O—Ph—CCl=CCl—Ph—C₆H₁₃(n) |
| n-C₆H₁₃O—Ph—CCl=CCl—Ph—C₇H₁₅(n) | n-C₆H₁₃O—Ph—CCl=CCl—Ph—C₈H₁₇(n) |
| n-C₆H₁₃O—Ph—CCl=CCl—Ph—C₉H₁₉(n) | n-C₆H₁₃O—Ph—CCl=CCl—Ph—C₁₀H₂₁(n) |
| n-C₇H₁₅O—Ph—CCl=CCl—Ph—CH₃ | n-C₇H₁₅O—Ph—CCl=CCl—Ph—C₂H₅ |
| n-C₇H₁₅O—Ph—CCl=CCl—Ph—C₃H₇(n) | n-C₇H₁₅O—Ph—CCl=CCl—Ph—C₄H₉(n) |
| n-C₇H₁₅O—Ph—CCl=CCl—Ph—C₅H₁₁(n) | n-C₇H₁₅O—Ph—CCl=CCl—Ph—C₆H₁₃(n) |
| n-C₇H₁₅O—Ph—CCl=CCl—Ph—C₇H₁₅(n) | n-C₇H₁₅O—Ph—CCl=CCl—Ph—C₈H₁₇(n) |
| n-C₇H₁₅O—Ph—CCl=CCl—Ph—C₉H₁₉(n) | n-C₇H₁₅O—Ph—CCl=CCl—Ph—C₁₀H₂₁(n) |
| n-C₈H₁₇O—Ph—CCl=CCl—Ph—CH₃ | n-C₈H₁₇O—Ph—CCl=CCl—Ph—C₂H₅ |
| n-C₈H₁₇O—Ph—CCl=CCl—Ph—C₃H₇(n) | n-C₈H₁₇O—Ph—CCl=CCl—Ph—C₄H₉(n) |
| n-C₈H₁₇O—Ph—CCl=CCl—Ph—C₅H₁₁(n) | n-C₈H₁₇O—Ph—CCl=CCl—Ph—C₆H₁₃(n) |
| n-C₈H₁₇O—Ph—CCl=CCl—Ph—C₇H₁₅(n) | n-C₈H₁₇O—Ph—CCl=CCl—Ph—C₈H₁₇(n) |
| n-C₈H₁₇O—Ph—CCl=CCl—Ph—C₉H₁₉(n) | n-C₈H₁₇O—Ph—CCl=CCl—Ph—C₁₀H₂₁(n) |
| n-C₉H₁₉O—Ph—CCl=CCl—Ph—CH₃ | n-C₉H₁₉O—Ph—CCl=CCl—Ph—C₂H₅ |
| n-C₉H₁₉O—Ph—CCl=CCl—Ph—C₃H₇(n) | n-C₉H₁₉O—Ph—CCl=CCl—Ph—C₄H₉(n) |
| n-C₉H₁₉O—Ph—CCl=CCl—Ph—C₅H₁₁(n) | n-C₉H₁₉O—Ph—CCl=CCl—Ph—C₆H₁₃(n) |
| n-C₉H₁₉O—Ph—CCl=CCl—Ph—C₇H₁₅(n) | n-C₉H₁₉O—Ph—CCl=CCl—Ph—C₈H₁₇(n) |
| n-C₉H₁₉O—Ph—CCl=CCl—Ph—C₉H₁₉(n) | n-C₉H₁₉O—Ph—CCl=CCl—Ph—C₁₀H₂₁(n) |
| n-C₁₀H₂₁O—Ph—CCl=CCl—Ph—CH₃ | n-C₁₀H₂₁O—Ph—CCl=CCl—Ph—C₂H₅ |
| n-C₁₀H₂₁O—Ph—CCl=CCl—Ph—C₃H₇(n) | n-C₁₀H₂₁O—Ph—CCl=CCl—Ph—C₄H₉(n) |
| n-C₁₀H₂₁O—Ph—CCl=CCl—Ph—C₅H₁₁(n) | n-C₁₀H₂₁O—Ph—CCl=CCl—Ph—C₆H₁₃(n) |

-continued

| | |
|---|---|
| n-C$_{10}$H$_{21}$O—Ph—CCl=CCl—Ph—OC$_7$H$_{15}$(n) | n-C$_{10}$H$_{21}$O—Ph—CCl=CCl—Ph—OC$_8$H$_{17}$(n) |
| n-C$_{10}$H$_{21}$O—Ph—CCl=CCl—Ph—OC$_9$H$_{19}$(n) | n-C$_{10}$H$_{21}$O—Ph—CCl=CCl—Ph—OC$_{10}$H$_{21}$(n) |
| CH$_3$O—Ph—CCl=CCl—Ph—OCH$_3$ | CH$_3$O—Ph—CCl=CCl—Ph—OC$_2$H$_5$ |
| CH$_3$O—Ph—CCl=CCl—Ph—OC$_3$H$_7$(n) | CH$_3$O—Ph—CCl=CCl—Ph—OC$_4$H$_9$(n) |
| CH$_3$O—Ph—CCl=CCl—Ph—OC$_5$H$_{11}$(n) | CH$_3$O—Ph—CCl=CCl—Ph—OC$_6$H$_{13}$(n) |
| CH$_3$O—Ph—CCl=CCl—Ph—OC$_7$H$_{15}$(n) | CH$_3$O—Ph—CCl=CCl—Ph—OC$_8$H$_{17}$(n) |
| CH$_3$O—Ph—CCl=CCl—Ph—OC$_9$H$_{19}$(n) | CH$_3$O—Ph—CCl=CCl—Ph—OC$_{10}$H$_{21}$(n) |
| C$_2$H$_5$O—Ph—CCl=CCl—Ph—OC$_2$H$_5$ | C$_2$H$_5$O—Ph—CCl=CCl—Ph—OC$_3$H$_7$(n) |
| C$_2$H$_5$O—Ph—CCl=CCl—Ph—OC$_4$H$_9$(n) | C$_2$H$_5$O—Ph—CCl=CCl—Ph—OC$_5$H$_{11}$(n) |
| C$_2$H$_5$O—Ph—CCl=CCl—Ph—OC$_6$H$_{13}$(n) | C$_2$H$_5$O—Ph—CCl=CCl—Ph—OC$_7$H$_{15}$(n) |
| C$_2$H$_5$O—Ph—CCl=CCl—Ph—OC$_8$H$_{17}$(n) | C$_2$H$_5$O—Ph—CCl=CCl—Ph—OC$_9$H$_{19}$(n) |
| C$_2$H$_5$O—Ph—CCl=CCl—Ph—OC$_{10}$H$_{21}$(n) | |
| n-C$_3$H$_7$O—Ph—CCl=CCl—Ph—OC$_3$H$_7$(n) | n-C$_3$H$_7$O—Ph—CCl=CCl—Ph—OC$_4$H$_9$(n) |
| n-C$_3$H$_7$O—Ph—CCl=CCl—Ph—OC$_5$H$_{11}$(n) | n-C$_3$H$_7$O—Ph—CCl=CCl—Ph—OC$_6$H$_{13}$(n) |
| n-C$_3$H$_7$O—Ph—CCl=CCl—Ph—OC$_7$H$_{15}$(n) | n-C$_3$H$_7$O—Ph—CCl=CCl—Ph—OC$_8$H$_{17}$(n) |
| n-C$_3$H$_7$O—Ph—CCl=CCl—Ph—OC$_9$H$_{19}$(n) | n-C$_3$H$_7$O—Ph—CCl=CCl—Ph—OC$_{10}$H$_{21}$(n) |
| n-C$_4$H$_9$O—Ph—CCl=CCl—Ph—OC$_4$H$_9$(n) | n-C$_4$H$_9$O—Ph—CCl=CCl—Ph—OC$_5$H$_{11}$(n) |
| n-C$_4$H$_9$O—Ph—CCl=CCl—Ph—OC$_6$H$_{13}$(n) | n-C$_4$H$_9$O—Ph—CCl=CCl—Ph—OC$_7$H$_{15}$(n) |
| n-C$_4$H$_9$O—Ph—CCl=CCl—Ph—OC$_8$H$_{17}$(n) | n-C$_4$H$_9$O—Ph—CCl=CCl—Ph—OC$_9$H$_{19}$(n) |
| n-C$_4$H$_9$O—Ph—CCl=CCl—Ph—OC$_{10}$H$_{21}$(n) | |
| n-C$_5$H$_{11}$O—Ph—CCl=CCl—Ph—OC$_5$H$_{11}$(n) | n-C$_5$H$_{11}$O—Ph—CCl=CCl—Ph—OC$_6$H$_{13}$(n) |
| n-C$_5$H$_{11}$O—Ph—CCl=CCl—Ph—OC$_7$H$_{15}$(n) | n-C$_5$H$_{11}$O—Ph—CCl=CCl—Ph—OC$_8$H$_{17}$(n) |
| n-C$_5$H$_{11}$O—Ph—CCl=CCl—Ph—OC$_9$H$_{19}$(n) | n-C$_5$H$_{11}$O—Ph—CCl=CCl—Ph—OC$_{10}$H$_{21}$(n) |
| n-C$_6$H$_{13}$O—Ph—CCl=CCl—Ph—OC$_6$H$_{13}$(n) | n-C$_6$H$_{13}$O—Ph—CCl=CCl—Ph—OC$_7$H$_{15}$(n) |
| n-C$_6$H$_{13}$O—Ph—CCl=CCl—Ph—OC$_8$H$_{17}$(n) | n-C$_6$H$_{13}$O—Ph—CCl=CCl—Ph—OC$_9$H$_{19}$(n) |
| n-C$_6$H$_{13}$O—Ph—CCl=CCl—Ph—OC$_{10}$H$_{21}$(n) | |
| n-C$_7$H$_{15}$O—Ph—CCl=CCl—Ph—OC$_7$H$_{15}$(n) | n-C$_7$H$_{15}$O—Ph—CCl=CCl—Ph—OC$_8$H$_{17}$(n) |
| n-C$_7$H$_{15}$O—Ph—CCl=CCl—Ph—OC$_9$H$_{19}$(n) | n-C$_7$H$_{15}$O—Ph—CCl=CCl—Ph—OC$_{10}$H$_{21}$(n) |
| n-C$_8$H$_{17}$O—Ph—CCl=CCl—Ph—OC$_8$H$_{17}$(n) | n-C$_8$H$_{17}$O—Ph—CCl=CCl—Ph—OC$_9$H$_{19}$(n) |
| n-C$_8$H$_{17}$O—Ph—CCl=CCl—Ph—OC$_{10}$H$_{21}$(n) | |
| n-C$_9$H$_{19}$O—Ph—CCl=CCl—Ph—OC$_9$H$_{19}$(n) | n-C$_9$H$_{19}$O—Ph—CCl=CCl—Ph—OC$_{10}$H$_{21}$(n) |
| n-C$_{10}$H$_{21}$O—Ph—CCl=CCl—Ph—OC$_{10}$H$_{21}$(n) | |

The following compounds can be prepared by changing the raw material of Example 1 or Example 2. In the following formulas, Ph represents a phenylene group Further, the following compounds can be prepared by changing tetrafluoroethylene to tetrachloroethylene.

CH₃—Ph—CCl=CCl—PhF—CN
Trans-4-methyl-4'-cyano-3'-fluoro-α,α'-dichlorostilbene

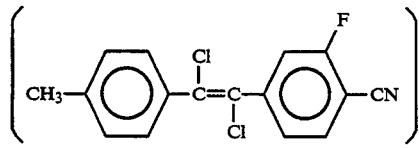

C₂H₅—Ph—CCl=CCl—PhF—CN
n-C₄H₉—Ph—CCl=CCl—PhF—CN
n-C₆H₁₃—Ph—CCl=CCl—PhF—CN
n-C₈H₁₇—Ph—CCl=CCl—PhF—CN
n-C₁₀H₂₁—Ph—CCl=CCl—PhF—CN
CH₃O—Ph—CCl=CCl—PhF—CN
n-C₃H₇O—Ph—CCl=CCl—PhF—CN
n-C₅H₁₁O—Ph—CCl=CCl—PhF—CN
n-C₇H₁₅O—Ph—CCl=CCl—PhF—CN
n-C₉H₁₉O—Ph—CCl=CCl—PhF—CN n-C₃H₇—Ph—CCl=CCl—PhF—CN
n-C₅H₁₁—Ph—CCl=CCl—PhF—CN
n-C₇H₁₅—Ph—CCl=CCl—PhF—CN
n-C₉H₁₉—Ph—CCl=CCl—PhF—CN

C₂H₅O—Ph—CCl=CCl—PhF—CN
n-C₄H₉O—Ph—CCl=CCl—PhF—CN
n-C₆H₁₃O—Ph—CCl=CCl—PhF—CN
n-C₈H₁₇O—Ph—CCl=CCl—PhF—CN
n-C₁₀H₂₁O—Ph—CCl=CCl—PhF—CN

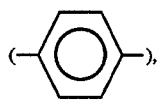

and PhF represents a fluorine-substituted phenylene group

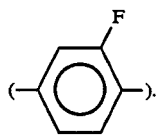

The following compounds can be prepared by changing the raw material of Example 1 or Example 2. In the following formulas, Cy—Ph and Ph—Cy represent p-(trans-4-substituted cyclohexyl)phenylene groups which have the following structures:

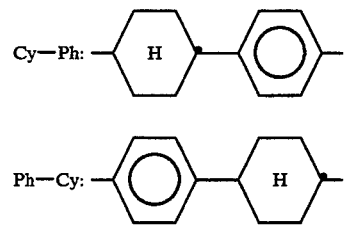

CH₃—Ph—CF=CF—PhF—CN
Trans-4-methyl-4'-cyano-3'-fluoro-α,α'-difluorostilbene

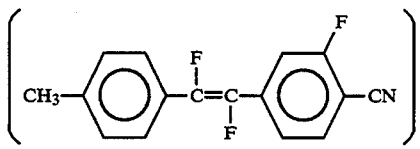

C₂H₅—Ph—CF=CF—PhF—CN
n-C₄H₉—Ph—CF=CF—PhF—CN
n-C₆H₁₃—Ph—CF=CF—PhF—CN
n-C₈H₁₇—Ph—CF=CF—PhF—CN
n-C₁₀H₂₁—Ph—CF=CF—PhF—CN
CH₃O—Ph—CF=CF—PhF—CN
n-C₃H₇O—Ph—CF=CF—PhF—CN
n-C₅H₁₁O—Ph—CF=CF—PhF—CN
n-C₇H₁₅O—Ph—CF=CF—PhF—CN
n-C₉H₁₉O—Ph—CF=CF—PhF—CN n-C₃H₇—Ph—CF=CF—PhF—CN
n-C₅H₁₁—Ph—CF=CF—PhF—CN
n-C₇H₁₅—Ph—CF=CF—PhF—CN
n-C₉H₁₉—Ph—CF=CF—PhF—CN

C₂H₅O—Ph—CF=CF—PhF—CN
n-C₄H₉O—Ph—CF=CF—PhF—CN
n-C₆H₁₃O—Ph—CF=CF—PhF—CN
n-C₈H₁₇O—Ph—CF=CF—PhF—CN
n-C₁₀H₂₁O—Ph—CF=CF—PhF—CN

CH₃—Cy—Ph—CF=CF—Ph—Cy—CH₃
Trans-4,4'-bis(4-methyl-trans-cyclohexyl)-α,α'-difluorostilbene

Figure 13:
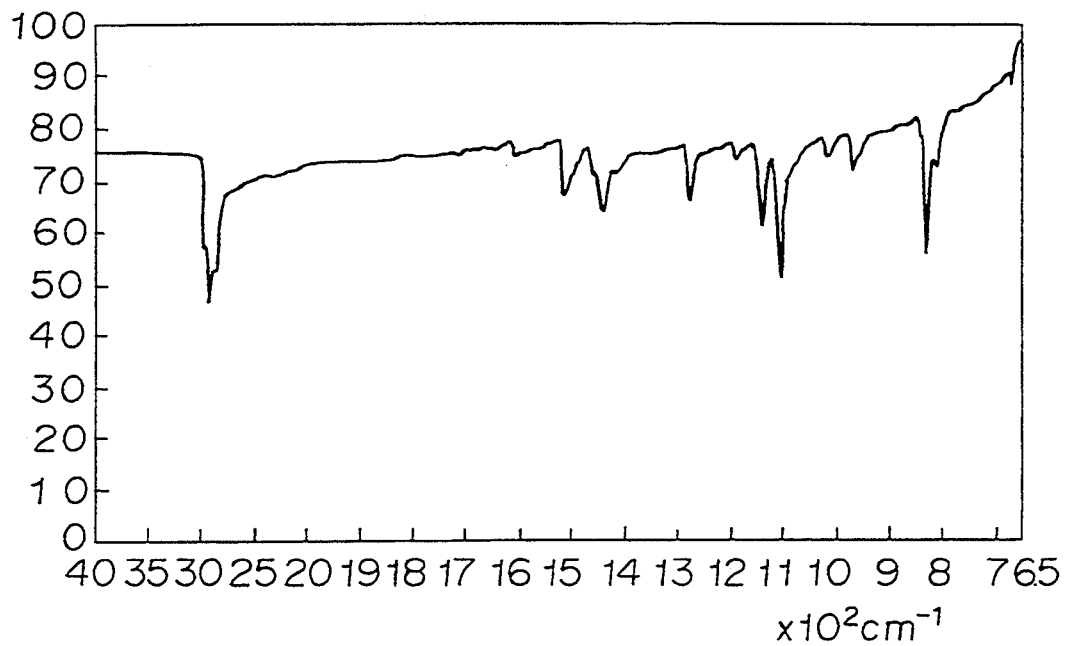

CH₃—Cy—Ph—CF=CF—Ph—Cy—C₃H₇(n)
CH₃—Cy—Ph—CF=CF—Ph—Cy—C₄H₉(n)
CH₃—Cy—Ph—CF=CF—Ph—Cy—C₅H₁₁(n)
CH₃—Cy—Ph—CF=CF—Ph—Cy—C₆H₁₃(n)
CH₃—Cy—Ph—CF=CF—Ph—Cy—C₇H₁₅(n)
CH₃—Cy—Ph—CF=CF—Ph—Cy—C₈H₁₇(n)
CH₃—Cy—Ph—CF=CF—Ph—Cy—C₁₀H₂₁(n)
C₂H₅—Cy—Ph—CF=CF—Ph—Cy—C₂H₅
C₂H₅—Cy—Ph—CF=CF—Ph—Cy—C₃H₇(n)
C₂H₅—Cy—Ph—CF=CF—Ph—Cy—C₄H₉(n)
C₂H₅—Cy—Ph—CF=CF—Ph—Cy—C₆H₁₃(n)
C₂H₅—Cy—Ph—CF=CF—Ph—Cy—C₈H₁₇(n)
C₂H₅—Cy—Ph—CF=CF—Ph—Cy—C₁₀H₂₁(n)
n-C₃H₇—Cy—Ph—CF=CF—Ph—Cy—C₃H₇(n)
(m.p. 164.2° C., c.p. 323.9° C., IR spectrum: shown in FIG. 13)
n-C₃H₇—Cy—Ph—CF=CF—Ph—Cy—C₅H₁₁(n)
n-C₃H₇—Cy—Ph—CF=CF—Ph—Cy—C₇H₁₅(n)
n-C₃H₇—Cy—Ph—CF=CF—Ph—Cy—C₉H₁₉(n)
n-C₄H₉—Cy—Ph—CF=CF—Ph—Cy—C₄H₉(n)
n-C₄H₉—Cy—Ph—CF=CF—Ph—Cy—C₅H₁₁(n)
n-C₄H₉—Cy—Ph—CF=CF—Ph—Cy—C₆H₁₃(n)
n-C₄H₉—Cy—Ph—CF=CF—Ph—Cy—C₈H₁₇(n)
n-C₄H₉—Cy—Ph—CF=CF—Ph—Cy—C₁₀H₂₁(n)
n-C₅H₁₁—Cy—Ph—CF=CF—Ph—Cy—C₅H₁₁(n)
n-C₅H₁₁—Cy—Ph—CF=CF—Ph—Cy—C₆H₁₃(n)
n-C₅H₁₁—Cy—Ph—CF=CF—Ph—Cy—C₇H₁₅(n)
n-C₅H₁₁—Cy—Ph—CF=CF—Ph—Cy—C₈H₁₇(n)
n-C₅H₁₁—Cy—Ph—CF=CF—Ph—Cy—C₉H₁₉(n)
n-C₅H₁₁—Cy—Ph—CF=CF—Ph—Cy—C₁₀H₂₁(n)
n-C₆H₁₃—Cy—Ph—CF=CF—Ph—Cy—C₆H₁₃(n)
n-C₆H₁₃—Cy—Ph—CF=CF—Ph—Cy—C₇H₁₅(n)
n-C₆H₁₃—Cy—Ph—CF=CF—Ph—Cy—C₈H₁₇(n)
n-C₆H₁₃—Cy—Ph—CF=CF—Ph—Cy—C₁₀H₂₁(n)
n-C₇H₁₅—Cy—Ph—CF=CF—Ph—Cy—C₈H₁₇(n)
n-C₇H₁₅—Cy—Ph—CF=CF—Ph—Cy—C₁₀H₂₁(n)
n-C₈H₁₇—Cy—Ph—CF=CF—Ph—Cy—C₉H₁₉(n)
n-C₈H₁₇—Cy—Ph—CF=CF—Ph—Cy—C₁₀H₂₁(n)
n-C₉H₁₉—Cy—Ph—CF=CF—Ph—Cy—C₁₀H₂₁(n)
CH₃O—Cy—Ph—CF=CF—Ph—Cy—C₂H₅
CH₃O—Cy—Ph—CF=CF—Ph—Cy—C₄H₉(n)
CH₃O—Cy—Ph—CF=CF—Ph—Cy—C₆H₁₃(n)
CH₃O—Cy—Ph—CF=CF—Ph—Cy—C₈H₁₇(n)
CH₃O—Cy—Ph—CF=CF—Ph—Cy—C₁₀H₂₁(n)
C₂H₅O—Cy—Ph—CF=CF—Ph—Cy—C₂H₅
C₂H₅O—Cy—Ph—CF=CF—Ph—Cy—C₄H₉(n)
C₂H₅O—Cy—Ph—CF=CF—Ph—Cy—C₆H₁₃(n)
C₂H₅O—Cy—Ph—CF=CF—Ph—Cy—C₈H₁₇(n)
C₂H₅O—Cy—Ph—CF=CF—Ph—Cy—C₁₀H₂₁(n)
n-C₃H₇O—Cy—Ph—CF=CF—Ph—Cy—C₂H₅
n-C₃H₇O—Cy—Ph—CF=CF—Ph—Cy—C₄H₉(n)

-continued n-C$_3$H$_7$O—Cy—Ph—CF=CF—Ph—Cy—C$_6$H$_{13}$(n)
n-C$_3$H$_7$O—Cy—Ph—CF=CF—Ph—Cy—C$_8$H$_{17}$(n)
n-C$_3$H$_7$O—Cy—Ph—CF=CF—Ph—Cy—C$_{10}$H$_{21}$(n)
n-C$_4$H$_9$O—Cy—Ph—CF=CF—Ph—Cy—C$_2$H$_5$
n-C$_4$H$_9$O—Cy—Ph—CF=CF—Ph—Cy—C$_4$H$_9$(n)
n-C$_4$H$_9$O—Cy—Ph—CF=CF—Ph—Cy—C$_6$H$_{13}$(n)
n-C$_4$H$_9$O—Cy—Ph—CF=CF—Ph—Cy—C$_8$H$_{17}$(n)
n-C$_4$H$_9$O—Cy—Ph—CF=CF—Ph—Cy—C$_{10}$H$_{21}$(n)
n-C$_5$H$_{11}$O—Cy—Ph—CF=CF—Ph—Cy—C$_2$H$_5$
n-C$_5$H$_{11}$O—Cy—Ph—CF=CF—Ph—Cy—C$_4$H$_9$(n)
n-C$_5$H$_{11}$O—Cy—Ph—CF=CF—Ph—Cy—C$_6$H$_{13}$(n)
n-C$_5$H$_{11}$O—Cy—Ph—CF=CF—Ph—Cy—C$_8$H$_{17}$(n)
n-C$_5$H$_{11}$O—Cy—Ph—CF=CF—Ph—Cy—C$_{10}$H$_{21}$(n)
n-C$_6$H$_{13}$O—Cy—Ph—CF=CF—Ph—Cy—C$_2$H$_5$
n-C$_6$H$_{13}$O—Cy—Ph—CF=CF—Ph—Cy—C$_4$H$_9$(n)
n-C$_6$H$_{13}$O—Cy—Ph—CF=CF—Ph—Cy—C$_6$H$_{13}$(n)
n-C$_6$H$_{13}$O—Cy—Ph—CF=CF—Ph—Cy—C$_8$H$_{17}$(n)
n-C$_6$H$_{13}$O—Cy—Ph—CF=CF—Ph—Cy—C$_{10}$H$_{21}$(n)

n-C$_3$H$_7$O—Cy—Ph—CF=CF—Ph—Cy—C$_5$H$_{11}$(n)
n-C$_3$H$_7$O—Cy—Ph—CF=CF—Ph—Cy—C$_7$H$_{15}$(n)
n-C$_3$H$_7$O—Cy—Ph—CF=CF—Ph—Cy—C$_9$H$_{19}$(n)
n-C$_4$H$_9$O—Cy—Ph—CF=CF—Ph—Cy—CH$_3$
n-C$_4$H$_9$O—Cy—Ph—CF=CF—Ph—Cy—C$_3$H$_7$(n)
n-C$_4$H$_9$O—Cy—Ph—CF=CF—Ph—Cy—C$_5$H$_{11}$(n)
n-C$_4$H$_9$O—Cy—Ph—CF=CF—Ph—Cy—C$_7$H$_{15}$(n)
n-C$_4$H$_9$O—Cy—Ph—CF=CF—Ph—Cy—C$_9$H$_{19}$(n)
n-C$_5$H$_{11}$O—Cy—Ph—CF=CF—Ph—Cy—CH$_3$
n-C$_5$H$_{11}$O—Cy—Ph—CF=CF—Ph—Cy—C$_3$H$_7$(n)
n-C$_5$H$_{11}$O—Cy—Ph—CF=CF—Ph—Cy—C$_5$H$_{11}$(n)
n-C$_5$H$_{11}$O—Cy—Ph—CF=CF—Ph—Cy—C$_7$H$_{15}$(n)
n-C$_5$H$_{11}$O—Cy—Ph—CF=CF—Ph—Cy—C$_9$H$_{19}$(n)
n-C$_6$H$_{13}$O—Cy—Ph—CF=CF—Ph—Cy—CH$_3$
n-C$_6$H$_{13}$O—Cy—Ph—CF=CF—Ph—Cy—C$_3$H$_7$(n)
n-C$_6$H$_{13}$O—Cy—Ph—CF=CF—Ph—Cy—C$_5$H$_{11}$(n)
n-C$_6$H$_{13}$O—Cy—Ph—CF=CF—Ph—Cy—C$_7$H$_{15}$(n)
n-C$_6$H$_{13}$O—Cy—Ph—CF=CF—Ph—Cy—C$_9$H$_{19}$(n)

n-C7H15O—Cy—Ph—CF=CF—Ph—Cy—CH3
n-C7H15O—Cy—Ph—CF=CF—Ph—Cy—C3H7(n)
n-C7H15O—Cy—Ph—CF=CF—Ph—Cy—C5H11(n)
n-C7H15O—Cy—Ph—CF=CF—Ph—Cy—C7H15(n)
n-C7H15O—Cy—Ph—CF=CF—Ph—Cy—C9H19(n)
n-C8H17O—Cy—Ph—CF=CF—Ph—Cy—CH3
n-C8H17O—Cy—Ph—CF=CF—Ph—Cy—C3H7(n)
n-C8H17O—Cy—Ph—CF=CF—Ph—Cy—C5H11(n)
n-C8H17O—Cy—Ph—CF=CF—Ph—Cy—C7H15(n)
n-C8H17O—Cy—Ph—CF=CF—Ph—Cy—C9H19(n)
n-C9H19O—Cy—Ph—CF=CF—Ph—Cy—CH3
n-C9H19O—Cy—Ph—CF=CF—Ph—Cy—C3H7(n)
n-C9H19O—Cy—Ph—CF=CF—Ph—Cy—C5H11(n)
n-C9H19O—Cy—Ph—CF=CF—Ph—Cy—C7H15(n)
n-C9H19O—Cy—Ph—CF=CF—Ph—Cy—C9H19(n)
n-C10H21O—Cy—Ph—CF=CF—Ph—Cy—CH3
n-C10H21O—Cy—Ph—CF=CF—Ph—Cy—C3H7(n)
n-C10H21O—Cy—Ph—CF=CF—Ph—Cy—C5H11(n)
n-C10H21O—Cy—Ph—CF=CF—Ph—Cy—C7H15(n)
n-C10H21O—Cy—Ph—CF=CF—Ph—Cy—C9H19(n)
CH3O—Cy—Ph—CF=CF—Ph—Cy—OCH3 n-C7H15O—Cy—Ph—CF=CF—Ph—Cy—C2H5
n-C7H15O—Cy—Ph—CF=CF—Ph—Cy—C4H9(n)
n-C7H15O—Cy—Ph—CF=CF—Ph—Cy—C6H13(n)
n-C7H15O—Cy—Ph—CF=CF—Ph—Cy—C8H17(n)
n-C7H15O—Cy—Ph—CF=CF—Ph—Cy—C10H21(n)
n-C8H17O—Cy—Ph—CF=CF—Ph—Cy—C2H5
n-C8H17O—Cy—Ph—CF=CF—Ph—Cy—C4H9(n)
n-C8H17O—Cy—Ph—CF=CF—Ph—Cy—C6H13(n)
n-C8H17O—Cy—Ph—CF=CF—Ph—Cy—C8H17(n)
n-C8H17O—Cy—Ph—CF=CF—Ph—Cy—C10H21(n)
n-C9H19O—Cy—Ph—CF=CF—Ph—Cy—C2H5
n-C9H19O—Cy—Ph—CF=CF—Ph—Cy—C4H9(n)
n-C9H19O—Cy—Ph—CF=CF—Ph—Cy—C6H13(n)
n-C9H19O—Cy—Ph—CF=CF—Ph—Cy—C8H17(n)
n-C9H19O—Cy—Ph—CF=CF—Ph—Cy—C10H21(n)
n-C10H21O—Cy—Ph—CF=CF—Ph—Cy—C2H5
n-C10H21O—Cy—Ph—CF=CF—Ph—Cy—C4H9(n)
n-C10H21O—Cy—Ph—CF=CF—Ph—Cy—C6H13(n)
n-C10H21O—Cy—Ph—CF=CF—Ph—Cy—C8H17(n)
n-C10H21O—Cy—Ph—CF=CF—Ph—Cy—C10H21(n)
CH3O—Cy—Ph—CF=CF—Ph—Cy—OC2H5

CH₃O—Cy—Ph—CF=CF—Ph—Cy—OC₃H₇(n)
CH₃O—Cy—Ph—CF=CF—Ph—Cy—OC₅H₁₁(n)
CH₃O—Cy—Ph—CF=CF—Ph—Cy—OC₇H₁₅(n)
CH₃O—Cy—Ph—CF=CF—Ph—Cy—OC₉H₁₉(n)
C₂H₅O—Cy—Ph—CF=CF—Ph—Cy—OC₂H₅
C₂H₅O—Cy—Ph—CF=CF—Ph—Cy—OC₄H₉(n)
C₂H₅O—Cy—Ph—CF=CF—Ph—Cy—OC₆H₁₃(n)
C₂H₅O—Cy—Ph—CF=CF—Ph—Cy—OC₈H₁₇(n)
C₂H₅O—Cy—Ph—CF=CF—Ph—Cy—OC₁₀H₂₁(n)
n-C₃H₇O—Cy—Ph—CF=CF—Ph—Cy—OC₃H₇(n)
n-C₃H₇O—Cy—Ph—CF=CF—Ph—Cy—OC₅H₁₁(n)
n-C₃H₇O—Cy—Ph—CF=CF—Ph—Cy—OC₇H₁₅(n)
n-C₃H₇O—Cy—Ph—CF=CF—Ph—Cy—OC₉H₁₉(n)
n-C₄H₉O—Cy—Ph—CF=CF—Ph—Cy—OC₄H₉(n)
n-C₄H₉O—Cy—Ph—CF=CF—Ph—Cy—OC₆H₁₃(n)
n-C₄H₉O—Cy—Ph—CF=CF—Ph—Cy—OC₈H₁₇(n)
n-C₄H₉O—Cy—Ph—CF=CF—Ph—Cy—OC₁₀H₂₁(n)
n-C₅H₁₁O—Cy—Ph—CF=CF—Ph—Cy—OC₅H₁₁(n)
n-C₅H₁₁O—Cy—Ph—CF=CF—Ph—Cy—OC₇H₁₅(n)
n-C₅H₁₁O—Cy—Ph—CF=CF—Ph—Cy—OC₉H₁₉(n)
n-C₆H₁₃O—Cy—Ph—CF=CF—Ph—Cy—OC₆H₁₃(n)
n-C₆H₁₃O—Cy—Ph—CF=CF—Ph—Cy—OC₈H₁₇(n)
n-C₆H₁₃O—Cy—Ph—CF=CF—Ph—Cy—OC₁₀H₂₁(n)
n-C₇H₁₅O—Cy—Ph—CF=CF—Ph—Cy—OC₇H₁₅(n)
n-C₇H₁₅O—Cy—Ph—CF=CF—Ph—Cy—OC₉H₁₉(n)
n-C₈H₁₇O—Cy—Ph—CF=CF—Ph—Cy—OC₈H₁₇(n)
n-C₈H₁₇O—Cy—Ph—CF=CF—Ph—Cy—OC₁₀H₂₁(n)
n-C₉H₁₉O—Cy—Ph—CF=CF—Ph—Cy—OC₉H₁₉(n)
n-C₁₀H₂₁O—Cy—Ph—CF=CF—Ph—Cy—OC₁₀H₂₁(n)

CH₃O—Cy—Ph—CF=CF—Ph—Cy—OC₄H₉(n)
CH₃O—Cy—Ph—CF=CF—Ph—Cy—OC₆H₁₁(n)
CH₃O—Cy—Ph—CF=CF—Ph—Cy—OC₈H₁₇(n)
CH₃O—Cy—Ph—CF=CF—Ph—Cy—OC₁₀H₂₁(n)
C₂H₅O—Cy—Ph—CF=CF—Ph—Cy—OC₃H₇(n)
C₂H₅O—Cy—Ph—CF=CF—Ph—Cy—OC₅H₁₁(n)
C₂H₅O—Cy—Ph—CF=CF—Ph—Cy—OC₇H₁₅(n)
C₂H₅O—Cy—Ph—CF=CF—Ph—Cy—OC₉H₁₉(n)
n-C₃H₇O—Cy—Ph—CF=CF—Ph—Cy—OC₄H₉(n)
n-C₃H₇O—Cy—Ph—CF=CF—Ph—Cy—OC₆H₁₃(n)
n-C₃H₇O—Cy—Ph—CF=CF—Ph—Cy—OC₅H₁₇(n)
n-C₃H₇O—Cy—Ph—CF=CF—Ph—Cy—OC₁₀H₂₁(n)
n-C₄H₉O—Cy—Ph—CF=CF—Ph—Cy—OC₅H₁₁(n)
n-C₄H₉O—Cy—Ph—CF=CF—Ph—Cy—OC₇H₁₅(n)
n-C₄H₉O—Cy—Ph—CF=CF—Ph—Cy—OC₉H₁₉(n)
n-C₅H₁₁O—Cy—Ph—CF=CF—Ph—Cy—OC₆H₁₃(n)
n-C₅H₁₁O—Cy—Ph—CF=CF—Ph—Cy—OC₈H₁₇(n)
n-C₅H₁₁O—Cy—Ph—CF=CF—Ph—Cy—OC₁₀H₂₁(n)
n-C₆H₁₃O—Cy—Ph—CF=CF—Ph—Cy—OC₇H₁₅(n)
n-C₆H₁₃O—Cy—Ph—CF=CF—Ph—Cy—OC₉H₁₉(n)
n-C₇H₁₅O—Cy—Ph—CF=CF—Ph—Cy—OC₈H₁₇(n)
n-C₇H₁₅O—Cy—Ph—CF=CF—Ph—Cy—OC₁₀H₂₁(n)
n-C₈H₁₇O—Cy—Ph—CF=CF—Ph—Cy—OC₉H₁₉(n)
n-C₉H₁₉O—Cy—Ph—CF=CF—Ph—Cy—OC₁₀H₂₁(n)

Further, the following compounds can be prepared by changing tetrafluoroethylene to tetrachloroethylene.

CH₃—Cy—Ph—CCl=CCl—Ph—Cy—CH₃
Trans-4,4'-bis-(4-methyl-trans-cyclohexyl)-α,α'-dichlorostilbene

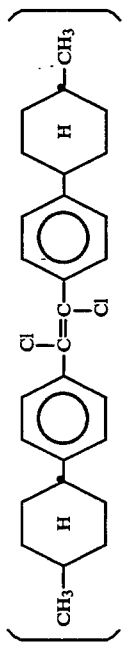

CH₃—Cy—Ph—CCl=CCl—Ph—Cy—C₂H₅
CH₃—Cy—Ph—CCl=CCl—Ph—Cy—C₃H₇(n)
CH₃—Cy—Ph—CCl=CCl—Ph—Cy—C₄H₉(n)
CH₃—Cy—Ph—CCl=CCl—Ph—Cy—C₅H₁₁(n)
CH₃—Cy—Ph—CCl=CCl—Ph—Cy—C₆H₁₃(n)
CH₃—Cy—Ph—CCl=CCl—Ph—Cy—C₇H₁₅(n)
CH₃—Cy—Ph—CCl=CCl—Ph—Cy—C₈H₁₇(n)
CH₃—Cy—Ph—CCl=CCl—Ph—Cy—C₉H₁₉(n)
C₂H₅—Cy—Ph—CCl=CCl—Ph—Cy—C₂H₅
C₂H₅—Cy—Ph—CCl=CCl—Ph—Cy—C₃H₇(n)
C₂H₅—Cy—Ph—CCl=CCl—Ph—Cy—C₄H₉(n)
C₂H₅—Cy—Ph—CCl=CCl—Ph—Cy—C₅H₁₁(n)
C₂H₅—Cy—Ph—CCl=CCl—Ph—Cy—C₆H₁₃(n)
C₂H₅—Cy—Ph—CCl=CCl—Ph—Cy—C₇H₁₅(n)
C₂H₅—Cy—Ph—CCl=CCl—Ph—Cy—C₈H₁₇(n)
C₂H₅—Cy—Ph—CCl=CCl—Ph—Cy—C₉H₁₉(n)
C₂H₅—Cy—Ph—CCl=CCl—Ph—Cy—C₁₀H₂₁(n)
n-C₃H₇—Cy—Ph—CCl=CCl—Ph—Cy—C₃H₇(n)
n-C₃H₇—Cy—Ph—CCl=CCl—Ph—Cy—C₄H₉(n)
n-C₃H₇—Cy—Ph—CCl=CCl—Ph—Cy—C₅H₁₁(n)
n-C₃H₇—Cy—ph—CCl=CCl—Ph—Cy—C₆H₁₃(n)
n-C₃H₇—Cy—Ph—CCl=CCl—Ph—Cy—C₇H₁₅(n)
n-C₃H₇—Cy—Ph—CCl=CCl—Ph—Cy—C₈H₁₇(n)
n-C₃H₇—Cy—Ph—CCl=CCl—Ph—Cy—C₉H₁₉(n)
n-C₄H₉—Cy—Ph—CCl=CCl—Ph—Cy—C₄H₉(n)
n-C₄H₉—Cy—Ph—CCl=CCl—Ph—Cy—C₅H₁₁(n)
n-C₄H₉—Cy—Ph—CCl=CCl—Ph—Cy—C₆H₁₃(n)
n-C₄H₉—Cy—Ph—CCl=CCl—Ph—Cy—C₇H₁₅(n)
n-C₄H₉—Cy—Ph—CCl=CCl—Ph—Cy—C₈H₁₇(n)
n-C₄H₉—Cy—Ph—CCl=CCl—Ph—Cy—C₉H₁₉(n)
n-C₄H₉—Cy—Ph—CCl=CCl—Ph—Cy—C₁₀H₂₁(n)
n-C₅H₁₁—Cy—Ph—CCl=CCl—Ph—Cy—C₅H₁₁(n)
n-C₅H₁₁—Cy—Ph—CCl=CCl—Ph—Cy—C₆H₁₃(n)
n-C₅H₁₁—Cy—Ph—CCl=CCl—Ph—Cy—C₇H₁₅(n)
n-C₅H₁₁—Cy—Ph—CCl=CCl—Ph—Cy—C₈H₁₇(n)
n-C₅H₁₁—Cy—Ph—CCl=CCl—Ph—Cy—C₉H₁₉(n)
n-C₅H₁₁—Cy—Ph—CCl=CCl—Ph—Cy—C₁₀H₂₁(n)
n-C₆H₁₃—Cy—Ph—CCl=CCl—Ph—Cy—C₆H₁₃(n)
n-C₆H₁₃—Cy—Ph—CCl=CCl—Ph—Cy—C₇H₁₅(n)
n-C₆H₁₃—Cy—Ph—CCl=CCl—Ph—Cy—C₈H₁₇(n)
n-C₆H₁₃—Cy—Ph—CCl=CCl—Ph—Cy—C₉H₁₉(n)
n-C₆H₁₃—Cy—Ph—CCl=CCl—Ph—Cy—C₁₀H₂₁(n)
n-C₇H₁₅—Cy—Ph—CCl=CCl—Ph—Cy—C₇H₁₅(n)
n-C₇H₁₅—Cy—Ph—CCl=CCl—Ph—Cy—C₈H₁₇(n)
n-C₇H₁₅—Cy—Ph—CCl=CCl—Ph—Cy—C₉H₁₉(n)
n-C₇H₁₅—Cy—Ph—CCl=CCl—Ph—Cy—C₁₀H₂₁(n)
n-C₈H₁₇—Cy—Ph—CCl=CCl—Ph—Cy—C₈H₁₇(n)
n-C₈H₁₇—Cy—Ph—CCl=CCl—Ph—Cy—C₉H₁₉(n)
n-C₈H₁₇—Cy—Ph—CCl=CCl—Ph—Cy—C₁₀H₂₁(n)
n-C₉H₁₉—Cy—Ph—CCl=CCl—Ph—Cy—C₉H₁₉(n)
n-C₉H₁₉—Cy—Ph—CCl=CCl—Ph—Cy—C₁₀H₂₁(n)
n-C₁₀H₂₁—Cy—Ph—CCl=CCl—Ph—Cy—C₁₀H₂₁(n)
CH₃O—Cy—Ph—CCl=CCl—Ph—Cy—CH₃
CH₃O—Cy—Ph—CCl=CCl—Ph—Cy—C₂H₅
CH₃O—Cy—Ph—CCl=CCl—Ph—Cy—C₃H₇(n)
CH₃O—Cy—Ph—CCl=CCl—Ph—Cy—C₄H₉(n)
CH₃O—Cy—Ph—CCl=CCl—Ph—Cy—C₅H₁₁(n)
CH₃O—Cy—Ph—CCl=CCl—Ph—Cy—C₆H₁₃(n)
CH₃O—Cy—Ph—CCl=CCl—Ph—Cy—C₇H₁₅(n)
CH₃O—Cy—Ph—CCl=CCl—Ph—Cy—C₈H₁₇(n)
CH₃O—Cy—Ph—CCl=CCl—Ph—Cy—C₉H₁₉(n)
CH₃O—Cy—Ph—CCl=CCl—Ph—Cy—C₁₀H₂₁(n)
C₂H₅O—Cy—Ph—CCl=CCl—Ph—Cy—CH₃
C₂H₅O—Cy—Ph—CCl=CCl—Ph—Cy—C₃H₇(n)
C₂H₅O—Cy—Ph—CCl=CCl—Ph—Cy—C₄H₉(n)
C₂H₅O—Cy—Ph—CCl=CCl—Ph—Cy—C₅H₁₁(n)
C₂H₅O—Cy—Ph—CCl=CCl—Ph—Cy—C₆H₁₃(n)
C₂H₅O—Cy—Ph—CCl=CCl—Ph—Cy—C₇H₁₅(n)
C₂H₅O—Cy—Ph—CCl=CCl—Ph—Cy—C₈H₁₇(n)
C₂H₅O—Cy—Ph—CCl=CCl—Ph—Cy—C₉H₁₉(n)
C₂H₅O—Cy—Ph—CCl=CCl—Ph—Cy—C₁₀H₂₁(n)
n-C₃H₇O—Cy—Ph—CCl=CCl—Ph—Cy—C₂H₅
n-C₃H₇O—Cy—Ph—CCl=CCl—Ph—Cy—C₄H₉(n)
n-C₃H₇O—Cy—Ph—CCl=CCl—Ph—Cy—C₅H₁₁(n)
n-C₃H₇O—Cy—Ph—CCl=CCl—Ph—Cy—C₆H₁₃(n)

-continued

| | |
|---|---|
| n-C₃H₇O—Cy—Ph—CCl=CCl—Ph—Cy—C₇H₁₅(n) | n-C₃H₇O—Cy—Ph—CCl=CCl—Ph—Cy—C₈H₁₇(n) |
| n-C₃H₇O—Cy—Ph—CCl=CCl—Ph—Cy—C₉H₁₉(n) | n-C₃H₇O—Cy—Ph—CCl=CCl—Ph—Cy—C₁₀H₂₁(n) |
| n-C₄H₉O—Cy—Ph—CCl=CCl—Ph—Cy—CH₃ | n-C₄H₉O—Cy—Ph—CCl=CCl—Ph—Cy—C₂H₅ |
| n-C₄H₉O—Cy—Ph—CCl=CCl—Ph—Cy—C₃H₇(n) | n-C₄H₉O—Cy—Ph—CCl=CCl—Ph—Cy—C₄H₉(n) |
| n-C₄H₉O—Cy—Ph—CCl=CCl—Ph—Cy—C₅H₁₁(n) | n-C₄H₉O—Cy—Ph—CCl=CCl—Ph—Cy—C₆H₁₃(n) |
| n-C₄H₉O—Cy—Ph—CCl=CCl—Ph—Cy—C₇H₁₅(n) | n-C₄H₉O—Cy—Ph—CCl=CCl—Ph—Cy—C₈H₁₇(n) |
| n-C₄H₉O—Cy—Ph—CCl=CCl—Ph—Cy—C₉H₁₉(n) | n-C₄H₉O—Cy—Ph—CCl=CCl—Ph—Cy—C₁₀H₂₁(n) |
| n-C₅H₁₁O—Cy—Ph—CCl=CCl—Ph—Cy—CH₃ | n-C₅H₁₁O—Cy—Ph—CCl=CCl—Ph—Cy—C₂H₅ |
| n-C₅H₁₁O—Cy—Ph—CCl=CCl—Ph—Cy—C₃H₇(n) | n-C₅H₁₁O—Cy—Ph—CCl=CCl—Ph—Cy—C₄H₉(n) |
| n-C₅H₁₁O—Cy—Ph—CCl=CCl—Ph—Cy—C₅H₁₁(n) | n-C₅H₁₁O—Cy—Ph—CCl=CCl—Ph—Cy—C₆H₁₃(n) |
| n-C₅H₁₁O—Cy—Ph—CCl=CCl—Ph—Cy—C₇H₁₅(n) | n-C₅H₁₁O—Cy—Ph—CCl=CCl—Ph—Cy—C₈H₁₇(n) |
| n-C₅H₁₁O—Cy—Ph—CCl=CCl—Ph—Cy—C₉H₁₉(n) | n-C₅H₁₁O—Cy—Ph—CCl=CCl—Ph—Cy—C₁₀H₂₁(n) |
| n-C₆H₁₃O—Cy—Ph—CCl=CCl—Ph—Cy—CH₃ | n-C₆H₁₃O—Cy—Ph—CCl=CCl—Ph—Cy—C₂H₅ |
| n-C₆H₁₃O—Cy—Ph—CCl=CCl—Ph—Cy—C₃H₇(n) | n-C₆H₁₃O—Cy—Ph—CCl=CCl—Ph—Cy—C₄H₉(n) |
| n-C₆H₁₃O—Cy—Ph—CCl=CCl—Ph—Cy—C₅H₁₁(n) | n-C₆H₁₃O—Cy—Ph—CCl=CCl—Ph—Cy—C₆H₁₃(n) |
| n-C₆H₁₃O—Cy—Ph—CCl=CCl—Ph—Cy—C₇H₁₅(n) | n-C₆H₁₃O—Cy—Ph—CCl=CCl—Ph—Cy—C₈H₁₇(n) |
| n-C₆H₁₃O—Cy—Ph—CCl=CCl—Ph—Cy—C₉H₁₉(n) | n-C₆H₁₃O—Cy—Ph—CCl=CCl—Ph—Cy—C₁₀H₂₁(n) |
| n-C₇H₁₅O—Cy—Ph—CCl=CCl—Ph—Cy—CH₃ | n-C₇H₁₅O—Cy—Ph—CCl=CCl—Ph—Cy—C₂H₅ |
| n-C₇H₁₅O—Cy—Ph—CCl=CCl—Ph—Cy—C₃H₇(n) | n-C₇H₁₅O—Cy—Ph—CCl=CCl—Ph—Cy—C₄H₉(n) |
| n-C₇H₁₅O—Cy—Ph—CCl=CCl—Ph—Cy—C₅H₁₁(n) | n-C₇H₁₅O—Cy—Ph—CCl=CCl—Ph—Cy—C₆H₁₃(n) |
| n-C₇H₁₅O—Cy—Ph—CCl=CCl—Ph—Cy—C₇H₁₅(n) | n-C₇H₁₅O—Cy—Ph—CCl=CCl—Ph—Cy—C₈H₁₇(n) |
| n-C₇H₁₅O—Cy—Ph—CCl=CCl—Ph—Cy—C₉H₁₉(n) | n-C₇H₁₅O—Cy—Ph—CCl=CCl—Ph—Cy—C₁₀H₂₁(n) |
| n-C₈H₁₇O—Cy—Ph—CCl=CCl—Ph—Cy—CH₃ | n-C₈H₁₇O—Cy—Ph—CCl=CCl—Ph—Cy—C₂H₅ |
| n-C₈H₁₇O—Cy—Ph—CCl=CCl—Ph—Cy—C₃H₇(n) | n-C₈H₁₇O—Cy—Ph—CCl=CCl—Ph—Cy—C₄H₉(n) |
| n-C₈H₁₇O—Cy—Ph—CCl=CCl—Ph—Cy—C₅H₁₁(n) | n-C₈H₁₇O—Cy—Ph—CCl=CCl—Ph—Cy—C₆H₁₃(n) |
| n-C₈H₁₇O—Cy—Ph—CCl=CCl—Ph—Cy—C₇H₁₅(n) | n-C₈H₁₇O—Cy—Ph—CCl=CCl—Ph—Cy—C₈H₁₇(n) |
| n-C₈H₁₇O—Cy—Ph—CCl=CCl—Ph—Cy—C₉H₁₉(n) | n-C₈H₁₇O—Cy—Ph—CCl=CCl—Ph—Cy—C₁₀H₂₁(n) |
| n-C₉H₁₉O—Cy—Ph—CCl=CCl—Ph—Cy—CH₃ | n-C₉H₁₉O—Cy—Ph—CCl=CCl—Ph—Cy—C₂H₅ |
| n-C₉H₁₉O—Cy—Ph—CCl=CCl—Ph—Cy—C₃H₇(n) | n-C₉H₁₉O—Cy—Ph—CCl=CCl—Ph—Cy—C₄H₉(n) |
| n-C₉H₁₉O—Cy—Ph—CCl=CCl—Ph—Cy—C₅H₁₁(n) | n-C₉H₁₉O—Cy—Ph—CCl=CCl—Ph—Cy—C₆H₁₃(n) | n-C9H19O—Cy—Ph—CCl=CCl—Ph—Cy—C7H15(n)
n-C9H19O—Cy—Ph—CCl=CCl—Ph—Cy—C9H19(n)
n-C10H21O—Cy—Ph—CCl=CCl—Ph—Cy—CH3
n-C10H21O—Cy—Ph—CCl=CCl—Ph—Cy—C3H7(n)
n-C10H21O—Cy—Ph—CCl=CCl—Ph—Cy—C5H11(n)
n-C10H21O—Cy—Ph—CCl=CCl—Ph—Cy—C7H15(n)
n-C10H21O—Cy—Ph—CCl=CCl—Ph—Cy—C9H19(n)
n-C10H21O—Cy—Ph—CCl=CCl—Ph—Cy—C10H21(n)
CH3O—Cy—Ph—CCl=CCl—Ph—Cy—OCH3
CH3O—Cy—Ph—CCl=CCl—Ph—Cy—OC3H7(n)
CH3O—Cy—Ph—CCl=CCl—Ph—Cy—OC5H11(n)
CH3O—Cy—Ph—CCl=CCl—Ph—Cy—OC7H15(n)
CH3O—Cy—Ph—CCl=CCl—Ph—Cy—OC9H19(n)
C2H5O—Cy—Ph—CCl=CCl—Ph—Cy—OC2H5
C2H5O—Cy—Ph—CCl=CCl—Ph—Cy—OC4H9(n)
C2H5O—Cy—Ph—CCl=CCl—Ph—Cy—OC6H13(n)
C2H5O—Cy—Ph—CCl=CCl—Ph—Cy—OC8H17(n)
C2H5O—Cy—Ph—CCl=CCl—Ph—Cy—OC10H21(n)
n-C3H7O—Cy—Ph—CCl=CCl—Ph—Cy—OC3H7(n)
n-C3H7O—Cy—Ph—CCl=CCl—Ph—Cy—OC5H11(n)
n-C3H7O—Cy—Ph—CCl=CCl—Ph—Cy—OC7H15(n)
n-C3H7O—Cy—Ph—CCl=CCl—Ph—Cy—OC9H19(n)
n-C3H7O—Cy—Ph—CCl=CCl—Ph—Cy—OC10H21(n)
n-C4H9O—Cy—Ph—CCl=CCl—Ph—Cy—OC4H9(n)
n-C4H9O—Cy—Ph—CCl=CCl—Ph—Cy—OC6H13(n)
n-C4H9O—Cy—Ph—CCl=CCl—Ph—Cy—OC8H17(n)
n-C4H9O—Cy—Ph—CCl=CCl—Ph—Cy—OC10H21(n)
n-C5H11O—Cy—Ph—CCl=CCl—Ph—Cy—OC5H11(n)
n-C5H11O—Cy—Ph—CCl=CCl—Ph—Cy—OC7H15(n)
n-C5H11O—Cy—Ph—CCl=CCl—Ph—Cy—OC9H19(n)

n-C9H19O—Cy—Ph—CCl=CCl—Ph—Cy—C8H17(n)
n-C9H19O—Cy—Ph—CCl=CCl—Ph—Cy—C10H21(n)
n-C10H21O—Cy—Ph—CCl=CCl—Ph—Cy—C2H5
n-C10H21O—Cy—Ph—CCl=CCl—Ph—Cy—C4H9(n)
n-C10H21O—Cy—Ph—CCl=CCl—Ph—Cy—C6H13(n)
n-C10H21O—Cy—Ph—CCl=CCl—Ph—Cy—C8H17(n)
CH3O—Cy—Ph—CCl=CCl—Ph—Cy—OC2H5
CH3O—Cy—Ph—CCl=CCl—Ph—Cy—OC4H9(n)
CH3O—Cy—Ph—CCl=CCl—Ph—Cy—OC6H13(n)
CH3O—Cy—Ph—CCl=CCl—Ph—Cy—OC8H17(n)
CH3O—Cy—Ph—CCl=CCl—Ph—Cy—OC10H21(n)
C2H5O—Cy—Ph—CCl=CCl—Ph—Cy—OC3H7(n)
C2H5O—Cy—Ph—CCl=CCl—Ph—Cy—OC5H11(n)
C2H5O—Cy—Ph—CCl=CCl—Ph—Cy—OC7H15(n)
C2H5O—Cy—Ph—CCl=CCl—Ph—Cy—OC9H19(n)
n-C3H7O—Cy—Ph—CCl=CCl—Ph—Cy—OC4H9(n)
n-C3H7O—Cy—Ph—CCl=CCl—Ph—Cy—OC6H13(n)
n-C3H7O—Cy—Ph—CCl=CCl—Ph—Cy—OC8H17(n)
n-C3H7O—Cy—Ph—CCl=CCl—Ph—Cy—OC10H21(n)
n-C4H9O—Cy—Ph—CCl=CCl—Ph—Cy—OC5H11(n)
n-C4H9O—Cy—Ph—CCl=CCl—Ph—Cy—OC7H15(n)
n-C4H9O—Cy—Ph—CCl=CCl—Ph—Cy—OC9H19(n)
n-C5H11O—Cy—Ph—CCl=CCl—Ph—Cy—OC6H13(n)
n-C5H11O—Cy—Ph—CCl=CCl—Ph—Cy—OC8H17(n)

The following compounds can be prepared by changing the raw material of Example 1 or Example 2:

CH₃—Cy—Ph—CF=CF—Ph—CN
Trans-4-(4-methyl-trans-cyclohexyl)-4'-cyano-α,α'-difluorostilbene

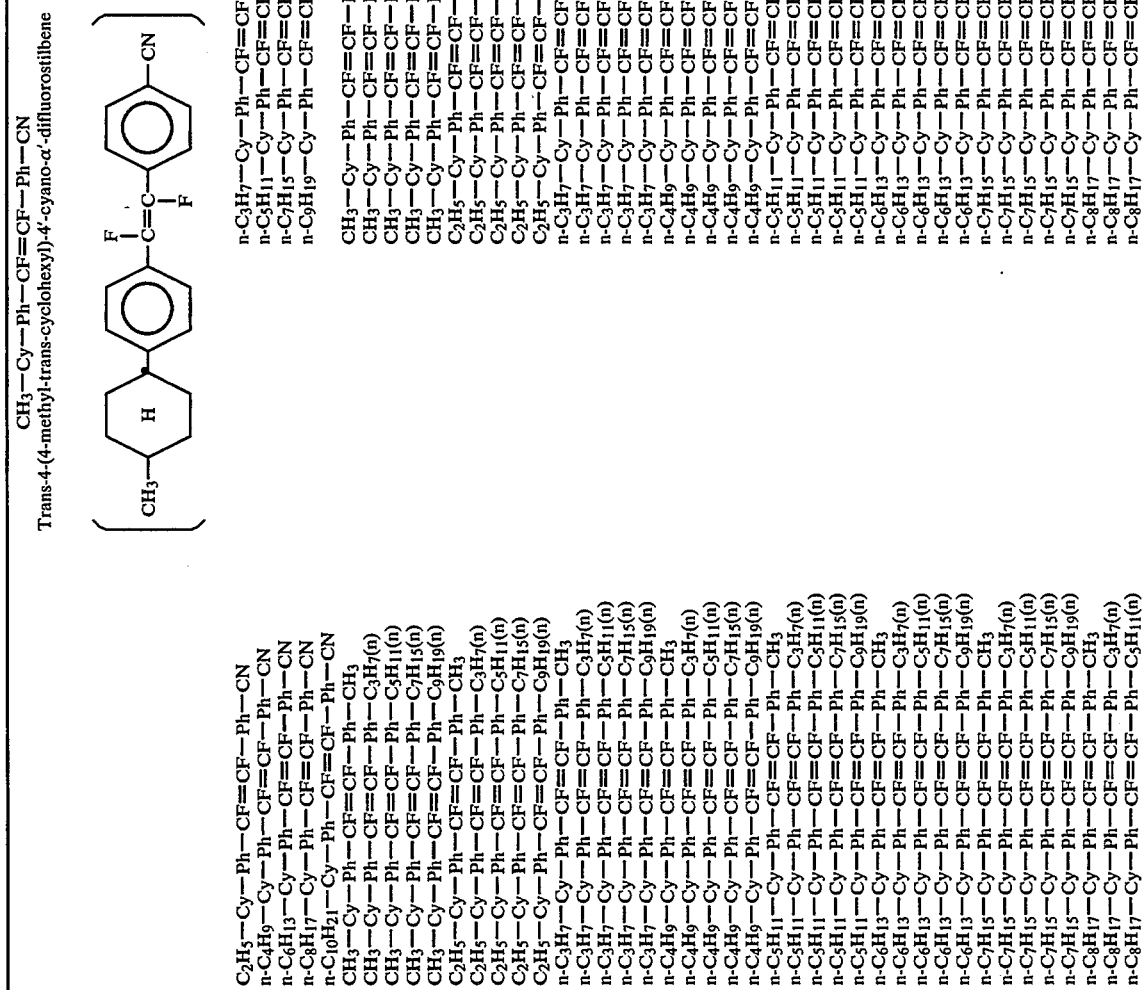

C₂H₅—Cy—Ph—CF=CF—Ph—CN
n-C₄H₉—Cy—Ph—CF=CF—Ph—CN
n-C₆H₁₃—Cy—Ph—CF=CF—Ph—CN
n-C₈H₁₇—Cy—Ph—CF=CF—Ph—CN
n-C₁₀H₂₁—Cy—Ph—CF=CF—Ph—CN
CH₃—Cy—Ph—CF=CF—Ph—CH₃
CH₃—Cy—Ph—CF=CF—Ph—C₃H₇(n)
CH₃—Cy—Ph—CF=CF—Ph—C₅H₁₁(n)
CH₃—Cy—Ph—CF=CF—Ph—C₇H₁₅(n)
CH₃—Cy—Ph—CF=CF—Ph—C₉H₁₉(n)
C₂H₅—Cy—Ph—CF=CF—Ph—CH₃
C₂H₅—Cy—Ph—CF=CF—Ph—C₃H₇(n)
C₂H₅—Cy—Ph—CF=CF—Ph—C₅H₁₁(n)
C₂H₅—Cy—Ph—CF=CF—Ph—C₇H₁₅(n)
C₂H₅—Cy—Ph—CF=CF—Ph—C₉H₁₉(n)
n-C₃H₇—Cy—Ph—CF=CF—Ph—CH₃
n-C₃H₇—Cy—Ph—CF=CF—Ph—C₃H₇(n)
n-C₃H₇—Cy—Ph—CF=CF—Ph—C₅H₁₁(n)
n-C₃H₇—Cy—Ph—CF=CF—Ph—C₇H₁₅(n)
n-C₃H₇—Cy—Ph—CF=CF—Ph—C₉H₁₉(n)
n-C₄H₉—Cy—Ph—CF=CF—Ph—CH₃
n-C₄H₉—Cy—Ph—CF=CF—Ph—C₃H₇(n)
n-C₄H₉—Cy—Ph—CF=CF—Ph—C₅H₁₁(n)
n-C₄H₉—Cy—Ph—CF=CF—Ph—C₇H₁₅(n)
n-C₄H₉—Cy—Ph—CF=CF—Ph—C₉H₁₉(n)
n-C₅H₁₁—Cy—Ph—CF=CF—Ph—CH₃
n-C₅H₁₁—Cy—Ph—CF=CF—Ph—C₃H₇(n)
n-C₅H₁₁—Cy—Ph—CF=CF—Ph—C₅H₁₁(n)
n-C₅H₁₁—Cy—Ph—CF=CF—Ph—C₇H₁₅(n)
n-C₅H₁₁—Cy—Ph—CF=CF—Ph—C₉H₁₉(n)
n-C₆H₁₃—Cy—Ph—CF=CF—Ph—CH₃
n-C₆H₁₃—Cy—Ph—CF=CF—Ph—C₃H₇(n)
n-C₆H₁₃—Cy—Ph—CF=CF—Ph—C₅H₁₁(n)
n-C₆H₁₃—Cy—Ph—CF=CF—Ph—C₇H₁₅(n)
n-C₆H₁₃—Cy—Ph—CF=CF—Ph—C₉H₁₉(n)
n-C₇H₁₅—Cy—Ph—CF=CF—Ph—CH₃
n-C₇H₁₅—Cy—Ph—CF=CF—Ph—C₃H₇(n)
n-C₇H₁₅—Cy—Ph—CF=CF—Ph—C₅H₁₁(n)
n-C₇H₁₅—Cy—Ph—CF=CF—Ph—C₇H₁₅(n)
n-C₇H₁₅—Cy—Ph—CF=CF—Ph—C₉H₁₉(n)
n-C₈H₁₇—Cy—Ph—CF=CF—Ph—CH₃
n-C₈H₁₇—Cy—Ph—CF=CF—Ph—C₃H₇(n)
n-C₈H₁₇—Cy—Ph—CF=CF—Ph—C₅H₁₁(n)

n-C₃H₇—Cy—Ph—CF=CF—Ph—CN
n-C₅H₁₁—Cy—Ph—CF=CF—Ph—CN
n-C₇H₁₅—Cy—Ph—CF=CF—Ph—CN
n-C₉H₁₉—Cy—Ph—CF=CF—Ph—CN
CH₃—Cy—Ph—CF=CF—Ph—C₂H₅
CH₃—Cy—Ph—CF=CF—Ph—C₄H₉(n)
CH₃—Cy—Ph—CF=CF—Ph—C₆H₁₃(n)
CH₃—Cy—Ph—CF=CF—Ph—C₈H₁₇(n)
CH₃—Cy—Ph—CF=CF—Ph—C₁₀H₂₁(n)
C₂H₅—Cy—Ph—CF=CF—Ph—C₂H₅
C₂H₅—Cy—Ph—CF=CF—Ph—C₄H₉(n)
C₂H₅—Cy—Ph—CF=CF—Ph—C₆H₁₃(n)
C₂H₅—Cy—Ph—CF=CF—Ph—C₈H₁₇(n)
C₂H₅—Cy—Ph—CF=CF—Ph—C₁₀H₂₁(n)
n-C₃H₇—Cy—Ph—CF=CF—Ph—C₂H₅
n-C₃H₇—Cy—Ph—CF=CF—Ph—C₄H₉(n)
n-C₃H₇—Cy—Ph—CF=CF—Ph—C₆H₁₃(n)
n-C₃H₇—Cy—Ph—CF=CF—Ph—C₈H₁₇(n)
n-C₃H₇—Cy—Ph—CF=CF—Ph—C₁₀H₂₁(n)
n-C₄H₉—Cy—Ph—CF=CF—Ph—C₂H₅
n-C₄H₉—Cy—Ph—CF=CF—Ph—C₄H₉(n)
n-C₄H₉—Cy—Ph—CF=CF—Ph—C₆H₁₃(n)
n-C₄H₉—Cy—Ph—CF=CF—Ph—C₈H₁₇(n)
n-C₄H₉—Cy—Ph—CF=CF—Ph—C₁₀H₂₁(n)
n-C₅H₁₁—Cy—Ph—CF=CF—Ph—C₂H₅
n-C₅H₁₁—Cy—Ph—CF=CF—Ph—C₄H₉(n)
n-C₅H₁₁—Cy—Ph—CF=CF—Ph—C₆H₁₃(n)
n-C₅H₁₁—Cy—Ph—CF=CF—Ph—C₈H₁₇(n)
n-C₅H₁₁—Cy—Ph—CF=CF—Ph—C₁₀H₂₁(n)
n-C₆H₁₃—Cy—Ph—CF=CF—Ph—C₂H₅
n-C₆H₁₃—Cy—Ph—CF=CF—Ph—C₄H₉(n)
n-C₆H₁₃—Cy—Ph—CF=CF—Ph—C₆H₁₃(n)
n-C₆H₁₃—Cy—Ph—CF=CF—Ph—C₈H₁₇(n)
n-C₆H₁₃—Cy—Ph—CF=CF—Ph—C₁₀H₂₁(n)
n-C₇H₁₅—Cy—Ph—CF=CF—Ph—C₂H₅
n-C₇H₁₅—Cy—Ph—CF=CF—Ph—C₄H₉(n)
n-C₇H₁₅—Cy—Ph—CF=CF—Ph—C₆H₁₃(n)
n-C₇H₁₅—Cy—Ph—CF=CF—Ph—C₈H₁₇(n)
n-C₇H₁₅—Cy—Ph—CF=CF—Ph—C₁₀H₂₁(n)
n-C₈H₁₇—Cy—Ph—CF=CF—Ph—C₂H₅
n-C₈H₁₇—Cy—Ph—CF=CF—Ph—C₄H₉(n)
n-C₈H₁₇—Cy—Ph—CF=CF—Ph—C₆H₁₃(n)

-continued

| | |
|---|---|
| n-C8H17—Cy—Ph—CF=CF—Ph—C7H15(n) | n-C8H17—Cy—Ph—CF=CF—Ph—C8H17(n) |
| n-C8H17—Cy—Ph—CF=CF—Ph—C9H19(n) | n-C8H17—Cy—Ph—CF=CF—Ph—C10H21(n) |
| n-C9H19—Cy—Ph—CF=CF—Ph—CH3 | n-C9H19—Cy—Ph—CF=CF—Ph—C2H5 |
| n-C9H19—Cy—Ph—CF=CF—Ph—C3H7(n) | n-C9H19—Cy—Ph—CF=CF—Ph—C4H9(n) |
| n-C9H19—Cy—Ph—CF=CF—Ph—C5H11(n) | n-C9H19—Cy—Ph—CF=CF—Ph—C6H13(n) |
| n-C9H19—Cy—Ph—CF=CF—Ph—C7H15(n) | n-C9H19—Cy—Ph—CF=CF—Ph—C8H17(n) |
| n-C9H19—Cy—Ph—CF=CF—Ph—C9H19(n) | n-C9H19—Cy—Ph—CF=CF—Ph—C10H21(n) |
| n-C9H19—Cy—Ph—CF=CF—Ph—CH3 | n-C9H19—Cy—Ph—CF=CF—Ph—C2H5 |
| n-C10H21—Cy—Ph—CF=CF—Ph—C3H7(n) | n-C10H21—Cy—Ph—CF=CF—Ph—C4H9(n) |
| n-C10H21—Cy—Ph—CF=CF—Ph—C5H11(n) | n-C10H21—Cy—Ph—CF=CF—Ph—C6H13(n) |
| n-C10H21—Cy—Ph—CF=CF—Ph—C7H15(n) | n-C10H21—Cy—Ph—CF=CF—Ph—C8H17(n) |
| n-C10H21—Cy—Ph—CF=CF—Ph—C9H19(n) | n-C10H21—Cy—Ph—CF=CF—Ph—C10H21(n) |
| CH3O—Cy—Ph—CF=CF—Ph—CN | C2H5O—Cy—Ph—CF=CF—Ph—CN |
| n-C3H7O—Cy—Ph—CF=CF—Ph—CN | n-C4H9O—Cy—Ph—CF=CF—Ph—CN |
| n-C5H11O—Cy—Ph—CF=CF—Ph—CN | n-C6H13O—Cy—Ph—CF=CF—Ph—CN |
| n-C7H15O—Cy—Ph—CF=CF—Ph—CN | n-C8H17O—Cy—Ph—CF=CF—Ph—CN |
| n-C9H19O—Cy—Ph—CF=CF—Ph—CN | n-C10H21O—Cy—Ph—CF=CF—Ph—CN |
| CH3O—Cy—Ph—CF=CF—Ph—CH3 | C2H5O—Cy—Ph—CF=CF—Ph—C2H5 |
| n-C3H7O—Cy—Ph—CF=CF—Ph—C3H7(n) | n-C4H9O—Cy—Ph—CF=CF—Ph—C4H9(n) |
| n-C5H11O—Cy—Ph—CF=CF—Ph—C5H11(n) | n-C6H13O—Cy—Ph—CF=CF—Ph—C6H13(n) |
| n-C7H15O—Cy—Ph—CF=CF—Ph—C7H15(n) | n-C8H17O—Cy—Ph—CF=CF—Ph—C8H17(n) |
| n-C9H19O—Cy—Ph—CF=CF—Ph—C9H19(n) | n-C10H21O—Cy—Ph—CF=CF—Ph—C10H21(n) |
| CH3O—Cy—Ph—CF=CF—Ph—OCH3 | C2H5O—Cy—Ph—CF=CF—Ph—OC2H5 |
| n-C3H7O—Cy—Ph—CF=CF—Ph—OC3H7(n) | n-C4H9O—Cy—Ph—CF=CF—Ph—OC4H9(n) |
| n-C5H11O—Cy—Ph—CF=CF—Ph—OC5H11(n) | n-C6H13O—Cy—Ph—CF=CF—Ph—OC6H13(n) |
| n-C7H15O—Cy—Ph—CF=CF—Ph—OC7H15(n) | n-C8H17O—Cy—Ph—CF=CF—Ph—OC8H17(n) |
| n-C9H19O—Cy—Ph—CF=CF—Ph—OC9H19(n) | n-C10H21O—Cy—Ph—CF=CF—Ph—OC10H21(n) |

Further, the following compounds can be prepared by changing tetrafluoroethylene to tetrachloroethylene.

CH₃—Cy—Ph—CCl=CCl—Ph—CN
Trans-4-(4-methyl-trans-cyclohexyl)'-cyano-α, α'-dichlorostilbene

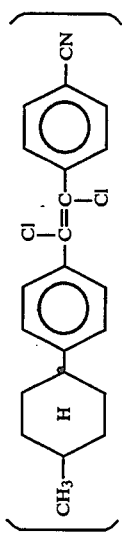

Left column:

C₂H₅—Cy—Ph—CCl=CCl—Ph—CN
n-C₄H₉—Cy—Ph—CCl=CCl—Ph—CN
n-C₆H₁₃—Cy—Ph—CCl=CCl—Ph—CN
n-C₈H₁₇—Cy—Ph—CCl=CCl—Ph—CN
n-C₁₀H₂₁—Cy—Ph—CCl=CCl—Ph—CN
CH₃—Cy—Ph—CCl=CCl—Ph—CH₃
CH₃—Cy—Ph—CCl=CCl—Ph—C₃H₇(n)
CH₃—Cy—Ph—CCl=CCl—Ph—C₅H₁₁(n)
CH₃—Cy—Ph—CCl=CCl—Ph—C₇H₁₅(n)
CH₃—Cy—Ph—CCl=CCl—Ph—C₉H₁₉(n)
C₂H₅—Cy—Ph—CCl=CCl—Ph—CH₃
C₂H₅—Cy—Ph—CCl=CCl—Ph—C₃H₇(n)
C₂H₅—Cy—Ph—CCl=CCl—Ph—C₅H₁₁(n)
C₂H₅—Cy—Ph—CCl=CCl—Ph—C₇H₁₅(n)
C₂H₅—Cy—Ph—CCl=CCl—Ph—C₉H₁₉(n)
n-C₃H₇—Cy—Ph—CCl=CCl—Ph—CH₃
n-C₃H₇—Cy—Ph—CCl=CCl—Ph—C₃H₇(n)
n-C₃H₇—Cy—Ph—CCl=CCl—Ph—C₅H₁₁(n)
n-C₃H₇—Cy—Ph—CCl=CCl—Ph—C₇H₁₅(n)
n-C₃H₇—Cy—Ph—CCl=CCl—Ph—C₉H₁₉(n)
n-C₄H₉—Cy—Ph—CCl=CCl—Ph—CH₃
n-C₄H₉—Cy—Ph—CCl=CCl—Ph—C₃H₇(n)
n-C₄H₉—Cy—Ph—CCl=CCl—Ph—C₅H₁₁(n)
n-C₄H₉—Cy—Ph—CCl=CCl—Ph—C₇H₁₅(n)
n-C₄H₉—Cy—Ph—CCl=CCl—Ph—C₉H₁₉(n)
n-C₅H₁₁—Cy—Ph—CCl=CCl—Ph—CH₃
n-C₅H₁₁—Cy—Ph—CCl=CCl—Ph—C₃H₇(n)
n-C₅H₁₁—Cy—Ph—CCl=CCl—Ph—C₅H₁₁(n)
n-C₅H₁₁—Cy—Ph—CCl=CCl—Ph—C₇H₁₅(n)
n-C₅H₁₁—Cy—Ph—CCl=CCl—Ph—C₉H₁₉(n)
n-C₆H₁₃—Cy—Ph—CCl=CCl—Ph—CH₃
n-C₆H₁₃—Cy—Ph—CCl=CCl—Ph—C₃H₇(n)
n-C₆H₁₃—Cy—Ph—CCl=CCl—Ph—C₅H₁₁(n)
n-C₆H₁₃—Cy—Ph—CCl=CCl—Ph—C₇H₁₅(n)
n-C₆H₁₃—Cy—Ph—CCl=CCl—Ph—C₉H₁₉(n)
n-C₇H₁₅—Cy—Ph—CCl=CCl—Ph—CH₃
n-C₇H₁₅—Cy—Ph—CCl=CCl—Ph—C₃H₇(n)
n-C₇H₁₅—Cy—Ph—CCl=CCl—Ph—C₅H₁₁(n)
n-C₇H₁₅—Cy—Ph—CCl=CCl—Ph—C₇H₁₅(n)
n-C₇H₁₅—Cy—Ph—CCl=CCl—Ph—C₉H₁₉(n)
n-C₈H₁₇—Cy—Ph—CCl=CCl—Ph—CH₃
n-C₈H₁₇—Cy—Ph—CCl=CCl—Ph—C₃H₇(n)
n-C₈H₁₇—Cy—Ph—CCl=CCl—Ph—C₅H₁₁(n)

Right column:

n-C₃H₇—Cy—Ph—CCl=CCl—Ph—CN
n-C₅H₁₁—Cy—Ph—CCl=CCl—Ph—CN
n-C₇H₁₅—Cy—Ph—CCl=CCl—Ph—CN
n-C₉H₁₉—Cy—Ph—CCl=CCl—Ph—CN
CH₃—Cy—Ph—CCl=CCl—Ph—C₂H₅
CH₃—Cy—Ph—CCl=CCl—Ph—C₄H₉(n)
CH₃—Cy—Ph—CCl=CCl—Ph—C₆H₁₃(n)
CH₃—Cy—Ph—CCl=CCl—Ph—C₈H₁₇(n)
CH₃—Cy—Ph—CCl=CCl—Ph—C₁₀H₂₁(n)
C₂H₅—Cy—Ph—CCl=CCl—Ph—C₂H₅
C₂H₅—Cy—Ph—CCl=CCl—Ph—C₄H₉(n)
C₂H₅—Cy—Ph—CCl=CCl—Ph—C₆H₁₃(n)
C₂H₅—Cy—Ph—CCl=CCl—Ph—C₈H₁₇(n)
C₂H₅—Cy—Ph—CCl=CCl—Ph—C₁₀H₂₁(n)
n-C₃H₇—Cy—Ph—CCl=CCl—Ph—C₂H₅
n-C₃H₇—Cy—Ph—CCl=CCl—Ph—C₄H₉(n)
n-C₃H₇—Cy—Ph—CCl=CCl—Ph—C₆H₁₃(n)
n-C₃H₇—Cy—Ph—CCl=CCl—Ph—C₈H₁₇(n)
n-C₃H₇—Cy—Ph—CCl=CCl—Ph—C₁₀H₂₁(n)
n-C₄H₉—Cy—Ph—CCl=CCl—Ph—C₂H₅
n-C₄H₉—Cy—Ph—CCl=CCl—Ph—C₄H₉(n)
n-C₄H₉—Cy—Ph—CCl=CCl—Ph—C₆H₁₃(n)
n-C₄H₉—Cy—Ph—CCl=CCl—Ph—C₈H₁₇(n)
n-C₄H₉—Cy—Ph—CCl=CCl—Ph—C₁₀H₂₁(n)
n-C₅H₁₁—Cy—Ph—CCl=CCl—Ph—C₂H₅
n-C₅H₁₁—Cy—Ph—CCl=CCl—Ph—C₄H₉(n)
n-C₅H₁₁—Cy—Ph—CCl=CCl—Ph—C₆H₁₃(n)
n-C₅H₁₁—Cy—Ph—CCl=CCl—Ph—C₈H₁₇(n)
n-C₅H₁₁—Cy—Ph—CCl=CCl—Ph—C₁₀H₂₁(n)
n-C₆H₁₃—Cy—Ph—CCl=CCl—Ph—C₂H₅
n-C₆H₁₃—Cy—Ph—CCl=CCl—Ph—C₄H₉(n)
n-C₆H₁₃—Cy—Ph—CCl=CCl—Ph—C₆H₁₃(n)
n-C₆H₁₃—Cy—Ph—CCl=CCl—Ph—C₈H₁₇(n)
n-C₆H₁₃—Cy—Ph—CCl=CCl—Ph—C₁₀H₂₁(n)
n-C₇H₁₅—Cy—Ph—CCl=CCl—Ph—C₂H₅
n-C₇H₁₅—Cy—Ph—CCl=CCl—Ph—C₄H₉(n)
n-C₇H₁₅—Cy—Ph—CCl=CCl—Ph—C₆H₁₃(n)
n-C₇H₁₅—Cy—Ph—CCl=CCl—Ph—C₈H₁₇(n)
n-C₇H₁₅—Cy—Ph—CCl=CCl—Ph—C₁₀H₂₁(n)
n-C₈H₁₇—Cy—Ph—CCl=CCl—Ph—C₂H₅
n-C₈H₁₇—Cy—Ph—CCl=CCl—Ph—C₄H₉(n)
n-C₈H₁₇—Cy—Ph—CCl=CCl—Ph—C₆H₁₃(n)

-continued n-C₈H₁₇—Cy—Ph—CCl=CCl—Ph—C₇H₁₅(n)
n-C₈H₁₇—Cy—Ph—CCl=CCl—Ph—C₉H₁₉(n)
n-C₉H₁₉—Cy—Ph—CCl=CCl—Ph—CH₃
n-C₉H₁₉—Cy—Ph—CCl=CCl—Ph—C₃H₇(n)
n-C₉H₁₉—Cy—Ph—CCl=CCl—Ph—C₅H₁₁(n)
n-C₉H₁₉—Cy—Ph—CCl=CCl—Ph—C₇H₁₅(n)
n-C₉H₁₉—Cy—Ph—CCl=CCl—Ph—C₉H₁₉(n)
n-C₉H₁₉—Cy—Ph—CCl=CCl—Ph—CH₃
n-C₁₀H₂₁—Cy—Ph—CCl=CCl—Ph—C₃H₇(n)
n-C₁₀H₂₁—Cy—Ph—CCl=CCl—Ph—C₅H₁₁(n)
n-C₁₀H₂₁—Cy—Ph—CCl=CCl—Ph—C₇H₁₅(n)
n-C₁₀H₂₁—Cy—Ph—CCl=CCl—Ph—C₉H₁₉(n)
CH₃O—Cy—Ph—CCl=CCl—Ph—CN
n-C₃H₇O—Cy—Ph—CCl=CCl—Ph—CN
n-C₅H₁₁O—Cy—Ph—CCl=CCl—Ph—CN
n-C₇H₁₅O—Cy—Ph—CCl=CCl—Ph—CN
n-C₉H₁₉O—Cy—Ph—CCl=CCl—Ph—CN
CH₃O—Cy—Ph—CCl=CCl—Ph—CH₃
n-C₃H₇O—Cy—Ph—CCl=CCl—Ph—C₃H₇(n)
n-C₅H₁₁O—Cy—Ph—CCl=CCl—Ph—C₅H₁₁(n)
n-C₇H₁₅O—Cy—Ph—CCl=CCl—Ph—C₇H₁₅(n)
n-C₉H₁₉O—Cy—Ph—CCl=CCl—Ph—C₉H₁₉(n)
CH₃O—Cy—Ph—CCl=CCl—Ph—OCH₃
n-C₃H₇O—Cy—Ph—CCl=CCl—Ph—OC₃H₇(n)
n-C₅H₁₁O—Cy—Ph—CCl=CCl—Ph—OC₅H₁₁(n)
n-C₇H₁₅O—Cy—Ph—CCl=CCl—Ph—OC₇H₁₅(n)
n-C₉H₁₉O—Cy—Ph—CCl=CCl—Ph—OC₉H₁₉(n)

n-C₈H₁₇—Cy—Ph—CCl=CCl—Ph—C₈H₁₇(n)
n-C₈H₁₇—Cy—Ph—CCl=CCl—Ph—C₁₀H₂₁(n)
n-C₉H₁₉—Cy—Ph—CCl=CCl—Ph—C₂H₅
n-C₉H₁₉—Cy—Ph—CCl=CCl—Ph—C₄H₉(n)
n-C₉H₁₉—Cy—Ph—CCl=CCl—Ph—C₆H₁₃(n)
n-C₉H₁₉—Cy—Ph—CCl=CCl—Ph—C₈H₁₇(n)
n-C₉H₁₉—Cy—Ph—CCl=CCl—Ph—C₁₀H₂₁(n)
n-C₉H₁₉—Cy—Ph—CCl=CCl—Ph—C₂H₅
n-C₁₀H₂₁—Cy—Ph—CCl=CCl—Ph—C₄H₉(n)
n-C₁₀H₂₁—Cy—Ph—CCl=CCl—Ph—C₆H₁₃(n)
n-C₁₀H₂₁—Cy—Ph—CCl=CCl—Ph—C₈H₁₇(n)
n-C₁₀H₂₁—Cy—Ph—CCl=CCl—Ph—C₁₀H₂₁(n)
C₂H₅O—Cy—Ph—CCl=CCl—Ph—CN
n-C₄H₉O—Cy—Ph—CCl=CCl—Ph—CN
n-C₆H₁₃O—Cy—Ph—CCl=CCl—Ph—CN
n-C₈H₁₇O—Cy—Ph—CCl=CCl—Ph—CN
n-C₁₀H₂₁O—Cy—Ph—CCl=CCl—Ph—CN
C₂H₅O—Cy—Ph—CCl=CCl—Ph—CH₃
n-C₄H₉O—Cy—Ph—CCl=CCl—Ph—C₄H₉(n)
n-C₆H₁₃O—Cy—Ph—CCl=CCl—Ph—C₆H₁₃(n)
n-C₈H₁₇O—Cy—Ph—CCl=CCl—Ph—C₈H₁₇(n)
n-C₁₀H₂₁O—Cy—Ph—CCl=CCl—Ph—C₁₀H₂₁(n)
C₂H₅O—Cy—Ph—CCl=CCl—Ph—OC₂H₅
n-C₄H₉O—Cy—Ph—CCl=CCl—Ph—OC₄H₉(n)
n-C₆H₁₃O—Cy—Ph—CCl=CCl—Ph—OC₆H₁₃(n)
n-C₈H₁₇O—Cy—Ph—CCl=CCl—Ph—OC₈H₁₇(n)
n-C₁₀H₂₁O—Cy—Ph—CCl=CCl—Ph—OC₁₀H₂₁(n)

The following compounds can be prepared by changing the raw material of Example 1 or Example 2. In the following formulas, Ph and PhF represent the phenylene group and the fluorine-substituted phenylene group as mentioned above.

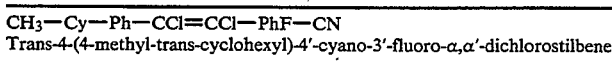
Trans-4-(4-methyl-trans-cyclohexyl)-4'-cyano-3'-fluoro-α,α'-dichlorostilbene

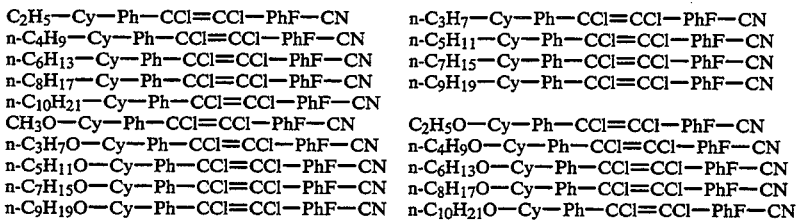

C₂H₅—Cy—Ph—CCl=CCl—PhF—CN
n-C₄H₉—Cy—Ph—CCl=CCl—PhF—CN
n-C₆H₁₃—Cy—Ph—CCl=CCl—PhF—CN
n-C₈H₁₇—Cy—Ph—CCl=CCl—PhF—CN
n-C₁₀H₂₁—Cy—Ph—CCl=CCl—PhF—CN
CH₃O—Cy—Ph—CCl=CCl—PhF—CN
n-C₃H₇O—Cy—Ph—CCl=CCl—PhF—CN
n-C₅H₁₁O—Cy—Ph—CCl=CCl—PhF—CN
n-C₇H₁₅O—Cy—Ph—CCl=CCl—PhF—CN
n-C₉H₁₉O—Cy—Ph—CCl=CCl—PhF—CN
n-C₃H₇—Cy—Ph—CCl=CCl—PhF—CN
n-C₅H₁₁—Cy—Ph—CCl=CCl—PhF—CN
n-C₇H₁₅—Cy—Ph—CCl=CCl—PhF—CN
n-C₉H₁₉—Cy—Ph—CCl=CCl—PhF—CN
C₂H₅O—Cy—Ph—CCl=CCl—PhF—CN
n-C₄H₉O—Cy—Ph—CCl=CCl—PhF—CN
n-C₆H₁₃O—Cy—Ph—CCl=CCl—PhF—CN
n-C₈H₁₇O—Cy—Ph—CCl=CCl—PhF—CN
n-C₁₀H₂₁O—Cy—Ph—CCl=CCl—PhF—CN

The following compounds can be prepared by changing the raw material of Example 1 or Example 2:

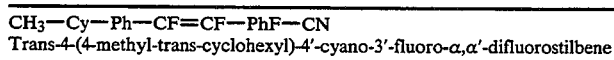
Trans-4-(4-methyl-trans-cyclohexyl)-4'-cyano-3'-fluoro-α,α'-difluorostilbene

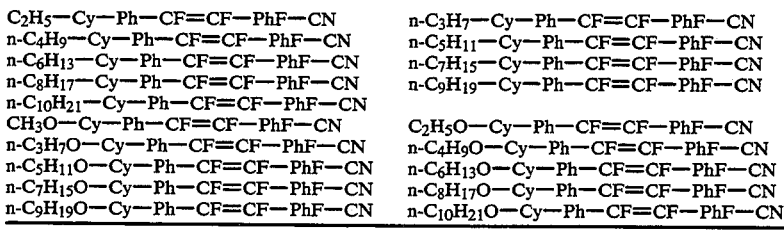

C₂H₅—Cy—Ph—CF=CF—PhF—CN
n-C₄H₉—Cy—Ph—CF=CF—PhF—CN
n-C₆H₁₃—Cy—Ph—CF=CF—PhF—CN
n-C₈H₁₇—Cy—Ph—CF=CF—PhF—CN
n-C₁₀H₂₁—Cy—Ph—CF=CF—PhF—CN
CH₃O—Cy—Ph—CF=CF—PhF—CN
n-C₃H₇O—Cy—Ph—CF=CF—PhF—CN
n-C₅H₁₁O—Cy—Ph—CF=CF—PhF—CN
n-C₇H₁₅O—Cy—Ph—CF=CF—PhF—CN
n-C₉H₁₉O—Cy—Ph—CF=CF—PhF—CN
n-C₃H₇—Cy—Ph—CF=CF—PhF—CN
n-C₅H₁₁—Cy—Ph—CF=CF—PhF—CN
n-C₇H₁₅—Cy—Ph—CF=CF—PhF—CN
n-C₉H₁₉—Cy—Ph—CF=CF—PhF—CN
C₂H₅O—Cy—Ph—CF=CF—PhF—CN
n-C₄H₉O—Cy—Ph—CF=CF—PhF—CN
n-C₆H₁₃O—Cy—Ph—CF=CF—PhF—CN
n-C₈H₁₇O—Cy—Ph—CF=CF—PhF—CN
n-C₁₀H₂₁O—Cy—Ph—CF=CF—PhF—CN

Further, the following compounds can be prepared by changing tetrafluoroethylene to tetrachloroethylene.

CH₃—Ph—Ph—Ph—CF=CF—Ph—CN
Trans-4-(4-methylphenyl)-4'-cyano-α,α'-difluorostilbene

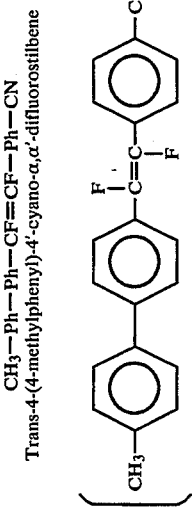

C₂H₅—Ph—Ph—Ph—CF=CF—Ph—CN
n-C₄H₉—Ph—Ph—Ph—CF=CF—Ph—CN
n-C₆H₁₃—Ph—Ph—Ph—CF=CF—Ph—CN
n-C₈H₁₇—Ph—Ph—Ph—CF=CF—Ph—CN
n-C₁₀H₂₁—Ph—Ph—Ph—CF=CF—Ph—CN
CH₃—Ph—Ph—CF=CF—Ph—CH₃
CH₃—Ph—Ph—CF=CF—Ph—C₃H₇(n)
CH₃—Ph—Ph—CF=CF—Ph—C₅H₁₁(n)
CH₃—Ph—Ph—CF=CF—Ph—C₇H₁₅(n)
CH₃—Ph—Ph—CF=CF—Ph—C₉H₁₉(n)
C₂H₅—Ph—Ph—CF=CF—Ph—CH₃
C₂H₅—Ph—Ph—CF=CF—Ph—C₃H₇(n)
C₂H₅—Ph—Ph—CF=CF—Ph—C₅H₁₁(n)
C₂H₅—Ph—Ph—CF=CF—Ph—C₇H₁₅(n)
C₂H₅—Ph—Ph—CF=CF—Ph—C₉H₁₉(n)
n-C₃H₇—Ph—Ph—CF=CF—Ph—CH₃
n-C₃H₇—Ph—Ph—CF=CF—Ph—C₃H₇(n)
n-C₃H₇—Ph—Ph—CF=CF—Ph—C₅H₁₁(n)
n-C₃H₇—Ph—Ph—CF=CF—Ph—C₇H₁₅(n)
n-C₃H₇—Ph—Ph—CF=CF—Ph—C₉H₁₉(n)
n-C₄H₉—Ph—Ph—CF=CF—Ph—CH₃
n-C₄H₉—Ph—Ph—CF=CF—Ph—C₃H₇(n)
n-C₄H₉—Ph—Ph—CF=CF—Ph—C₅H₁₁(n)
n-C₄H₉—Ph—Ph—CF=CF—Ph—C₇H₁₅(n)
n-C₄H₉—Ph—Ph—CF=CF—Ph—C₉H₁₉(n)
n-C₅H₁₁—Ph—Ph—CF=CF—Ph—CH₃
n-C₅H₁₁—Ph—Ph—CF=CF—Ph—C₃H₇(n)
n-C₅H₁₁—Ph—Ph—CF=CF—Ph—C₅H₁₁(n)
n-C₅H₁₁—Ph—Ph—CF=CF—Ph—C₇H₁₅(n)
n-C₅H₁₁—Ph—Ph—CF=CF—Ph—C₉H₁₉(n)
n-C₆H₁₃—Ph—Ph—CF=CF—Ph—CH₃
n-C₆H₁₃—Ph—Ph—CF=CF—Ph—C₃H₇(n)
n-C₆H₁₃—Ph—Ph—CF=CF—Ph—C₅H₁₁(n)
n-C₆H₁₃—Ph—Ph—CF=CF—Ph—C₇H₁₅(n)
n-C₆H₁₃—Ph—Ph—CF=CF—Ph—C₉H₁₉(n)
n-C₇H₁₅—Ph—Ph—CF=CF—Ph—CH₃
n-C₇H₁₅—Ph—Ph—CF=CF—Ph—C₃H₇(n)
n-C₇H₁₅—Ph—Ph—CF=CF—Ph—C₅H₁₁(n)
n-C₇H₁₅—Ph—Ph—CF=CF—Ph—C₇H₁₅(n)
n-C₇H₁₅—Ph—Ph—CF=CF—Ph—C₉H₁₉(n)
n-C₈H₁₇—Ph—Ph—CF=CF—Ph—CH₃
n-C₈H₁₇—Ph—Ph—CF=CF—Ph—C₃H₇(n)
n-C₈H₁₇—Ph—Ph—CF=CF—Ph—C₅H₁₁(n)

n-C₃H₇—Ph—Ph—Ph—CF=CF—Ph—CN
n-C₅H₁₁—Ph—Ph—Ph—CF=CF—Ph—CN
n-C₇H₁₅—Ph—Ph—Ph—CF=CF—Ph—CN
n-C₉H₁₉—Ph—Ph—Ph—CF=CF—Ph—CN

CH₃—Ph—Ph—Ph—CF=CF—Ph—C₂H₅
CH₃—Ph—Ph—Ph—CF=CF—Ph—C₄H₉(n)
CH₃—Ph—Ph—Ph—CF=CF—Ph—C₆H₁₃(n)
CH₃—Ph—Ph—Ph—CF=CF—Ph—C₈H₁₇(n)
CH₃—Ph—Ph—Ph—CF=CF—Ph—C₁₀H₂₁(n)
C₂H₅—Ph—Ph—Ph—CF=CF—Ph—C₂H₅
C₂H₅—Ph—Ph—Ph—CF=CF—Ph—C₄H₉(n)
C₂H₅—Ph—Ph—Ph—CF=CF—Ph—C₆H₁₃(n)
C₂H₅—Ph—Ph—Ph—CF=CF—Ph—C₈H₁₇(n)
C₂H₅—Ph—Ph—Ph—CF=CF—Ph—C₁₀H₂₁(n)
n-C₃H₇—Ph—Ph—Ph—CF=CF—Ph—C₂H₅
n-C₃H₇—Ph—Ph—Ph—CF=CF—Ph—C₄H₉(n)
n-C₃H₇—Ph—Ph—Ph—CF=CF—Ph—C₆H₁₃(n)
n-C₃H₇—Ph—Ph—Ph—CF=CF—Ph—C₈H₁₇(n)
n-C₃H₇—Ph—Ph—Ph—CF=CF—Ph—C₁₀H₂₁(n)
n-C₄H₉—Ph—Ph—Ph—CF=CF—Ph—C₂H₅
n-C₄H₉—Ph—Ph—Ph—CF=CF—Ph—C₄H₉(n)
n-C₄H₉—Ph—Ph—Ph—CF=CF—Ph—C₆H₁₃(n)
n-C₄H₉—Ph—Ph—Ph—CF=CF—Ph—C₈H₁₇(n)
n-C₄H₉—Ph—Ph—Ph—CF=CF—Ph—C₁₀H₂₁(n)
n-C₅H₁₁—Ph—Ph—Ph—CF=CF—Ph—C₂H₅
n-C₅H₁₁—Ph—Ph—Ph—CF=CF—Ph—C₄H₉(n)
n-C₅H₁₁—Ph—Ph—Ph—CF=CF—Ph—C₆H₁₃(n)
n-C₅H₁₁—Ph—Ph—Ph—CF=CF—Ph—C₈H₁₇(n)
n-C₅H₁₁—Ph—Ph—Ph—CF=CF—Ph—C₁₀H₂₁(n)
n-C₆H₁₃—Ph—Ph—Ph—CF=CF—Ph—C₂H₅
n-C₆H₁₃—Ph—Ph—Ph—CF=CF—Ph—C₄H₉(n)
n-C₆H₁₃—Ph—Ph—Ph—CF=CF—Ph—C₆H₁₃(n)
n-C₆H₁₃—Ph—Ph—Ph—CF=CF—Ph—C₈H₁₇(n)
n-C₆H₁₃—Ph—Ph—Ph—CF=CF—Ph—C₁₀H₂₁(n)
n-C₇H₁₅—Ph—Ph—Ph—CF=CF—Ph—C₂H₅
n-C₇H₁₅—Ph—Ph—Ph—CF=CF—Ph—C₄H₉(n)
n-C₇H₁₅—Ph—Ph—Ph—CF=CF—Ph—C₆H₁₃(n)
n-C₇H₁₅—Ph—Ph—Ph—CF=CF—Ph—C₈H₁₇(n)
n-C₇H₁₅—Ph—Ph—Ph—CF=CF—Ph—C₁₀H₂₁(n)
n-C₈H₁₇—Ph—Ph—Ph—CF=CF—Ph—C₂H₅
n-C₈H₁₇—Ph—Ph—Ph—CF=CF—Ph—C₄H₉(n)
n-C₈H₁₇—Ph—Ph—Ph—CF=CF—Ph—C₆H₁₃(n)

-continued n-C8H17—Ph—Ph—CF=CF—Ph—C7H15(n)
n-C8H17—Ph—Ph—CF=CF—Ph—C9H19(n)
n-C9H19—Ph—Ph—CF=CF—Ph—CH3
n-C9H19—Ph—Ph—CF=CF—Ph—C3H7(n)
n-C9H19—Ph—Ph—CF=CF—Ph—C5H11(n)
n-C9H19—Ph—Ph—CF=CF—Ph—C7H15(n)
n-C9H19—Ph—Ph—CF=CF—Ph—C9H19(n)
n-C10H21—Ph—Ph—CF=CF—Ph—CH3
n-C10H21—Ph—Ph—CF=CF—Ph—C3H7(n)
n-C10H21—Ph—Ph—CF=CF—Ph—C5H11(n)
n-C10H21—Ph—Ph—CF=CF—Ph—C7H15(n)
n-C10H21—Ph—Ph—CF=CF—Ph—C9H19(n)
CH3O—Ph—Ph—CF=CF—Ph—CN
n-C3H7O—Ph—Ph—CF=CF—Ph—CN
n-C5H11O—Ph—Ph—CF=CF—Ph—CN
n-C7H15O—Ph—Ph—CF=CF—Ph—CN
n-C9H19O—Ph—Ph—CF=CF—Ph—CN
CH3O—Ph—Ph—CF=CF—Ph—CH3
n-C3H7O—Ph—Ph—CF=CF—Ph—C3H7(n)
n-C5H11O—Ph—Ph—CF=CF—Ph—C5H11(n)
n-C7H15O—Ph—Ph—CF=CF—Ph—C7H15(n)
n-C9H19O—Ph—Ph—CF=CF—Ph—C9H19(n)
CH3O—Ph—Ph—CF=CF—Ph—OCH3
n-C3H7O—Ph—Ph—CF=CF—Ph—OC3H7(n)
n-C5H11O—Ph—Ph—CF=CF—Ph—OC5H11(n)
n-C7H15O—Ph—Ph—CF=CF—Ph—OC7H15(n)
n-C9H19O—Ph—Ph—CF=CF—Ph—OC9H19(n)

n-C8H17—Ph—Ph—CF=CF—Ph—C8H17(n)
n-C8H17—Ph—Ph—CF=CF—Ph—C10H21(n)
n-C9H19—Ph—Ph—CF=CF—Ph—C2H5
n-C9H19—Ph—Ph—CF=CF—Ph—C4H9(n)
n-C9H19—Ph—Ph—CF=CF—Ph—C6H13(n)
n-C9H19—Ph—Ph—CF=CF—Ph—C8H17(n)
n-C9H19—Ph—Ph—CF=CF—Ph—C10H21(n)
n-C10H21—Ph—Ph—CF=CF—Ph—C2H5
n-C10H21—Ph—Ph—CF=CF—Ph—C4H9(n)
n-C10H21—Ph—Ph—CF=CF—Ph—C6H13(n)
n-C10H21—Ph—Ph—CF=CF—Ph—C8H17(n)
n-C10H21—Ph—Ph—CF=CF—Ph—C10H21(n)
C2H5O—Ph—Ph—CF=CF—Ph—CN
n-C4H9O—Ph—Ph—CF=CF—Ph—CN
n-C6H13O—Ph—Ph—CF=CF—Ph—CN
n-C8H17O—Ph—Ph—CF=CF—Ph—CN
n-C10H21O—Ph—Ph—CF=CF—Ph—CN
C2H5O—Ph—Ph—CF=CF—Ph—C2H5
n-C4H9O—Ph—Ph—CF=CF—Ph—C4H9(n)
n-C6H13O—Ph—Ph—CF=CF—Ph—C6H13(n)
n-C8H17O—Ph—Ph—CF=CF—Ph—C8H17(n)
n-C10H21O—Ph—Ph—CF=CF—Ph—C10H21(n)
C2H5O—Ph—Ph—CF=CF—Ph—OC2H5
n-C4H9O—Ph—Ph—CF=CF—Ph—OC4H9(n)
n-C6H13O—Ph—Ph—CF=CF—Ph—OC6H13(n)
n-C8H17O—Ph—Ph—CF=CF—Ph—OC8H17(n)
n-C10H21O—Ph—Ph—CF=CF—Ph—OC10H21(n)

Further, the following compounds can be prepared by changing tetrafluoroethylene to tetrachloroethylene.

CH₃—Ph—Ph—CCl=CCl—Ph—CN
Trans-4-(4-methylphenyl)-4'-cyano-α,α'-dichlorostilbene

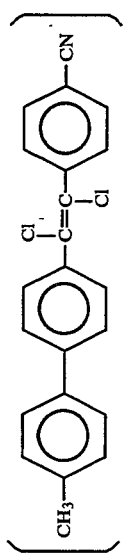

C₂H₅—Ph—Ph—CCl=CCl—Ph—CN
n-C₄H₉—Ph—Ph—CCl=CCl—Ph—CN
n-C₆H₁₃—Ph—Ph—CCl=CCl—Ph—CN
n-C₈H₁₇—Ph—Ph—CCl=CCl—Ph—CN
n-C₁₀H₂₁—Ph—Ph—CCl=CCl—Ph—CN
CH₃—Ph—Ph—CCl=CCl—Ph—CH₃
CH₃—Ph—Ph—CCl=CCl—Ph—C₃H₇(n)
CH₃—Ph—Ph—CCl=CCl—Ph—C₅H₁₁(n)
CH₃—Ph—Ph—CCl=CCl—Ph—C₇H₁₅(n)
CH₃—Ph—Ph—CCl=CCl—Ph—C₉H₁₉(n)
C₂H₅—Ph—Ph—CCl=CCl—Ph—CH₃
C₂H₅—Ph—Ph—CCl=CCl—Ph—C₃H₇(n)
C₂H₅—Ph—Ph—CCl=CCl—Ph—C₅H₁₁(n)
C₂H₅—Ph—Ph—CCl=CCl—Ph—C₇H₁₅(n)
C₂H₅—Ph—Ph—CCl=CCl—Ph—C₉H₁₉(n)
n-C₃H₇—Ph—Ph—CCl=CCl—Ph—CH₃
n-C₃H₇—Ph—Ph—CCl=CCl—Ph—C₃H₇(n)
n-C₃H₇—Ph—Ph—CCl=CCl—Ph—C₅H₁₁(n)
n-C₃H₇—Ph—Ph—CCl=CCl—Ph—C₇H₁₅(n)
n-C₃H₇—Ph—Ph—CCl=CCl—Ph—C₉H₁₉(n)
n-C₄H₉—Ph—Ph—CCl=CCl—Ph—CH₃
n-C₄H₉—Ph—Ph—CCl=CCl—Ph—C₃H₇(n)
n-C₄H₉—Ph—Ph—CCl=CCl—Ph—C₅H₁₁(n)
n-C₄H₉—Ph—Ph—CCl=CCl—Ph—C₇H₁₅(n)
n-C₄H₉—Ph—Ph—CCl=CCl—Ph—C₉H₁₉(n)
n-C₅H₁₁—Ph—Ph—CCl=CCl—Ph—CH₃
n-C₅H₁₁—Ph—Ph—CCl=CCl—Ph—C₃H₇(n)
n-C₅H₁₁—Ph—Ph—CCl=CCl—Ph—C₅H₁₁(n)
n-C₅H₁₁—Ph—Ph—CCl=CCl—Ph—C₇H₁₅(n)
n-C₅H₁₁—Ph—Ph—CCl=CCl—Ph—C₉H₁₉(n)
n-C₆H₁₃—Ph—Ph—CCl=CCl—Ph—CH₃
n-C₆H₁₃—Ph—Ph—CCl=CCl—Ph—C₃H₇(n)
n-C₆H₁₃—Ph—Ph—CCl=CCl—Ph—C₅H₁₁(n)
n-C₆H₁₃—Ph—Ph—CCl=CCl—Ph—C₇H₁₅(n)
n-C₆H₁₃—Ph—Ph—CCl=CCl—Ph—C₉H₁₉(n)
n-C₇H₁₅—Ph—Ph—CCl=CCl—Ph—CH₃
n-C₇H₁₅—Ph—Ph—CCl=CCl—Ph—C₃H₇(n)
n-C₇H₁₅—Ph—Ph—CCl=CCl—Ph—C₅H₁₁(n)
n-C₇H₁₅—Ph—Ph—CCl=CCl—Ph—C₇H₁₅(n)
n-C₇H₁₅—Ph—Ph—CCl=CCl—Ph—C₉H₁₉(n)
n-C₈H₁₇—Ph—Ph—CCl=CCl—Ph—CH₃
n-C₈H₁₇—Ph—Ph—CCl=CCl—Ph—C₃H₇(n)
n-C₈H₁₇—Ph—Ph—CCl=CCl—Ph—C₅H₁₁(n)

n-C₃H₇—Ph—Ph—CCl=CCl—Ph—CN
n-C₅H₁₁—Ph—Ph—CCl=CCl—Ph—CN
n-C₇H₁₅—Ph—Ph—CCl=CCl—Ph—CN
n-C₉H₁₉—Ph—Ph—CCl=CCl—Ph—CN
CH₃—Ph—Ph—CCl=CCl—Ph—C₂H₅
CH₃—Ph—Ph—CCl=CCl—Ph—C₄H₉(n)
CH₃—Ph—Ph—CCl=CCl—Ph—C₆H₁₃(n)
CH₃—Ph—Ph—CCl=CCl—Ph—C₈H₁₇(n)
CH₃—Ph—Ph—CCl=CCl—Ph—C₁₀H₂₁(n)
C₂H₅—Ph—Ph—CCl=CCl—Ph—C₂H₅
C₂H₅—Ph—Ph—CCl=CCl—Ph—C₄H₉(n)
C₂H₅—Ph—Ph—CCl=CCl—Ph—C₆H₁₃(n)
C₂H₅—Ph—Ph—CCl=CCl—Ph—C₈H₁₇(n)
C₂H₅—Ph—Ph—CCl=CCl—Ph—C₁₀H₂₁(n)
n-C₃H₇—Ph—Ph—CCl=CCl—Ph—C₂H₅
n-C₃H₇—Ph—Ph—CCl=CCl—Ph—C₄H₉(n)
n-C₃H₇—Ph—Ph—CCl=CCl—Ph—C₆H₁₃(n)
n-C₃H₇—Ph—Ph—CCl=CCl—Ph—C₈H₁₇(n)
n-C₃H₇—Ph—Ph—CCl=CCl—Ph—C₁₀H₂₁(n)
n-C₄H₉—Ph—Ph—CCl=CCl—Ph—C₂H₅
n-C₄H₉—Ph—Ph—CCl=CCl—Ph—C₄H₉(n)
n-C₄H₉—Ph—Ph—CCl=CCl—Ph—C₆H₁₃(n)
n-C₄H₉—Ph—Ph—CCl=CCl—Ph—C₈H₁₇(n)
n-C₄H₉—Ph—Ph—CCl=CCl—Ph—C₁₀H₂₁(n)
n-C₅H₁₁—Ph—Ph—CCl=CCl—Ph—C₂H₅
n-C₅H₁₁—Ph—Ph—CCl=CCl—Ph—C₄H₉(n)
n-C₅H₁₁—Ph—Ph—CCl=CCl—Ph—C₆H₁₃(n)
n-C₅H₁₁—Ph—Ph—CCl=CCl—Ph—C₈H₁₇(n)
n-C₅H₁₁—Ph—Ph—CCl=CCl—Ph—C₁₀H₂₁(n)
n-C₆H₁₃—Ph—Ph—CCl=CCl—Ph—C₂H₅
n-C₆H₁₃—Ph—Ph—CCl=CCl—Ph—C₄H₉(n)
n-C₆H₁₃—Ph—Ph—CCl=CCl—Ph—C₆H₁₃(n)
n-C₆H₁₃—Ph—Ph—CCl=CCl—Ph—C₈H₁₇(n)
n-C₆H₁₃—Ph—Ph—CCl=CCl—Ph—C₁₀H₂₁(n)
n-C₇H₁₅—Ph—Ph—CCl=CCl—Ph—C₂H₅
n-C₇H₁₅—Ph—Ph—CCl=CCl—Ph—C₄H₉(n)
n-C₇H₁₅—Ph—Ph—CCl=CCl—Ph—C₆H₁₃(n)
n-C₇H₁₅—Ph—Ph—CCl=CCl—Ph—C₈H₁₇(n)
n-C₇H₁₅—Ph—Ph—CCl=CCl—Ph—C₁₀H₂₁(n)
n-C₈H₁₇—Ph—Ph—CCl=CCl—Ph—C₂H₅
n-C₈H₁₇—Ph—Ph—CCl=CCl—Ph—C₄H₉(n)
n-C₈H₁₇—Ph—Ph—CCl=CCl—Ph—C₆H₁₃(n)

-continued

| | |
|---|---|
| n-C8H17—Ph—Ph—CCl=CCl—Ph—C7H15(n) | n-C8H17—Ph—Ph—CCl=CCl—Ph—C8H17(n) |
| n-C8H17—Ph—Ph—CCl=CCl—Ph—C9H19(n) | n-C8H17—Ph—Ph—CCl=CCl—Ph—C10H21(n) |
| n-C9H19—Ph—Ph—CCl=CCl—Ph—CH3 | n-C9H19—Ph—Ph—CCl=CCl—Ph—C2H5 |
| n-C9H19—Ph—Ph—CCl=CCl—Ph—C3H7(n) | n-C9H19—Ph—Ph—CCl=CCl—Ph—C4H9(n) |
| n-C9H19—Ph—Ph—CCl=CCl—Ph—C5H11(n) | n-C9H19—Ph—Ph—CCl=CCl—Ph—C6H13(n) |
| n-C9H19—Ph—Ph—CCl=CCl—Ph—C7H15(n) | n-C9H19—Ph—Ph—CCl=CCl—Ph—C8H17(n) |
| n-C9H19—Ph—Ph—CCl=CCl—Ph—C9H19(n) | n-C9H19—Ph—Ph—CCl=CCl—Ph—C10H21(n) |
| n-C10H21—Ph—Ph—CCl=CCl—Ph—CH3 | n-C10H21—Ph—Ph—CCl=CCl—Ph—C2H5 |
| n-C10H21—Ph—Ph—CCl=CCl—Ph—C3H7(n) | n-C10H21—Ph—Ph—CCl=CCl—Ph—C4H9(n) |
| n-C10H21—Ph—Ph—CCl=CCl—Ph—C5H11(n) | n-C10H21—Ph—Ph—CCl=CCl—Ph—C6H13(n) |
| n-C10H21—Ph—Ph—CCl=CCl—Ph—C7H15(n) | n-C10H21—Ph—Ph—CCl=CCl—Ph—C8H17(n) |
| n-C10H21—Ph—Ph—CCl=CCl—Ph—C9H19(n) | n-C10H21—Ph—Ph—CCl=CCl—Ph—C10H21(n) |
| CH3O—Ph—Ph—CCl=CCl—Ph—CN | C2H5O—Ph—Ph—CCl=CCl—Ph—CN |
| n-C3H7O—Ph—Ph—CCl=CCl—Ph—CN | n-C4H9O—Ph—Ph—CCl=CCl—Ph—CN |
| n-C5H11O—Ph—Ph—CCl=CCl—Ph—CN | n-C6H13O—Ph—Ph—CCl=CCl—Ph—CN |
| n-C7H15O—Ph—Ph—CCl=CCl—Ph—CN | n-C8H17O—Ph—Ph—CCl=CCl—Ph—CN |
| n-C9H19O—Ph—Ph—CCl=CCl—Ph—CN | n-C10H21O—Ph—Ph—CCl=CCl—Ph—CN |
| CH3O—Ph—Ph—CCl=CCl—Ph—CH3 | C2H5O—Ph—Ph—CCl=CCl—Ph—C2H5 |
| n-C3H7O—Ph—Ph—CCl=CCl—Ph—C3H7(n) | n-C4H9O—Ph—Ph—CCl=CCl—Ph—C4H9(n) |
| n-C5H11O—Ph—Ph—CCl=CCl—Ph—C5H11(n) | n-C6H13O—Ph—Ph—CCl=CCl—Ph—C6H13(n) |
| n-C7H15O—Ph—Ph—CCl=CCl—Ph—C7H15(n) | n-C8H17O—Ph—Ph—CCl=CCl—Ph—C8H17(n) |
| n-C9H19O—Ph—Ph—CCl=CCl—Ph—C9H19(n) | n-C10H21O—Ph—Ph—CCl=CCl—Ph—C10H21(n) |
| CH3O—Ph—Ph—CCl=CCl—Ph—OCH3 | C2H5O—Ph—Ph—CCl=CCl—Ph—OC2H5 |
| n-C3H7O—Ph—Ph—CCl=CCl—Ph—OC3H7(n) | n-C4H9O—Ph—Ph—CCl=CCl—Ph—OC4H9(n) |
| n-C5H11O—Ph—Ph—CCl=CCl—Ph—OC5H11(n) | n-C6H13O—Ph—Ph—CCl=CCl—Ph—OC6H13(n) |
| n-C7H15O—Ph—Ph—CCl=CCl—Ph—OC7H15(n) | n-C8H17O—Ph—Ph—CCl=CCl—Ph—OC8H17(n) |
| n-C9H19O—Ph—Ph—CCl=CCl—Ph—OC9H19(n) | n-C10H21O—Ph—Ph—CCl=CCl—Ph—OC10H21(n) |

The following compounds can be prepared by changing the raw material of Example 1 or Example 2:

by changing tetrafluoroethylene to tetrachloroethylene.

---

CH₃—Ph—Ph—CF=CF—PhF—CN
Trans-4-(4-methylphenyl)-4'-cyano-3'-fluoro-α,α'-difluorostilbene

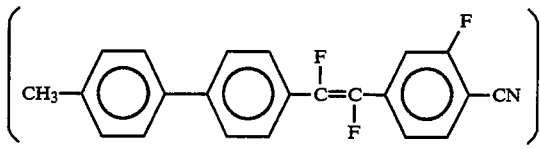

| | |
|---|---|
| C₂H₅—Ph—Ph—CF=CF—PhF—CN | n-C₃H₇—Ph—Ph—CF=CF—PhF—CN |
| n-C₄H₉—Ph—Ph—CF=CF—PhF—CN | n-C₅H₁₁—Ph—Ph—CF=CF—PhF—CN |
| n-C₆H₁₃—Ph—Ph—CF=CF—PhF—CN | n-C₇H₁₅—Ph—Ph—CF=CF—PhF—CN |
| n-C₈H₁₇—Ph—Ph—CF=CF—PhF—CN | n-C₉H₁₉—Ph—Ph—CF=CF—PhF—CN |
| n-C₁₀H₂₁—Ph—Ph—CF=CF—PhF—CN | |
| CH₃O—Ph—Ph—CF=CF—PhF—CN | C₂H₅O—Ph—Ph—CF=CF—PhF—CN |
| n-C₃H₇O—Ph—Ph—CF=CF—PhF—CN | n-C₄H₉O—Ph—Ph—CF=CF—PhF—CN |
| n-C₅H₁₁O—Ph—Ph—CF=CF—PhF—CN | n-C₆H₁₃O—Ph—Ph—CF=CF—PhF—CN |
| n-C₇H₁₅O—Ph—Ph—CF=CF—PhF—CN | n-C₈H₁₇O—Ph—Ph—CF=CF—PhF—CN |
| n-C₉H₁₉O—Ph—Ph—CF=CF—PhF—CN | n-C₁₀H₂₁O—Ph—Ph—CF=CF—PhF—CN |

---

CH₃—Ph—Ph—CCl=CCl—PhF—CN
Trans-4-(4-methylphenyl)-4'-cyano-3'-fluoro-α,α'-dichlorostilbene

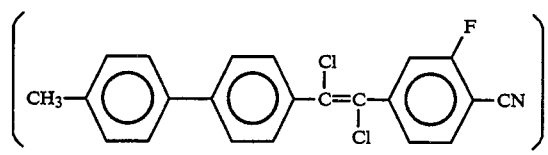

| | |
|---|---|
| C₂H₅—Ph—Ph—CCl=CCl—PhF—CN | n-C₃H₇—Ph—Ph—CCl=CCl—PhF—CN |
| n-C₄H₉—Ph—Ph—CCl=CCl—PhF—CN | n-C₅H₁₁—Ph—Ph—CCl=CCl—PhF—CN |
| n-C₆H₁₃—Ph—Ph—CCl=CCl—PhF—CN | n-C₇H₁₅—Ph—Ph—CCl=CCl—PhF—CN |
| n-C₈H₁₇—Ph—Ph—CCl=CCl—PhF—CN | n-C₉H₁₉—Ph—Ph—CCl=CCl—PhF—CN |
| n-C₁₀H₂₁—Ph—Ph—CCl=CCl—PhF—CN | |
| CH₃O—Ph—Ph—CCl=CCl—PhF—CN | C₂H₅O—Ph—Ph—CCl=CCl—PhF—CN |
| n-C₃H₇O—Ph—Ph—CCl=CCl—PhF—CN | n-C₄H₉O—Ph—Ph—CCl=CCl—PhF—CN |
| n-C₅H₁₁O—Ph—Ph—CCl=CCl—PhF—CN | n-C₆H₁₃O—Ph—Ph—CCl=CCl—PhF—CN |
| n-C₇H₁₅O—Ph—Ph—CCl=CCl—PhF—CN | n-C₈H₁₇O—Ph—Ph—CCl=CCl—PhF—CN |
| n-C₉H₁₉O—Ph—Ph—CCl=CCl—PhF—CN | n-C₁₀H₂₁O—Ph—Ph—CCl=CCl—PhF—CN |

---

Further, the following compounds can be prepared

The following compounds can be prepared by changing the raw material of Example 1 or Example 2:

CH₃—Cy—CH₂CH₂—Ph—CF=CF—Ph—CN
Trans-4-[2-(4-methyl-trans-cyclohexyl)ethyl]-4'-cyano-α,α'-difluorostilbene

[Structure: cyclohexyl ring with CH₃ and CH₂CH₂ substituents, connected to phenyl-C(F)=C(F)-phenyl-CN]

C₂H₅—Cy—CH₂CH₂—Ph—CF=CF—Ph—CN
n-C₄H₉—Cy—CH₂CH₂—Ph—CF=CF—Ph—CN
n-C₆H₁₃—Cy—CH₂CH₂—Ph—CF=CF—Ph—CN
n-C₈H₁₇—Cy—CH₂CH₂—Ph—CF=CF—Ph—CN
n-C₁₀H₂₁—Cy—CH₂CH₂—Ph—CF=CF—Ph—CN
CH₃—Cy—CH₂CH₂—Ph—CF=CF—Ph—CH₃
CH₃—Cy—CH₂CH₂—Ph—CF=CF—Ph—C₃H₇(n)
CH₃—Cy—CH₂CH₂—Ph—CF=CF—Ph—C₅H₁₁(n)
CH₃—Cy—CH₂CH₂—Ph—CF=CF—Ph—C₇H₁₅(n)
CH₃—Cy—CH₂CH₂—Ph—CF=CF—Ph—C₉H₁₉(n)
C₂H₅—Cy—CH₂CH₂—Ph—CF=CF—Ph—CH₃
C₂H₅—Cy—CH₂CH₂—Ph—CF=CF—Ph—C₃H₇(n)
C₂H₅—Cy—CH₂CH₂—Ph—CF=CF—Ph—C₅H₁₁(n)
C₂H₅—Cy—CH₂CH₂—Ph—CF=CF—Ph—C₇H₁₅(n)
C₂H₅—Cy—CH₂CH₂—Ph—CF=CF—Ph—C₉H₁₉(n)
n-C₃H₇—Cy—CH₂CH₂—Ph—CF=CF—Ph—CH₃
n-C₃H₇—Cy—CH₂CH₂—Ph—CF=CF—Ph—C₃H₇(n)
n-C₃H₇—Cy—CH₂CH₂—Ph—CF=CF—Ph—C₅H₁₁(n)
n-C₃H₇—Cy—CH₂CH₂—Ph—CF=CF—Ph—C₇H₁₅(n)
n-C₃H₇—Cy—CH₂CH₂—Ph—CF=CF—Ph—C₉H₁₉(n)
n-C₄H₉—Cy—CH₂CH₂—Ph—CF=CF—Ph—CH₃
n-C₄H₉—Cy—CH₂CH₂—Ph—CF=CF—Ph—C₃H₇(n)
n-C₄H₉—Cy—CH₂CH₂—Ph—CF=CF—Ph—C₅H₁₁(n)
n-C₄H₉—Cy—CH₂CH₂—Ph—CF=CF—Ph—C₇H₁₅(n)
n-C₄H₉—Cy—CH₂CH₂—Ph—CF=CF—Ph—C₉H₁₉(n)
n-C₅H₁₁—Cy—CH₂CH₂—Ph—CF=CF—Ph—CH₃
n-C₅H₁₁—Cy—CH₂CH₂—Ph—CF=CF—Ph—C₃H₇(n)
n-C₅H₁₁—Cy—CH₂CH₂—Ph—CF=CF—Ph—C₅H₁₁(n)
n-C₅H₁₁—Cy—CH₂CH₂—Ph—CF=CF—Ph—C₇H₁₅(n)
n-C₅H₁₁—Cy—CH₂CH₂—Ph—CF=CF—Ph—C₉H₁₉(n)
n-C₆H₁₃—Cy—CH₂CH₂—Ph—CF=CF—Ph—CH₃
n-C₆H₁₃—Cy—CH₂CH₂—Ph—CF=CF—Ph—C₃H₇(n)
n-C₆H₁₃—Cy—CH₂CH₂—Ph—CF=CF—Ph—C₅H₁₁(n)
n-C₆H₁₃—Cy—CH₂CH₂—Ph—CF=CF—Ph—C₇H₁₅(n)
n-C₆H₁₃—Cy—CH₂CH₂—Ph—CF=CF—Ph—C₉H₁₉(n)
n-C₆H₁₃—Cy—CH₂CH₂—Ph—CF=CF—Ph—C₁₀H₂₁(n)
n-C₇H₁₅—Cy—CH₂CH₂—Ph—CF=CF—Ph—CH₃
n-C₇H₁₅—Cy—CH₂CH₂—Ph—CF=CF—Ph—C₂H₅ n-C₃H₇—Cy—CH₂CH₂—Ph—CF=CF—Ph—CN
n-C₅H₁₁—Cy—CH₂CH₂—Ph—CF=CF—Ph—CN
n-C₇H₁₅—Cy—CH₂CH₂—Ph—CF=CF—Ph—CN
n-C₉H₁₉—Cy—CH₂CH₂—Ph—CF=CF—Ph—CN
CH₃—Cy—CH₂CH₂—Ph—CF=CF—Ph—C₂H₅
CH₃—Cy—CH₂CH₂—Ph—CF=CF—Ph—C₄H₉(n)
CH₃—Cy—CH₂CH₂—Ph—CF=CF—Ph—C₆H₁₃(n)
CH₃—Cy—CH₂CH₂—Ph—CF=CF—Ph—C₈H₁₇(n)
CH₃—Cy—CH₂CH₂—Ph—CF=CF—Ph—C₁₀H₂₁(n)
C₂H₅—Cy—CH₂CH₂—Ph—CF=CF—Ph—C₂H₅
C₂H₅—Cy—CH₂CH₂—Ph—CF=CF—Ph—C₄H₉(n)
C₂H₅—Cy—CH₂CH₂—Ph—CF=CF—Ph—C₆H₁₃(n)
C₂H₅—Cy—CH₂CH₂—Ph—CF=CF—Ph—C₈H₁₇(n)
C₂H₅—Cy—CH₂CH₂—Ph—CF=CF—Ph—C₁₀H₂₁(n)
n-C₃H₇—Cy—CH₂CH₂—Ph—CF=CF—Ph—C₂H₅
n-C₃H₇—Cy—CH₂CH₂—Ph—CF=CF—Ph—C₄H₉(n)
n-C₃H₇—Cy—CH₂CH₂—Ph—CF=CF—Ph—C₆H₁₃(n)
n-C₃H₇—Cy—CH₂CH₂—Ph—CF=CF—Ph—C₈H₁₇(n)
n-C₃H₇—Cy—CH₂CH₂—Ph—CF=CF—Ph—C₁₀H₂₁(n)
n-C₄H₉—Cy—CH₂CH₂—Ph—CF=CF—Ph—C₂H₅
n-C₄H₉—Cy—CH₂CH₂—Ph—CF=CF—Ph—C₄H₉(n)
n-C₄H₉—Cy—CH₂CH₂—Ph—CF=CF—Ph—C₆H₁₃(n)
n-C₄H₉—Cy—CH₂CH₂—Ph—CF=CF—Ph—C₈H₁₇(n)
n-C₄H₉—Cy—CH₂CH₂—Ph—CF=CF—Ph—C₁₀H₂₁(n)
n-C₅H₁₁—Cy—CH₂CH₂—Ph—CF=CF—Ph—C₂H₅
n-C₅H₁₁—Cy—CH₂CH₂—Ph—CF=CF—Ph—C₄H₉(n)
n-C₅H₁₁—Cy—CH₂CH₂—Ph—CF=CF—Ph—C₆H₁₃(n)
n-C₅H₁₁—Cy—CH₂CH₂—Ph—CF=CF—Ph—C₈H₁₇(n)
n-C₅H₁₁—Cy—CH₂CH₂—Ph—CF=CF—Ph—C₁₀H₂₁(n)
n-C₆H₁₃—Cy—CH₂CH₂—Ph—CF=CF—Ph—C₂H₅
n-C₆H₁₃—Cy—CH₂CH₂—Ph—CF=CF—Ph—C₄H₉(n)
n-C₆H₁₃—Cy—CH₂CH₂—Ph—CF=CF—Ph—C₆H₁₃(n)
n-C₆H₁₃—Cy—CH₂CH₂—Ph—CF=CF—Ph—C₈H₁₇(n)

n-C₇H₁₅—Cy—CH₂CH₂—Ph—CF=CF—Ph—C₃H₇(n)

n-C₇H₁₅—Cy—CH₂CH₂—Ph—CF=CF—Ph—C₅H₁₁(n)
n-C₇H₁₅—Cy—CH₂CH₂—Ph—CF=CF—Ph—C₇H₁₅(n)
n-C₇H₁₅—Cy—CH₂CH₂—Ph—CF=CF—Ph—C₉H₁₉(n)

n-C₈H₁₇—Cy—CH₂CH₂—Ph—CF=CF—Ph—C₂H₅
n-C₈H₁₇—Cy—CH₂CH₂—Ph—CF=CF—Ph—C₄H₉(n)
n-C₈H₁₇—Cy—CH₂CH₂—Ph—CF=CF—Ph—C₆H₁₃(n)
n-C₈H₁₇—Cy—CH₂CH₂—Ph—CF=CF—Ph—C₈H₁₇(n)

n-C₉H₁₉—Cy—CH₂CH₂—Ph—CF=CF—Ph—C₂H₅
n-C₉H₁₉—Cy—CH₂CH₂—Ph—CF=CF—Ph—C₄H₉(n)
n-C₉H₁₉—Cy—CH₂CH₂—Ph—CF=CF—Ph—C₆H₁₃(n)
n-C₉H₁₉—Cy—CH₂CH₂—Ph—CF=CF—Ph—C₈H₁₇(n)

n-C₁₀H₂₁—Cy—CH₂CH₂—Ph—CF=CF—Ph—C₂H₅
n-C₁₀H₂₁—Cy—CH₂CH₂—Ph—CF=CF—Ph—C₄H₉(n)

C₂H₅O—Cy—CH₂CH₂—Ph—CF=CF—Ph—CN
n-C₄H₉O—Cy—CH₂CH₂—Ph—CF=CF—Ph—CN
n-C₆H₁₃O—Cy—CH₂CH₂—Ph—CF=CF—Ph—CN
n-C₈H₁₇O—Cy—CH₂CH₂—Ph—CF=CF—Ph—CN
n-C₁₀H₂₁O—Cy—CH₂CH₂—Ph—CF=CF—Ph—CN
C₂H₅O—Cy—CH₂CH₂—Ph—CF=CF—Ph—C₂H₅
n-C₄H₉O—Cy—CH₂CH₂—Ph—CF=CF—Ph—C₄H₉(n)

n-C₇H₁₅—Cy—CH₂CH₂—Ph—CF=CF—Ph—C₄H₉(n)
n-C₇H₁₅—Cy—CH₂CH₂—Ph—CF=CF—Ph—C₆H₁₃(n)
n-C₇H₁₅—Cy—CH₂CH₂—Ph—CF=CF—Ph—C₈H₁₇(n)
n-C₇H₁₅—Cy—CH₂CH₂—Ph—CF=CF—Ph—C₁₀H₂₁(n)

n-C₈H₁₇—Cy—CH₂CH₂—Ph—CF=CF—Ph—CH₃
n-C₈H₁₇—Cy—CH₂CH₂—Ph—CF=CF—Ph—C₃H₇(n)
n-C₈H₁₇—Cy—CH₂CH₂—Ph—CF=CF—Ph—C₅H₁₁(n)
n-C₈H₁₇—Cy—CH₂CH₂—Ph—CF=CF—Ph—C₇H₁₅(n)
n-C₈H₁₇—Cy—CH₂CH₂—Ph—CF=CF—Ph—C₉H₁₉(n)
n-C₈H₁₇—Cy—CH₂CH₂—Ph—CF=CF—Ph—C₁₀H₂₁(n)

n-C₉H₁₉—Cy—CH₂CH₂—Ph—CF=CF—Ph—CH₃
n-C₉H₁₉—Cy—CH₂CH₂—Ph—CF=CF—Ph—C₃H₇(n)
n-C₉H₁₉—Cy—CH₂CH₂—Ph—CF=CF—Ph—C₅H₁₁(n)
n-C₉H₁₉—Cy—CH₂CH₂—Ph—CF=CF—Ph—C₇H₁₅(n)
n-C₉H₁₉—Cy—CH₂CH₂—Ph—CF=CF—Ph—C₉H₁₉(n)
n-C₉H₁₉—Cy—CH₂CH₂—Ph—CF=CF—Ph—C₁₀H₂₁(n)

n-C₁₀H₂₁—Cy—CH₂CH₂—Ph—CF=CF—Ph—CH₃
n-C₁₀H₂₁—Cy—CH₂CH₂—Ph—CF=CF—Ph—C₃H₇(n)
n-C₁₀H₂₁—Cy—CH₂CH₂—Ph—CF=CF—Ph—C₅H₁₁(n)
n-C₁₀H₂₁—Cy—CH₂CH₂—Ph—CF=CF—Ph—C₇H₁₅(n)
n-C₁₀H₂₁—Cy—CH₂CH₂—Ph—CF=CF—Ph—C₉H₁₉(n)
n-C₁₀H₂₁—Cy—CH₂CH₂—Ph—CF=CF—Ph—C₁₀H₂₁(n)

CH₃O—Cy—CH₂CH₂—Ph—CF=CF—Ph—CN
n-C₃H₇O—Cy—CH₂CH₂—Ph—CF=CF—Ph—CN
n-C₅H₁₁O—Cy—CH₂CH₂—Ph—CF=CF—Ph—CN
n-C₇H₁₅O—Cy—CH₂CH₂—Ph—CF=CF—Ph—CN
n-C₉H₁₉O—Cy—CH₂CH₂—Ph—CF=CF—Ph—CN
CH₃O—Cy—CH₂CH₂—Ph—CF=CF—Ph—CH₃
n-C₃H₇O—Cy—CH₂CH₂—Ph—CF=CF—Ph—C₃H₇(n)
n-C₅H₁₁O—Cy—CH₂CH₂—Ph—CF=CF—Ph—C₅H₁₁(n)
n-C₆H₁₃O—Cy—CH₂CH₂—Ph—CF=CF—Ph—C₆H₁₃(n)
n-C₇H₁₅O—Cy—CH₂CH₂—Ph—CF=CF—Ph—C₇H₁₅(n)
n-C₈H₁₇O—Cy—CH₂CH₂—Ph—CF=CF—Ph—C₈H₁₇(n)
n-C₉H₁₉O—Cy—CH₂CH₂—Ph—CF=CF—Ph—C₉H₁₉(n)
n-C₁₀H₂₁O—Cy—CH₂CH₂—Ph—CF=CF—Ph—C₁₀H₂₁(n)

Further, the following compounds can be prepared by changing tetrafluoroethylene to tetrachloroethylene.

CH₃—Cy—CH₂CH₂—Ph—CCl=CCl—Ph—CN

Trans-4-[2-(4-methyl-trans-cyclohexyl)ethyl]-4'-cyano-α,α'-dichlorostilbene

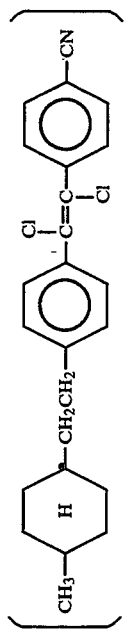

C₂H₅—Cy—CH₂CH₂—Ph—CCl=CCl—Ph—CN
n-C₄H₉—Cy—CH₂CH₂—Ph—CCl=CCl—Ph—CN
n-C₆H₁₃—Cy—CH₂CH₂—Ph—CCl=CCl—Ph—CN
n-C₈H₁₇—Cy—CH₂CH₂—Ph—CCl=CCl—Ph—CN
n-C₁₀H₂₁—Cy—CH₂CH₂—Ph—CCl=CCl—Ph—CN
CH₃—Cy—CH₂CH₂—Ph—CCl=CCl—Ph—CH₃
CH₃—Cy—CH₂CH₂—Ph—CCl=CCl—Ph—C₃H₇(n)
CH₃—Cy—CH₂CH₂—Ph—CCl=CCl—Ph—C₅H₁₁(n)
CH₃—Cy—CH₂CH₂—Ph—CCl=CCl—Ph—C₇H₁₅(n)
CH₃—Cy—CH₂CH₂—Ph—CCl=CCl—Ph—C₉H₁₉(n)
C₂H₅—Cy—CH₂CH₂—Ph—CCl=CCl—Ph—CH₃
C₂H₅—Cy—CH₂CH₂—Ph—CCl=CCl—Ph—C₃H₇(n)
C₂H₅—Cy—CH₂CH₂—Ph—CCl=CCl—Ph—C₅H₁₁(n)
C₂H₅—Cy—CH₂CH₂—Ph—CCl=CCl—Ph—C₇H₁₅(n)
C₂H₅—Cy—CH₂CH₂—Ph—CCl=CCl—Ph—C₉H₁₉(n)
n-C₃H₇—Cy—CH₂CH₂—Ph—CCl=CCl—Ph—CH₃
n-C₃H₇—Cy—CH₂CH₂—Ph—CCl=CCl—Ph—C₃H₇(n)
n-C₃H₇—Cy—CH₂CH₂—Ph—CCl=CCl—Ph—C₅H₁₁(n)
n-C₃H₇—Cy—CH₂CH₂—Ph—CCl=CCl—Ph—C₆H₁₃(n)
n-C₃H₇—Cy—CH₂CH₂—Ph—CCl=CCl—Ph—C₇H₁₅(n)
n-C₃H₇—Cy—CH₂CH₂—Ph—CCl=CCl—Ph—C₈H₁₇(n)
n-C₃H₇—Cy—CH₂CH₂—Ph—CCl=CCl—Ph—C₉H₁₉(n)
n-C₃H₇—Cy—CH₂CH₂—Ph—CCl=CCl—Ph—C₁₀H₂₁(n)
n-C₄H₉—Cy—CH₂CH₂—Ph—CCl=CCl—Ph—CH₃
n-C₄H₉—Cy—CH₂CH₂—Ph—CCl=CCl—Ph—C₃H₇(n)
n-C₄H₉—Cy—CH₂CH₂—Ph—CCl=CCl—Ph—C₅H₁₁(n)
n-C₄H₉—Cy—CH₂CH₂—Ph—CCl=CCl—Ph—C₆H₁₃(n)
n-C₄H₉—Cy—CH₂CH₂—Ph—CCl=CCl—Ph—C₇H₁₅(n)
n-C₄H₉—Cy—CH₂CH₂—Ph—CCl=CCl—Ph—C₈H₁₇(n)
n-C₄H₉—Cy—CH₂CH₂—Ph—CCl=CCl—Ph—C₉H₁₉(n)
n-C₄H₉—Cy—CH₂CH₂—Ph—CCl=CCl—Ph—C₁₀H₂₁(n)
n-C₅H₁₁—Cy—CH₂CH₂—Ph—CCl=CCl—Ph—CH₃
n-C₅H₁₁—Cy—CH₂CH₂—Ph—CCl=CCl—Ph—C₃H₇(n)
n-C₅H₁₁—Cy—CH₂CH₂—Ph—CCl=CCl—Ph—C₅H₁₁(n)
n-C₅H₁₁—Cy—CH₂CH₂—Ph—CCl=CCl—Ph—C₆H₁₃(n)
n-C₅H₁₁—Cy—CH₂CH₂—Ph—CCl=CCl—Ph—C₇H₁₅(n)
n-C₅H₁₁—Cy—CH₂CH₂—Ph—CCl=CCl—Ph—C₈H₁₇(n)
n-C₅H₁₁—Cy—CH₂CH₂—Ph—CCl=CCl—Ph—C₉H₁₉(n)
n-C₅H₁₁—Cy—CH₂CH₂—Ph—CCl=CCl—Ph—C₁₀H₂₁(n)
n-C₆H₁₃—Cy—CH₂CH₂—Ph—CCl=CCl—Ph—CH₃
n-C₆H₁₃—Cy—CH₂CH₂—Ph—CCl=CCl—Ph—C₂H₅ n-C₃H₇—Cy—CH₂CH₂—Ph—CCl=CCl—Ph—C₂H₅
n-C₅H₁₁—Cy—CH₂CH₂—Ph—CCl=CCl—Ph—CN
n-C₇H₁₅—Cy—CH₂CH₂—Ph—CCl=CCl—Ph—CN
n-C₉H₁₉—Cy—CH₂CH₂—Ph—CCl=CCl—Ph—CN
CH₃—Cy—CH₂CH₂—Ph—CCl=CCl—Ph—C₂H₅
CH₃—Cy—CH₂CH₂—Ph—CCl=CCl—Ph—C₄H₉(n)
CH₃—Cy—CH₂CH₂—Ph—CCl=CCl—Ph—C₆H₁₃(n)
CH₃—Cy—CH₂CH₂—Ph—CCl=CCl—Ph—C₈H₁₇(n)
CH₃—Cy—CH₂CH₂—Ph—CCl=CCl—Ph—C₁₀H₂₁(n)
C₂H₅—Cy—CH₂CH₂—Ph—CCl=CCl—Ph—C₂H₅
C₂H₅—Cy—CH₂CH₂—Ph—CCl=CCl—Ph—C₄H₉(n)
C₂H₅—Cy—CH₂CH₂—Ph—CCl=CCl—Ph—C₆H₁₃(n)
C₂H₅—Cy—CH₂CH₂—Ph—CCl=CCl—Ph—C₈H₁₇(n)
C₂H₅—Cy—CH₂CH₂—Ph—CCl=CCl—Ph—C₁₀H₂₁(n)
n-C₃H₇—Cy—CH₂CH₂—Ph—CCl=CCl—Ph—C₂H₅
n-C₃H₇—Cy—CH₂CH₂—Ph—CCl=CCl—Ph—C₄H₉(n)

n-C₄H₉—Cy—CH₂CH₂—Ph—CCl=CCl—Ph—C₂H₅
n-C₄H₉—Cy—CH₂CH₂—Ph—CCl=CCl—Ph—C₄H₉(n)

-continued n-C$_6$H$_{13}$—Cy—CH$_2$CH$_2$—Ph—CCl=CCl—Ph—C$_3$H$_7$(n)
n-C$_6$H$_{13}$—Cy—CH$_2$CH$_2$—Ph—CCl=CCl—Ph—C$_4$H$_9$(n)
n-C$_6$H$_{13}$—Cy—CH$_2$CH$_2$—Ph—CCl=CCl—Ph—C$_5$H$_{11}$(n)
n-C$_6$H$_{13}$—Cy—CH$_2$CH$_2$—Ph—CCl=CCl—Ph—C$_6$H$_{13}$(n)
n-C$_6$H$_{13}$—Cy—CH$_2$CH$_2$—Ph—CCl=CCl—Ph—C$_7$H$_{15}$(n)
n-C$_6$H$_{13}$—Cy—CH$_2$CH$_2$—Ph—CCl=CCl—Ph—C$_8$H$_{17}$(n)
n-C$_6$H$_{13}$—Cy—CH$_2$CH$_2$—Ph—CCl=CCl—Ph—C$_9$H$_{19}$(n)
n-C$_6$H$_{13}$—Cy—CH$_2$CH$_2$—Ph—CCl=CCl—Ph—C$_{10}$H$_{21}$(n)
n-C$_7$H$_{15}$—Cy—CH$_2$CH$_2$—Ph—CCl=CCl—Ph—CH$_3$
n-C$_7$H$_{15}$—Cy—CH$_2$CH$_2$—Ph—CCl=CCl—Ph—C$_2$H$_5$
n-C$_7$H$_{15}$—Cy—CH$_2$CH$_2$—Ph—CCl=CCl—Ph—C$_3$H$_7$(n)
n-C$_7$H$_{15}$—Cy—CH$_2$CH$_2$—Ph—CCl=CCl—Ph—C$_4$H$_9$(n)
n-C$_7$H$_{15}$—Cy—CH$_2$CH$_2$—Ph—CCl=CCl—Ph—C$_5$H$_{11}$(n)
n-C$_7$H$_{15}$—Cy—CH$_2$CH$_2$—Ph—CCl=CCl—Ph—C$_6$H$_{13}$(n)
n-C$_7$H$_{15}$—Cy—CH$_2$CH$_2$—Ph—CCl=CCl—Ph—C$_7$H$_{15}$(n)
n-C$_7$H$_{15}$—Cy—CH$_2$CH$_2$—Ph—CCl=CCl—Ph—C$_8$H$_{17}$(n)
n-C$_7$H$_{15}$—Cy—CH$_2$CH$_2$—Ph—CCl=CCl—Ph—C$_9$H$_{19}$(n)
n-C$_7$H$_{15}$—Cy—CH$_2$CH$_2$—Ph—CCl=CCl—Ph—C$_{10}$H$_{21}$(n)
n-C$_8$H$_{17}$—Cy—CH$_2$CH$_2$—Ph—CCl=CCl—Ph—CH$_3$
n-C$_8$H$_{17}$—Cy—CH$_2$CH$_2$—Ph—CCl=CCl—Ph—C$_2$H$_5$
n-C$_8$H$_{17}$—Cy—CH$_2$CH$_2$—Ph—CCl=CCl—Ph—C$_3$H$_7$(n)
n-C$_8$H$_{17}$—Cy—CH$_2$CH$_2$—Ph—CCl=CCl—Ph—C$_4$H$_9$(n)
n-C$_8$H$_{17}$—Cy—CH$_2$CH$_2$—Ph—CCl=CCl—Ph—C$_5$H$_{11}$(n)
n-C$_8$H$_{17}$—Cy—CH$_2$CH$_2$—Ph—CCl=CCl—Ph—C$_6$H$_{13}$(n)
n-C$_8$H$_{17}$—Cy—CH$_2$CH$_2$—Ph—CCl=CCl—Ph—C$_7$H$_{15}$(n)
n-C$_8$H$_{17}$—Cy—CH$_2$CH$_2$—Ph—CCl=CCl—Ph—C$_8$H$_{17}$(n)
n-C$_8$H$_{17}$—Cy—CH$_2$CH$_2$—Ph—CCl=CCl—Ph—C$_9$H$_{19}$(n)
n-C$_8$H$_{17}$—Cy—CH$_2$CH$_2$—Ph—CCl=CCl—Ph—C$_{10}$H$_{21}$(n)
n-C$_9$H$_{19}$—Cy—CH$_2$CH$_2$—Ph—CCl=CCl—Ph—CH$_3$
n-C$_9$H$_{19}$—Cy—CH$_2$CH$_2$—Ph—CCl=CCl—Ph—C$_2$H$_5$
n-C$_9$H$_{19}$—Cy—CH$_2$CH$_2$—Ph—CCl=CCl—Ph—C$_3$H$_7$(n)
n-C$_9$H$_{19}$—Cy—CH$_2$CH$_2$—Ph—CCl=CCl—Ph—C$_4$H$_9$(n)
n-C$_9$H$_{19}$—Cy—CH$_2$CH$_2$—Ph—CCl=CCl—Ph—C$_5$H$_{11}$(n)
n-C$_9$H$_{19}$—Cy—CH$_2$CH$_2$—Ph—CCl=CCl—Ph—C$_6$H$_{13}$(n)
n-C$_9$H$_{19}$—Cy—CH$_2$CH$_2$—Ph—CCl=CCl—Ph—C$_7$H$_{15}$(n)
n-C$_9$H$_{19}$—Cy—CH$_2$CH$_2$—Ph—CCl=CCl—Ph—C$_8$H$_{17}$(n)
n-C$_9$H$_{19}$—Cy—CH$_2$CH$_2$—Ph—CCl=CCl—Ph—C$_9$H$_{19}$(n)
n-C$_9$H$_{19}$—Cy—CH$_2$CH$_2$—Ph—CCl=CCl—Ph—C$_{10}$H$_{21}$(n)
n-C$_{10}$H$_{21}$—Cy—CH$_2$CH$_2$—Ph—CCl=CCl—Ph—CH$_3$
n-C$_{10}$H$_{21}$—Cy—CH$_2$CH$_2$—Ph—CCl=CCl—Ph—C$_2$H$_5$
n-C$_{10}$H$_{21}$—Cy—CH$_2$CH$_2$—Ph—CCl=CCl—Ph—C$_3$H$_7$(n)
n-C$_{10}$H$_{21}$—Cy—CH$_2$CH$_2$—Ph—CCl=CCl—Ph—C$_4$H$_9$(n)
n-C$_{10}$H$_{21}$—Cy—CH$_2$CH$_2$—Ph—CCl=CCl—Ph—C$_5$H$_{11}$(n)
n-C$_{10}$H$_{21}$—Cy—CH$_2$CH$_2$—Ph—CCl=CCl—Ph—C$_6$H$_{13}$(n)
n-C$_{10}$H$_{21}$—Cy—CH$_2$CH$_2$—Ph—CCl=CCl—Ph—C$_7$H$_{15}$(n)
n-C$_{10}$H$_{21}$—Cy—CH$_2$CH$_2$—Ph—CCl=CCl—Ph—C$_8$H$_{17}$(n)
n-C$_{10}$H$_{21}$—Cy—CH$_2$CH$_2$—Ph—CCl=CCl—Ph—C$_9$H$_{19}$(n)
n-C$_{10}$H$_{21}$—Cy—CH$_2$CH$_2$—Ph—CCl=CCl—Ph—C$_{10}$H$_{21}$(n)
CH$_3$O—Cy—CH$_2$CH$_2$—Ph—CCl=CCl—Ph—CN
n-C$_3$H$_7$O—Cy—CH$_2$CH$_2$—Ph—CCl=CCl—Ph—CN
n-C$_5$H$_{11}$O—Cy—CH$_2$CH$_2$—Ph—CCl=CCl—Ph—CN
n-C$_7$H$_{15}$O—Cy—CH$_2$CH$_2$—Ph—CCl=CCl—Ph—CN
n-C$_9$H$_{19}$O—Cy—CH$_2$CH$_2$—Ph—CCl=CCl—Ph—CN
CH$_3$O—Cy—CH$_2$CH$_2$—Ph—CCl=CCl—Ph—CH$_3$ C$_2$H$_5$O—Cy—CH$_2$CH$_2$—Ph—CCl=CCl—Ph—CN
n-C$_4$H$_9$O—Cy—CH$_2$CH$_2$—Ph—CCl=CCl—Ph—CN
n-C$_6$H$_{13}$O—Cy—CH$_2$CH$_2$—Ph—CCl=CCl—Ph—CN
n-C$_8$H$_{17}$O—Cy—CH$_2$CH$_2$—Ph—CCl=CCl—Ph—CN
n-C$_{10}$H$_{21}$O—Cy—CH$_2$CH$_2$—Ph—CCl=CCl—Ph—CN
C$_2$H$_5$O—Cy—CH$_2$CH$_2$—Ph—CCl=CCl—Ph—C$_2$H$_5$ -continued n-C$_3$H$_7$O—Cy—CH$_2$CH$_2$—Ph—CCl=CCl—Ph—C$_3$H$_7$(n)
n-C$_4$H$_9$O—Cy—CH$_2$CH$_2$—Ph—CCl=CCl—Ph—C$_4$H$_9$(n)
n-C$_5$H$_{11}$O—Cy—CH$_2$CH$_2$—Ph—CCl=CCl—Ph—C$_5$H$_{11}$(n)
n-C$_6$H$_{13}$O—Cy—CH$_2$CH$_2$—Ph—CCl=CCl—Ph—C$_6$H$_{13}$(n)
n-C$_7$H$_{15}$O—Cy—CH$_2$CH$_2$—Ph—CCl=CCl—Ph—C$_7$H$_{15}$(n)
n-C$_8$H$_{17}$O—Cy—CH$_2$CH$_2$—Ph—CCl=CCl—Ph—C$_8$H$_{17}$(n)
n-C$_9$H$_{19}$O—Cy—CH$_2$CH$_2$—Ph—CCl=CCl—Ph—C$_9$H$_{19}$(n)
n-C$_{10}$H$_{21}$O—Cy—CH$_2$CH$_2$—Ph—CCl=CCl—Ph—C$_{10}$H$_{21}$(n)

The following compounds can be prepared by changing the raw material of Example 1 or Example 2:

In the same manner as in Example 1, 17.2 g (0.086 mol) of 1-(4-n-propylphenyl)-1,2,2-trifluoroethylene was prepared from p-n-propyliodobenzene. Then, 26.15 g (0.086 mol) of 4-[(tetrahydropyran-2-yl)oxy]iodobenzene was reacted thereto instead of p-n-propyliodoben- Trans-4-[2-(4-methyl-trans-cyclohexyl)ethyl]-4'-cyano-3'-fluoro-α,α'-difluorostilbene

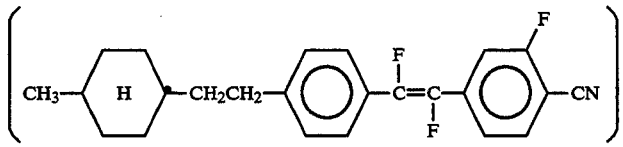

$C_2H_5$—Cy—$CH_2CH_2$—Ph—CF=CF—PhF—CN
n-$C_4H_9$—Cy—$CH_2CH_2$—Ph—CF=CF—PhF—CN
n-$C_6H_{13}$—Cy—$CH_2CH_2$—Ph—CF=CF—PhF—CN
n-$C_8H_{17}$—Cy—$CH_2CH_2$—Ph—CF=CF—PhF—CN
n-$C_{10}H_{21}$—Cy—$CH_2CH_2$—Ph—CF=CF—PhF—CN
$CH_3O$—Cy—$CH_2CH_2$—Ph—CF=CF—PhF—CN
n-$C_3H_7O$—Cy—$CH_2CH_2$—Ph—CF=CF—PhF—CN
n-$C_5H_{11}O$—Cy—$CH_2CH_2$—Ph—CF=CF—PhF—CN
n-$C_7H_{15}O$—Cy—$CH_2CH_2$—Ph—CF=CF—PhF—CN
n-$C_9H_{19}O$—Cy—$CH_2CH_2$—Ph—CF=CF—PhF—CN n-$C_3H_7$—Cy—$CH_2CH_2$—Ph—CF=CF—PhF—CN
n-$C_5H_{11}$—Cy—$CH_2CH_2$—Ph—CF=CF—PhF—CN
n-$C_7H_{15}$—Cy—$CH_2CH_2$—Ph—CF=CF—PhF—CN
n-$C_9H_{19}$—Cy—$CH_2CH_2$—Ph—CF=CF—PhF—CN
$C_2H_5O$—Cy—$CH_2CH_2$—Ph—CF=CF—PhF—CN
n-$C_4H_9O$—Cy—$CH_2CH_2$—Ph—CF=CF—PhF—CN
n-$C_6H_{13}O$—Cy—$CH_2CH_2$—Ph—CF=CF—PhF—CN
n-$C_8H_{17}O$—Cy—$CH_2CH_2$—Ph—CF=CF—PhF—CN
n-$C_{10}H_{21}O$—Cy—$CH_2CH_2$—Ph—CF=CF—PhF—CN

Further, the following compounds can be prepared by changing tetrafluoroethylene to tetrachloroethylene.

$CH_3$—Cy—$CH_2CH_2$—Ph—CCl=CCl—PhF—CN
Trans-4-[2-(4-methyl-trans-cyclohexyl)ethyl]-4'-cyano-3'-fluoro-α,α'-dichlorostilbene

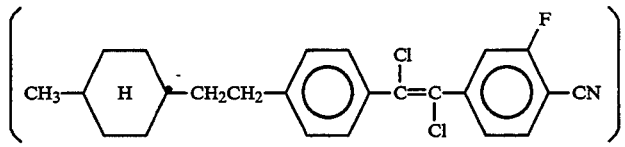

$C_2H_5$—Cy—$CH_2CH_2$—Ph—CCl=CCl—PhF—CN
n-$C_4H_9$—Cy—$CH_2CH_2$—Ph—CCl=CCl—PhF—CN
n-$C_6H_{13}$—Cy—$CH_2CH_2$—Ph—CCl=CCl—PhF—CN
n-$C_8H_{17}$—Cy—$CH_2CH_2$—Ph—CCl=CCl—PhF—CN
n-$C_{10}H_{21}$—Cy—$CH_2CH_2$—Ph—CCl=CCl—PhF—CN
$CH_3O$—Cy—$CH_2CH_2$—Ph—CCl=CCl—PhF—CN
n-$C_3H_7O$—Cy—$CH_2CH_2$—Ph—CCl=CCl—PhF—CN
n-$C_5H_{11}O$—Cy—$CH_2CH_2$—Ph—CCl=CCl—PhF—CN
n-$C_7H_{15}O$—Cy—$CH_2CH_2$—Ph—CCl=CCl—PhF—CN
n-$C_9H_{19}O$—Cy—$CH_2CH_2$—Ph—CCl=CCl—PhF—CN n-$C_3H_7$—Cy—$CH_2CH_2$—Ph—CCl=CCl—PhF—CN
n-$C_5H_{11}$—Cy—$CH_2CH_2$—Ph—CCl=CCl—PhF—CN
n-$C_7H_{15}$—Cy—$CH_2CH_2$—Ph—CCl=CCl—PhF—CN
n-$C_9H_{19}$—Cy—$CH_2CH_2$—Ph—CCl=CCl—PhF—CN
$C_2H_5O$—Cy—$CH_2CH_2$—Ph—CCl=CCl—PhF—CN
n-$C_4H_9O$—Cy—$CH_2CH_2$—Ph—CCl=CCl—PhF—CN
n-$C_6H_{13}O$—Cy—$CH_2CH_2$—Ph—CCl=CCl—PhF—CN
n-$C_8H_{17}O$—Cy—$CH_2CH_2$—Ph—CCl=CCl—PhF—CN
n-$C_{10}H_{21}O$—Cy—$CH_2CH_2$—Ph—CCl=CCl—PhF—CN

Further, in the same manner, the following compounds can be prepared.

zene used in Example 1 to obtain 21.6 g (yield:70%) of trans-{[(4-tetrahydropyran-2-yl)oxy]-4'-n-propyl}di- $CH_3O$—$C_2H_5$—Ph—CF=CF—Ph—$C_3H_7$(n)
$CH_3O$—$C_2H_5$—Ph—CCl=CCl—Ph—$C_3H_7$(n)
n-$C_3H_7$—Ph—CF=CF—Ph—F
n-$C_3H_7$—Ph—CCl=CCl—Ph—F
n-$C_3H_7$—Ph—CF=CF—Ph—Cl
n-$C_3H_7$—Ph—CCl=CCl—Ph—Cl $CH_3O$—$C_3H_7$—Ph—CF=CF—Ph—$C_4H_9$(n)
$CH_3O$—$C_3H_7$—Ph—CCl=CCl—Ph—$C_4H_9$(n)
n-$C_4H_9$—Ph—CF=CF—Ph—F
n-$C_4H_9$—Ph—CCl=CCl—Ph—F
n-$C_4H_9$—Ph—CF=CF—Ph—Cl
n-$C_4H_9$—Ph—CCl=CCl—Ph—Cl

EXAMPLE 3

In 1 l of four-necked flask, 178 g (0.81 mol) of p-iodophenol, 81.68 g of dihydropyran and hexane were introduced and stirred for one hour. Then, 15 g of a cation exchange resin Amberlyst 15 (Rohm & Haas Co. "Amberlyst" ®) was added thereto and stirred at room temperature overnight. Amberlyst 15 was removed by filtration and the filtrate was washed with an alkali and then with water. The oil layer was dried over sodium hydroxide and the solvent was distilled off to obtain 189.7 g (yield: 77%) of 4-[(tetrahydropyran-2-yl)oxy]iodobenzene.

fluorostilbene.
The reaction solution was refluxed in 2N hydrochloric acid for one hour to obtain 11.5 g (yield: 70%) of trans-4-hydroxy-4'-n-propyl)difluorostilbene.

Then, 11.5 g of trans-(4-hydroxy-4'-n-propyl)difluorostilbene thus obtained was dissolved in 30 ml of methylene chloride and 3.3 g of pyridine was added thereto at room temperature. The mixture was cooled to 0° C. and 6.5 g of p-toluoyl chloride was dropwise added thereto. The mixture was stirred at room temperature for one hour and cooled, and then diluted hydrochloric acid was added thereto, followed by filtration. The solvent was distilled off and a crude crystal thus obtained was purified by silica gel column chromotography to obtain 15.5 g (yield: 94%) of trans[4-(4''-methylbenzoyloxy)-4'-n-propyl]difluorostilbene.
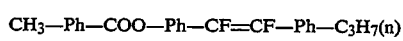
The analytical result of the compound are as follows:
MS m/e 392 (M+)
In the same manner as in Example 1, 2 or 3, the following compounds are synthesized:

n-C₃H₇—Ph—COO—Ph—CF=CF—Ph—C₃H₇(n)
n-C₃H₇—Ph—COO—Ph—CCl=CCl—Ph—C₃H₇(n)
n-C₃H₇—Ph—COO—Ph—CF=CF—Ph—C₄H₉(n)
n-C₃H₇—Ph—COO—Ph—CCl=CCl—Ph—C₄H₉(n)
n-C₄H₉—Ph—COO—Ph—CF=CF—Ph—C₃H₇(n)
n-C₄H₉—Ph—COO—Ph—CCl=CCl—Ph—C₃H₇(n)
n-C₃H₇—Ph—OCO—Ph—CF=CF—Ph—C₃H₇(n)
n-C₃H₇—Ph—OCO—Ph—CCl=CCl—Ph—C₃H₇(n)
n-C₃H₇—Ph—OCO—Ph—CF=CF—Ph—C₄H₉(n)
n-C₃H₇—Ph—OCO—Ph—CCl=CCl—Ph—C₄H₉(n)
n-C₄H₉—Ph—OCO—Ph—CF=CF—Ph—C₃H₇(n)
n-C₄H₉—Ph—OCO—Ph—CCl=CCl—Ph—C₃H₇(n)
n-C₃H₇—Cy—COO—Ph—CF=CF—Ph—C₃H₇(n)
n-C₃H₇—Cy—COO—Ph—CCl=CCl—Ph—C₃H₇(n)
n-C₃H₇—Cy—COO—Ph—CF=CF—Cy—C₃H₇(n)
n-C₃H₇—Cy—COO—Ph—CF=CF—Ph—C₄H₉(n)
n-C₃H₇—Cy—COO—Ph—CCl=CCl—Ph—C₄H₉(n)
n-C₄H₉—Cy—COO—Ph—CF=CF—Ph—C₃H₇(n)
n-C₄H₉—Cy—COO—Ph—CCl=CCl—Ph—C₃H₇(n)
n-C₃H₇—Cy—OCO—Ph—CF=CF—Ph—C₃H₇(n)
n-C₃H₇—Cy—OCO—Ph—CCl=CCl—Ph—C₃H₇(n)
n-C₃H₇—Cy—OCO—Ph—CF=CF—Cy—C₃H₇(n)
n-C₃H₇—Cy—OCO—Ph—CF=CF—Ph—C₄H₉(n)
n-C₃H₇—Cy—OCO—Ph—CCl=CCl—Ph—C₄H₉(n)
n-C₄H₉—Cy—OCO—Ph—CF=CF—Ph—C₃H₇(n)
n-C₄H₉—Cy—OCO—Ph—CCl=CCl—Ph—C₃H₇(n)
n-C₃H₇—Cy—CH=CH—Ph—CF=CF—Ph—C₃H₇(n)
n-C₃H₇—Cy—CH=CH—Ph—CCl=CCl—Ph—C₃H₇(n)
n-C₃H₇—Cy—C≡C—Ph—CF=CF—Ph—C₃H₇(n)
n-C₃H₇—Cy—C≡C—Ph—CCl=CCl—Ph—C₃H₇(n)
n-C₃H₇—Cy—CH₂O—Ph—CF=CF—Ph—C₃H₇(n)
n-C₃H₇—Cy—CH₂O—Ph—CCl=CCl—Ph—C₃H₇(n)
n-C₃H₇—Cy—OCH₂—Ph—CF=CF—Ph—C₃H₇(n)
n-C₃H₇—Cy—OCH₂—Ph—CCl=CCl—Ph—C₃H₇(n)
n-C₃H₇—Cy—CH=N—Ph—CF=CF—Ph—C₃H₇(n)
n-C₃H₇—Cy—CH=N—Ph—CCl=CCl—Ph—C₃H₇(n)
n-C₃H₇—Cy—N=N—Ph—CF=CF—Ph—C₃H₇(n)
n-C₃H₇—Cy—N=N—Ph—CCl=CCl—Ph—C₃H₇(n)
n-C₃H₇—Cy—NO=N—Ph—CF=CF—Ph—C₃H₇(n)
n-C₃H₇—Cy—NO=N—Ph—CCl=CCl—Ph—C₃H₇(n)
n-C₃H₇—Cy—N=NO—Ph—CF=CF—Ph—C₃H₇(n)
n-C₃H₇—Cy—N=NO—Ph—CCl=CCl—Ph—C₃H₇(n)
n-C₃H₇—Cy—O—Ph—CF=CF—Ph—C₃H₇(n)
n-C₃H₇—Cy—O—Ph—CCl=CCl—Ph—C₃H₇(n)
n-C₃H₇—Cy—CH₂—Ph—CF=CF—Ph—C₃H₇(n)
n-C₃H₇—Cy—CH₂—Ph—CCl=CCl—Ph—C₃H₇(n)

n-C₄H₉—Ph—COO—Ph—CF=CF—Ph—C₄H₉(n)
n-C₄H₉—Ph—COO—Ph—CCl=CCl—Ph—C₄H₉(n)
n-C₄H₉—Ph—COO—Ph—CF=CF—Ph—C₄H₉(n)
n-C₄H₉—Ph—COO—Ph—CCl=CCl—Ph—C₄H₉(n)
n-C₄H₉—Cy—COO—Ph—CF=CF—Ph—C₄H₉(n)
n-C₄H₉—Cy—COO—Ph—CCl=CCl—Ph—C₄H₉(n)
n-C₄H₉—Cy—COO—Ph—CF=CF—Ph——C₄H₉(n)
n-C₄H₉—Cy—COO—Ph—CCl=CCl—Ph—Cy—C₄H₉(n)
n-C₄H₉—Cy—CH=CH—Ph—CF=CF—Ph—C₄H₉(n)
n-C₄H₉—Cy—CH=CH—Ph—CCl=CCl—Ph—C₄H₉(n)
n-C₄H₉—Cy—C≡C—Ph—CF=CF—Ph—C₄H₉(n)
n-C₄H₉—Cy—C≡C—Ph—CCl=CCl—Ph—C₄H₉(n)
n-C₄H₉—Cy—CH₂O—Ph—CF=CF—Ph—C₄H₉(n)
n-C₄H₉—Cy—CH₂O—Ph—CCl=CCl—Ph—C₄H₉(n)
n-C₄H₉—Cy—OCH₂—Ph—CF=CF—Ph—C₄H₉(n)
n-C₄H₉—Cy—OCH₂—Ph—CCl=CCl—Ph—C₄H₉(n)
n-C₄H₉—Cy—CH=N—Ph—CF=CF—Ph—C₄H₉(n)
n-C₄H₉—Cy—CH=N—Ph—CCl=CCl—Ph—C₄H₉(n)
n-C₄H₉—Cy—N=N—Ph—CF=CF—Ph—C₄H₉(n)
n-C₄H₉—Cy—N=N—Ph—CCl=CCl—Ph—C₄H₉(n)
n-C₄H₉—Cy—NO=N—Ph—CF=CF—Ph—C₄H₉(n)
n-C₄H₉—Cy—NO=N—Ph—CCl=CCl—Ph—C₄H₉(n)
n-C₄H₉—Cy—N=NO—Ph—CF=CF—Ph—C₄H₉(n)
n-C₄H₉—Cy—N=NO—Ph—CCl=CCl—Ph—C₄H₉(n)
n-C₄H₉—Cy—O—Ph—CF=CF—Ph—C₄H₉(n)
n-C₄H₉—Cy—O—Ph—CCl=CCl—Ph—C₄H₉(n)
n-C₄H₉—Cy—CH₂—Ph—CF=CF—Ph—C₄H₉(n)
n-C₄H₉—Cy—CH₂—Ph—CCl=CCl—Ph—C₄H₉(n)

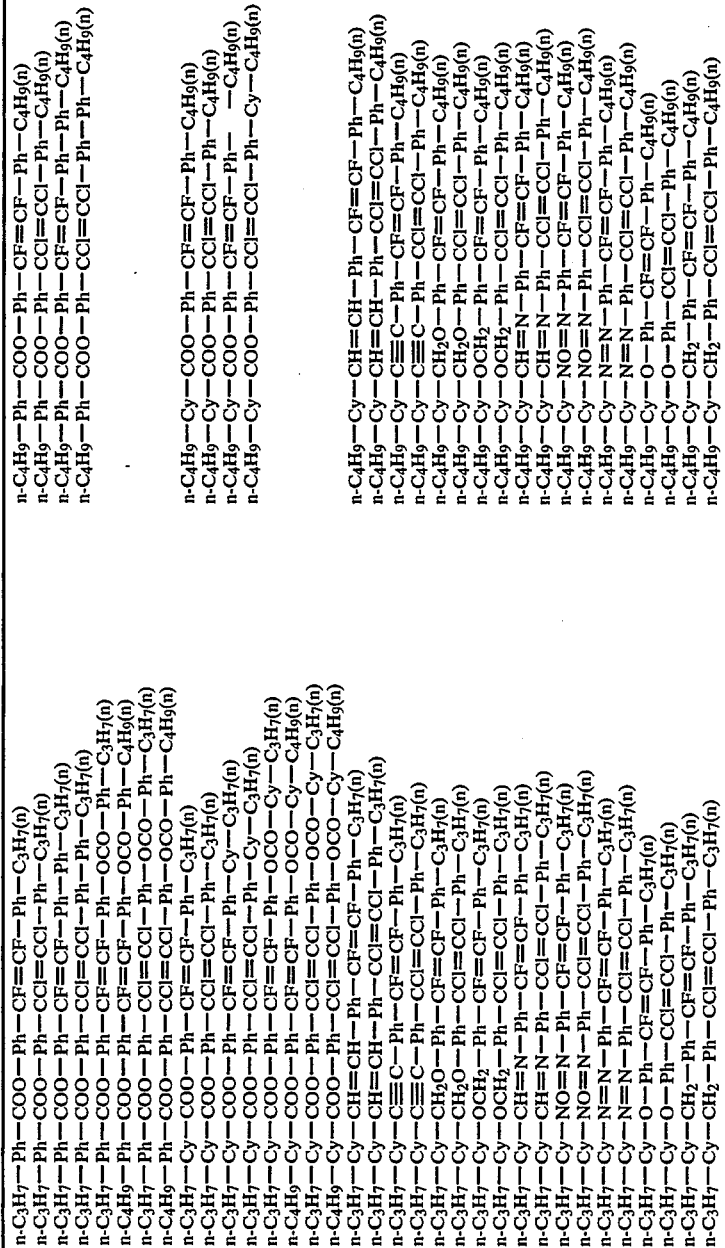

EXAMPLE 4

Air in a dried four-necked flask was replaced by nitrogen, and 220 ml of dry n-hexane, 44 ml of dry diethylether and 43.6 g (0.20 mol) of p-iodotoluene were introduced, and 111 g (0.26 mol) of a hexane solution of n-butyl lithium was gradually added thereto while cooling to −20° C. and stirring, to obtain a p-methylphenyl lithium solution.

The solution thus obtained was cooled to −80° C., and then the system was vacuumed, and tetrafluoroethylene gas was introduced by means of a gas buret in an amount corresponding to 0.30 mol. Then, the interior of the system was returned to atmospheric pressure with nitrogen gas, and stirring was continued at −80° C. for one hour. Then, the reaction mixture was returned to room temperature, and nitrogen gas was introduced to purge unreacted tetrafluoroethylene gas.

The interior of the system was again cooled to −80° C. Then, in the same manner as in the case of p-methylphenyl lithium, a p-trifluoromethylphenyl lithium solution prepared from 45.0 g (0.20 mol) of p-bromobenzotrifluoride and 94 g (0.22 mol) of a hexane solution of n-butyl lithium, was gradually dropwise added. After completion of the dropwise addition, stirring was continued for one hour at a temperature of −80° C. Then, the reaction mixture was returned to room temperature and poured into ice water and neutralized with dilute hydrochloric acid. Then, the organic layer was separated.

The aqueous phase was extracted with ethyl ether, and then the ether layer was combined to the above organic layer. The combined organic layer was washed with water and then dried over anhydrous magnesium sulfate. The solvent was distilled off, and then toluene was added to the residue, and the mixture was purified by silica gel column chromatography, and after distilling the solvent off, the product was recrystallized from n-hexane, to obtain 7.55 g of the following desired compound. m.p.: 136.5° C.

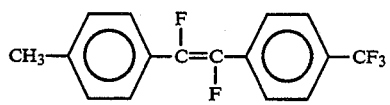

Figure 14:
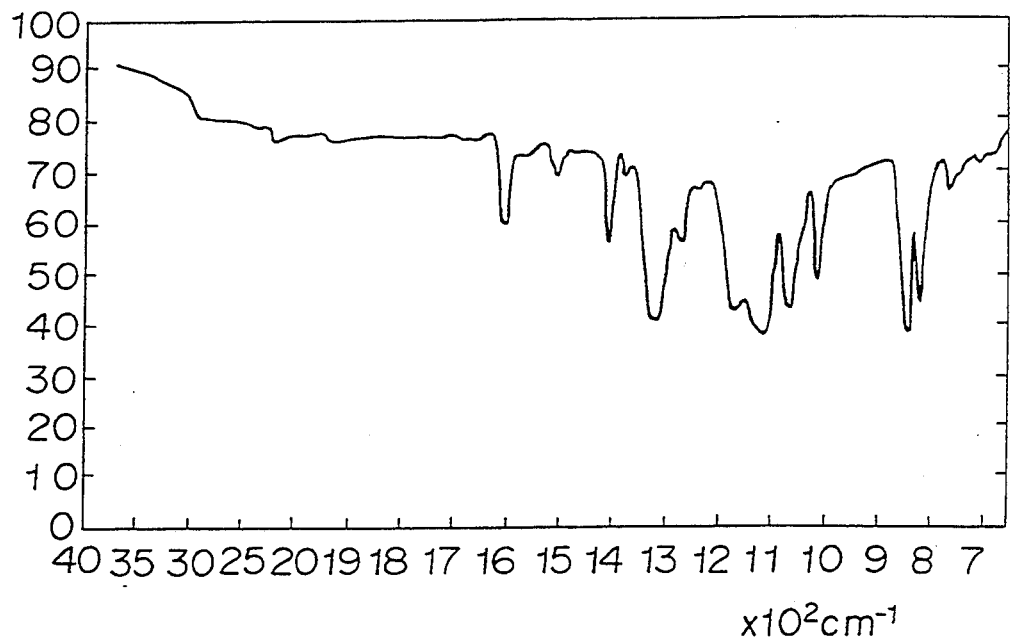

The IR spectrum (KBr tablet) of this compound is shown in FIG. 14.

In the same manner as in Examples 1–4, the following compounds can be prepared.

C$_2$H$_5$—Ph—CF=CF—Ph—CF$_3$
Trans-4-ethyl-4'-trifluoromethyl-α,α'-difluorostilbene

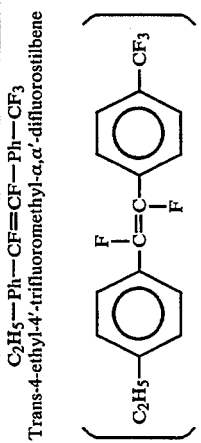

n-C$_3$H$_7$—Ph—CF=CF—Ph—CF$_3$
n-C$_5$H$_{11}$—Ph—CF=CF—Ph—CF$_3$
n-C$_7$H$_{15}$—Ph—CF=CF—Ph—CF$_3$
n-C$_9$H$_{19}$—Ph—CF=CF—Ph—CF$_3$
CH$_3$O—Ph—CF=CF—Ph—CF$_3$
n-C$_3$H$_7$O—Ph—CF=CF—Ph—CF$_3$
n-C$_5$H$_{11}$O—Ph—CF=CF—Ph—CF$_3$
n-C$_7$H$_{15}$O—Ph—CF=CF—Ph—CF$_3$
n-C$_9$H$_{19}$O—Ph—CF=CF—Ph—CF$_3$
CH$_3$OCH$_2$—Ph—CF=CF—Ph—CF$_3$
n-C$_3$H$_7$OCH$_2$—Ph—CF=CF—Ph—CF$_3$
n-C$_5$H$_{11}$OCH$_2$—Ph—CF=CF—Ph—CF$_3$
n-C$_7$H$_{15}$OCH$_2$—Ph—CF=CF—Ph—CF$_3$
CH$_3$—Ph—CF=CF—Ph—CH$_2$CF$_3$
n-C$_3$H$_7$—Ph—CF=CF—Ph—CH$_2$CF$_3$
n-C$_5$H$_{11}$—Ph—CF=CF—Ph—CH$_2$CF$_3$
n-C$_7$H$_{15}$—Ph—CF=CF—Ph—CH$_2$CF$_3$
n-C$_9$H$_{19}$—Ph—CF=CF—Ph—CH$_2$CF$_3$
CH$_3$O—Ph—CF=CF—Ph—CH$_2$CF$_3$
n-C$_3$H$_7$O—Ph—CF=CF—Ph—CH$_2$CF$_3$
n-C$_5$H$_{11}$O—Ph—CF=CF—Ph—CH$_2$CF$_3$
n-C$_7$H$_{15}$O—Ph—CF=CF—Ph—CH$_2$CF$_3$
n-C$_9$H$_{19}$O—Ph—CF=CF—Ph—CH$_2$CF$_3$
CH$_3$OCH$_2$—Ph—CF=CF—Ph—CH$_2$CF$_3$
n-C$_3$H$_7$OCH$_2$—Ph—CF=CF—Ph—CH$_2$CF$_3$
n-C$_5$H$_{11}$OCH$_2$—Ph—CF=CF—Ph—CH$_2$CF$_3$
n-C$_7$H$_{15}$OCH$_2$—Ph—CF=CF—Ph—CH$_2$CF$_3$
CH$_3$—Ph—CF=CF—Ph—CF$_2$CF$_3$
n-C$_3$H$_7$—Ph—CF=CF—Ph—CF$_2$CF$_3$
n-C$_5$H$_{11}$—Ph—CF=CF—Ph—CF$_2$CF$_3$
n-C$_7$H$_{15}$—Ph—CF=CF—Ph—CF$_2$CF$_3$
n-C$_9$H$_{19}$—Ph—CF=CF—Ph—CF$_2$CF$_3$
CH$_3$O—Ph—CF=CF—Ph—CF$_2$CF$_3$
n-C$_3$H$_7$O—Ph—CF=CF—Ph—CF$_2$CF$_3$
n-C$_5$H$_{11}$O—Ph—CF=CF—Ph—CF$_2$CF$_3$
n-C$_7$H$_{15}$O—Ph—CF=CF—Ph—CF$_2$CF$_3$
n-C$_8$H$_{17}$O—Ph—CF=CF—Ph—CF$_2$CF$_3$
CH$_3$OCH$_2$—Ph—CF=CF—Ph—CF$_2$CF$_3$
n-C$_3$H$_7$OCH$_2$—Ph—CF=CF—Ph—CF$_2$CF$_3$
n-C$_5$H$_{11}$OCH$_2$—Ph—CF=CF—Ph—CF$_2$CF$_3$
n-C$_7$H$_{15}$OCH$_2$—Ph—CF=CF—Ph—CF$_2$CF$_3$
CH$_3$—Cy—Ph—CF=CF—Ph—CF$_3$ n-C$_4$H$_9$—Ph—CF=CF—Ph—CF$_3$
n-C$_6$H$_{13}$—Ph—CF=CF—Ph—CF$_3$
n-C$_8$H$_{17}$—Ph—CF=CF—Ph—CF$_3$
n-C$_{10}$H$_{21}$—Ph—CF=CF—Ph—CF$_3$
C$_2$H$_5$O—Ph—CF=CF—Ph—CF$_3$
n-C$_4$H$_9$O—Ph—CF=CF—Ph—CF$_3$
n-C$_6$H$_{13}$O—Ph—CF=CF—Ph—CF$_3$
n-C$_8$H$_{17}$O—Ph—CF=CF—Ph—CF$_3$
n-C$_{10}$H$_{21}$O—Ph—CF=CF—Ph—CF$_3$
C$_2$H$_5$OCH$_2$—Ph—CF=CF—Ph—CF$_3$
n-C$_4$H$_9$OCH$_2$—Ph—CF=CF—Ph—CF$_3$
n-C$_6$H$_{13}$OCH$_2$—Ph—CF=CF—Ph—CF$_3$
n-C$_8$H$_{17}$OCH$_2$—Ph—CF=CF—Ph—CF$_3$
C$_2$H$_5$—Ph—CF=CF—Ph—CH$_2$CF$_3$
n-C$_4$H$_9$—Ph—CF=CF—Ph—CH$_2$CF$_3$
n-C$_6$H$_{13}$—Ph—CF=CF—Ph—CH$_2$CF$_3$
n-C$_8$H$_{17}$—Ph—CF=CF—Ph—CH$_2$CF$_3$
n-C$_{10}$H$_{21}$—Ph—CF=CF—Ph—CH$_2$CF$_3$
C$_2$H$_5$O—Ph—CF=CF—Ph—CH$_2$CF$_3$
n-C$_4$H$_9$O—Ph—CF=CF—Ph—CH$_2$CF$_3$
n-C$_6$H$_{13}$O—Ph—CF=CF—Ph—CH$_2$CF$_3$
n-C$_8$H$_{17}$O—Ph—CF=CF—Ph—CH$_2$CF$_3$
n-C$_{10}$H$_{21}$O—Ph—CF=CF—Ph—CH$_2$CF$_3$
C$_2$H$_5$OCH$_2$—Ph—CF=CF—Ph—CH$_2$CF$_3$
n-C$_4$H$_9$OCH$_2$—Ph—CF=CF—Ph—CH$_2$CF$_3$
n-C$_6$H$_{13}$OCH$_2$—Ph—CF=CF—Ph—CH$_2$CF$_3$
n-C$_8$H$_{17}$OCH$_2$—Ph—CF=CF—Ph—CH$_2$CF$_3$
C$_2$H$_5$—Ph—CF=CF—Ph—CF$_2$CF$_3$
n-C$_4$H$_9$—Ph—CF=CF—Ph—CF$_2$CF$_3$
n-C$_6$H$_{13}$—Ph—CF=CF—Ph—CF$_2$CF$_3$
n-C$_8$H$_{17}$—Ph—CF=CF—Ph—CF$_2$CF$_3$
n-C$_{10}$H$_{21}$—Ph—CF=CF—Ph—CF$_2$CF$_3$
C$_2$H$_5$O—Ph—CF=CF—Ph—CF$_2$CF$_3$
n-C$_4$H$_9$O—Ph—CF=CF—Ph—CF$_2$CF$_3$
n-C$_6$H$_{13}$O—Ph—CF=CF—Ph—CF$_2$CF$_3$
n-C$_8$H$_{17}$O—Ph—CF=CF—Ph—CF$_2$CF$_3$
n-C$_9$H$_{19}$O—Ph—CF=CF—Ph—CF$_2$CF$_3$
C$_2$H$_5$OCH$_2$—Ph—CF=CF—Ph—CF$_2$CF$_3$
n-C$_4$H$_9$OCH$_2$—Ph—CF=CF—Ph—CF$_2$CF$_3$
n-C$_6$H$_{13}$OCH$_2$—Ph—CF=CF—Ph—CF$_2$CF$_3$
n-C$_8$H$_{17}$OCH$_2$—Ph—CF=CF—Ph—CF$_2$CF$_3$

-continued

Trans-4-(4-methyl-trans-cyclohexyl)-4'-trifluoromethyl-α,α'-difluorostilbene

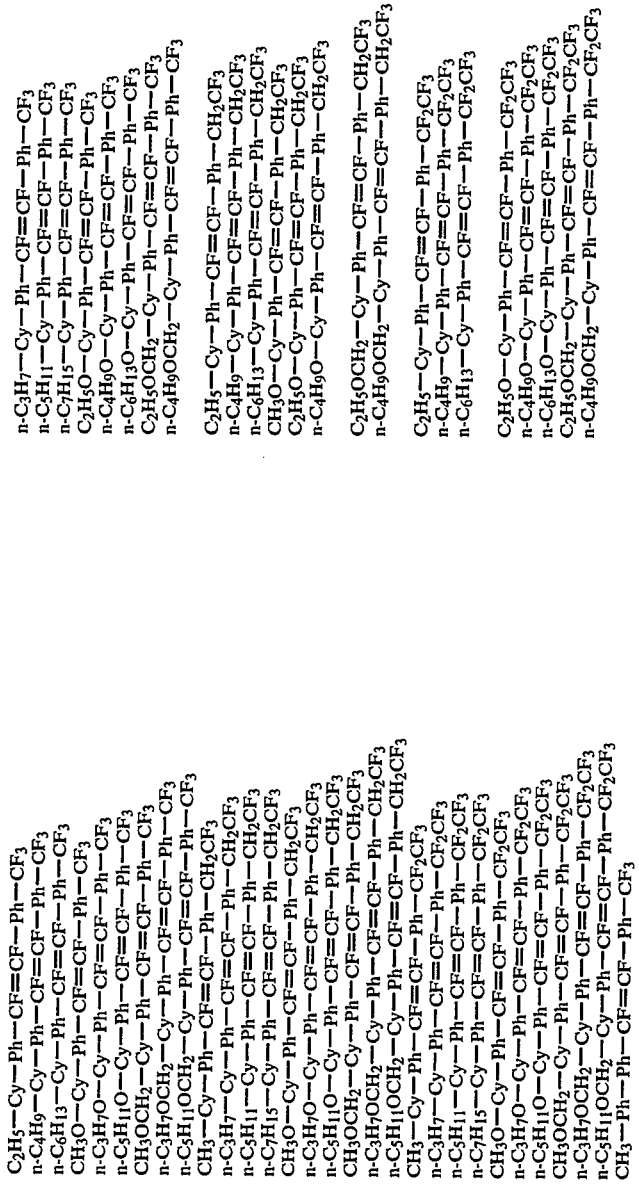

C₂H₅—Cy—Ph—CF=CF—Ph—CF₃
n-C₄H₉—Cy—Ph—CF=CF—Ph—CF₃
n-C₆H₁₃—Cy—Ph—CF=CF—Ph—CF₃
CH₃O—Cy—Ph—CF=CF—Ph—CF₃
n-C₃H₇O—Cy—Ph—CF=CF—Ph—CF₃
n-C₅H₁₁O—Cy—Ph—CF=CF—Ph—CF₃
CH₃OCH₂—Cy—Ph—CF=CF—Ph—CF₃
n-C₃H₇OCH₂—Cy—Ph—CF=CF—Ph—CF₃
n-C₅H₁₁OCH₂—Cy—Ph—CF=CF—Ph—CF₃
CH₃—Cy—Ph—CF=CF—Ph—CH₂CF₃
n-C₃H₇—Cy—Ph—CF=CF—Ph—CH₂CF₃
n-C₅H₁₁—Cy—Ph—CF=CF—Ph—CH₂CF₃
n-C₇H₁₅—Cy—Ph—CF=CF—Ph—CH₂CF₃
CH₃O—Cy—Ph—CF=CF—Ph—CH₂CF₃
n-C₃H₇O—Cy—Ph—CF=CF—Ph—CH₂CF₃
n-C₅H₁₁O—Cy—Ph—CF=CF—Ph—CH₂CF₃
CH₃OCH₂—Cy—Ph—CF=CF—Ph—CH₂CF₃
n-C₅H₁₁OCH₂—Cy—Ph—CF=CF—Ph—CH₂CF₃
CH₃—Cy—Ph—CF=CF—Ph—CF₂CF₃
n-C₃H₇—Cy—Ph—CF=CF—Ph—CF₂CF₃
n-C₅H₁₁—Cy—Ph—CF=CF—Ph—CF₂CF₃
n-C₇H₁₅—Cy—Ph—CF=CF—Ph—CF₂CF₃
CH₃O—Cy—Ph—CF=CF—Ph—CF₂CF₃
n-C₃H₇O—Cy—Ph—CF=CF—Ph—CF₂CF₃
n-C₅H₁₁O—Cy—Ph—CF=CF—Ph—CF₂CF₃
CH₃OCH₂—Cy—Ph—CF=CF—Ph—CF₂CF₃
n-C₃H₇OCH₂—Cy—Ph—CF=CF—Ph—CF₂CF₃
n-C₅H₁₁OCH₂—Cy—Ph—CF=CF—Ph—CF₂CF₃
CH₃—Ph—Ph—CF=CF—Ph—CF₃ n-C₃H₇—Cy—Ph—CF=CF—Ph—CF₃
n-C₅H₁₁—Cy—Ph—CF=CF—Ph—CF₃
n-C₇H₁₅—Cy—Ph—CF=CF—Ph—CF₃
C₂H₅O—Cy—Ph—CF=CF—Ph—CF₃
n-C₄H₉O—Cy—Ph—CF=CF—Ph—CF₃
n-C₆H₁₃O—Cy—Ph—CF=CF—Ph—CF₃
C₂H₅OCH₂—Cy—Ph—CF=CF—Ph—CF₃
n-C₄H₉OCH₂—Cy—Ph—CF=CF—Ph—CF₃

C₂H₅—Cy—Ph—CF=CF—Ph—CH₂CF₃
n-C₄H₉—Cy—Ph—CF=CF—Ph—CH₂CF₃
n-C₆H₁₃—Cy—Ph—CF=CF—Ph—CH₂CF₃
CH₃O—Cy—Ph—CF=CF—Ph—CH₂CF₃
C₂H₅O—Cy—Ph—CF=CF—Ph—CH₂CF₃
n-C₄H₉O—Cy—Ph—CF=CF—Ph—CH₂CF₃
C₂H₅OCH₂—Cy—Ph—CF=CF—Ph—CH₂CF₃
n-C₄H₉OCH₂—Cy—Ph—CF=CF—Ph—CH₂CF₃

C₂H₅—Cy—Ph—CF=CF—Ph—CF₂CF₃
n-C₄H₉—Cy—Ph—CF=CF—Ph—CF₂CF₃
n-C₆H₁₃—Cy—Ph—CF=CF—Ph—CF₂CF₃

C₂H₅O—Cy—Ph—CF=CF—Ph—CF₂CF₃
n-C₄H₉O—Cy—Ph—CF=CF—Ph—CF₂CF₃
n-C₆H₁₃O—Cy—Ph—CF=CF—Ph—CF₂CF₃
C₂H₅OCH₂—Cy—Ph—CF=CF—Ph—CF₂CF₃
n-C₄H₉OCH₂—Cy—Ph—CF=CF—Ph—CF₂CF₃

Trans-4-(4-methylphenyl)-4'-trifluoromethyl-α,α'-difluorostilbene n-C₃H₇—Ph—Ph—CF=CF—Ph—CF₃
n-C₅H₁₁—Ph—Ph—CF=CF—Ph—CF₃
n-C₇H₁₅—Ph—Ph—CF=CF—Ph—CF₃
C₂H₅O—Ph—Ph—CF=CF—Ph—CF₃

C₂H₅—Ph—Ph—CF=CF—Ph—CF₃
n-C₄H₉—Ph—Ph—CF=CF—Ph—CF₃
n-C₆H₁₃—Ph—Ph—CF=CF—Ph—CF₃
CH₃O—Ph—Ph—CF=CF—Ph—CF₃

-continued

| | |
|---|---|
| n-C₃H₇O—Ph—Ph—CF=CF—Ph—CF₃ | n-C₄H₉O—Ph—Ph—CF=CF—Ph—CF₃ |
| n-C₅H₁₁O—Ph—Ph—CF=CF—Ph—CF₃ | n-C₆H₁₃O—Ph—Ph—CF=CF—Ph—CF₃ |
| CH₃OCH₂—Ph—Ph—CF=CF—Ph—CF₃ | C₂H₅OCH₂—Ph—Ph—CF=CF—Ph—CF₃ |
| n-C₃H₇OCH₂—Ph—Ph—CF=CF—Ph—CF₃ | n-C₄H₉OCH₂—Ph—Ph—CF=CF—Ph—CF₃ |
| CH₃—Ph—Ph—CF=CF—Ph—CH₂CF₃ | C₂H₅—Ph—Ph—CF=CF—Ph—CH₂CF₃ |
| n-C₃H₇—Ph—Ph—CF=CF—Ph—CH₂CF₃ | n-C₄H₉—Ph—Ph—CF=CF—Ph—CH₂CF₃ |
| n-C₅H₁₁—Ph—Ph—CF=CF—Ph—CH₂CF₃ | n-C₆H₁₃—Ph—Ph—CF=CF—Ph—CH₂CF₃ |
| n-C₇H₁₅—Ph—Ph—CF=CF—Ph—CH₂CF₃ | |
| CH₃O—Ph—Ph—CF=CF—Ph—CH₂CF₃ | C₂H₅O—Ph—Ph—CF=CF—Ph—CH₂CF₃ |
| n-C₃H₇O—Ph—Ph—CF=CF—Ph—CH₂CF₃ | n-C₄H₉O—Ph—Ph—CF=CF—Ph—CH₂CF₃ |
| n-C₅H₁₁O—Ph—Ph—CF=CF—Ph—CH₂CF₃ | n-C₆H₁₃O—Ph—Ph—CF=CF—Ph—CH₂CF₃ |
| CH₃OCH₂—Ph—Ph—CF=CF—Ph—CH₂CF₃ | C₂H₅OCH₂—Ph—Ph—CF=CF—Ph—CH₂CF₃ |
| n-C₃H₇OCH₂—Ph—Ph—CF=CF—Ph—CH₂CF₃ | n-C₄H₉OCH₂—Ph—Ph—CF=CF—Ph—CH₂CF₃ |
| CH₃—Ph—Ph—CF=CF—Ph—CF₂CF₃ | C₂H₅—Ph—Ph—CF=CF—Ph—CF₂CF₃ |
| n-C₃H₇—Ph—Ph—CF=CF—Ph—CF₂CF₃ | n-C₄H₉—Ph—Ph—CF=CF—Ph—CF₂CF₃ |
| n-C₅H₁₁—Ph—Ph—CF=CF—Ph—CF₂CF₃ | n-C₆H₁₃—Ph—Ph—CF=CF—Ph—CF₂CF₃ |
| n-C₇H₁₅—Ph—Ph—CF=CF—Ph—CF₂CF₃ | |
| CH₃O—Ph—Ph—CF=CF—Ph—CF₂CF₃ | C₂H₅O—Ph—Ph—CF=CF—Ph—CF₂CF₃ |
| n-C₃H₇O—Ph—Ph—CF=CF—Ph—CF₂CF₃ | n-C₄H₉O—Ph—Ph—CF=CF—Ph—CF₂CF₃ |
| n-C₅H₁₁O—Ph—Ph—CF=CF—Ph—CF₂CF₃ | n-C₆H₁₃O—Ph—Ph—CF=CF—Ph—CF₂CF₃ |
| CH₃OCH₂—Ph—Ph—CF=CF—Ph—CF₂CF₃ | C₂H₅OCH₂—Ph—Ph—CF=CF—Ph—CF₂CF₃ |
| n-C₃H₇OCH₂—Ph—Ph—CF=CF—Ph—CF₂CF₃ | n-C₄H₉OCH₂—Ph—Ph—CF=CF—Ph—CF₂CF₃ |
| CH₃—Ph—CF=CF—Ph—Ph—CF₃ | C₂H₅—Ph—CF=CF—Ph—Ph—CF₃ |
| n-C₃H₇—Ph—CF=CF—Ph—Ph—CF₃ | n-C₄H₉—Ph—CF=CF—Ph—Ph—CF₃ |
| n-C₅H₁₁—Ph—CF=CF—Ph—Ph—CF₃ | n-C₆H₁₃—Ph—CF=CF—Ph—Ph—CF₃ |
| n-C₇H₁₅—Ph—CF=CF—Ph—Ph—CF₃ | |
| CH₃O—Ph—CF=CF—Ph—Ph—CF₃ | C₂H₅O—Ph—CF=CF—Ph—Ph—CF₃ |
| n-C₃H₇O—Ph—CF=CF—Ph—Ph—CF₃ | n-C₄H₉O—Ph—CF=CF—Ph—Ph—CF₃ |
| n-C₅H₁₁O—Ph—CF=CF—Ph—Ph—CF₃ | n-C₆H₁₃O—Ph—CF=CF—Ph—Ph—CF₃ |
| CH₃OCH₂—Ph—CF=CF—Ph—Ph—CF₃ | C₂H₅OCH₂—Ph—CF=CF—Ph—Ph—CF₃ |
| n-C₃H₇OCH₂—Ph—CF=CF—Ph—Ph—CF₃ | n-C₄H₉OCH₂—Ph—CF=CF—Ph—Ph—CF₃ |
| CH₃—Ph—CF=CF—Ph—Ph—CH₂CF₃ | C₂H₅—Ph—CF=CF—Ph—Ph—CH₂CF₃ |
| n-C₃H₇—Ph—CF=CF—Ph—Ph—CH₂CF₃ | n-C₄H₉—Ph—CF=CF—Ph—Ph—CH₂CF₃ |
| n-C₅H₁₁—Ph—CF=CF—Ph—Ph—CH₂CF₃ | n-C₆H₁₃—Ph—CF=CF—Ph—Ph—CH₂CF₃ |
| n-C₇H₁₅—Ph—CF=CF—Ph—Ph—CH₂CF₃ | |
| CH₃O—Ph—CF=CF—Ph—Ph—CH₂CF₃ | C₂H₅O—Ph—CF=CF—Ph—Ph—CH₂CF₃ |
| n-C₃H₇O—Ph—CF=CF—Ph—Ph—CH₂CF₃ | n-C₄H₉O—Ph—CF=CF—Ph—Ph—CH₂CF₃ |
| n-C₅H₁₁O—Ph—CF=CF—Ph—Ph—CH₂CF₃ | n-C₆H₁₃O—Ph—CF=CF—Ph—Ph—CH₂CF₃ |
| CH₃OCH₂—Ph—CF=CF—Ph—Ph—CH₂CF₃ | C₂H₅OCH₂—Ph—CF=CF—Ph—Ph—CH₂CF₃ |
| n-C₃H₇OCH₂—Ph—CF=CF—Ph—Ph—CH₂CF₃ | n-C₄H₉OCH₂—Ph—CF=CF—Ph—Ph—CH₂CF₃ |
| CH₃—Ph—CF=CF—Ph—Ph—CF₂CF₃ | C₂H₅—Ph—CF=CF—Ph—Ph—CF₂CF₃ |
| n-C₃H₇—Ph—CF=CF—Ph—Ph—CF₂CF₃ | n-C₄H₉—Ph—CF=CF—Ph—Ph—CF₂CF₃ |
| n-C₅H₁₁—Ph—CF=CF—Ph—Ph—CF₂CF₃ | n-C₆H₁₃—Ph—CF=CF—Ph—Ph—CF₂CF₃ |
| n-C₇H₁₅—Ph—CF=CF—Ph—Ph—CF₂CF₃ | |
| CH₃O—Ph—CF=CF—Ph—Ph—CF₂CF₃ | C₂H₅O—Ph—CF=CF—Ph—Ph—CF₂CF₃ |
| n-C₃H₇O—Ph—CF=CF—Ph—Ph—CF₂CF₃ | n-C₄H₉O—Ph—CF=CF—Ph—Ph—CF₂CF₃ |
| n-C₅H₁₁O—Ph—CF=CF—Ph—Ph—CF₂CF₃ | n-C₆H₁₃O—Ph—CF=CF—Ph—Ph—CF₂CF₃ |
| CH₃OCH₂—Ph—CF=CF—Ph—Ph—CF₂CF₃ | C₂H₅OCH₂—Ph—CF=CF—Ph—Ph—CF₂CF₃ |

-continued n-C₃H₇OCH₂—Ph—CF=CF—Ph—Ph—CF₂CF₃
n-C₅H₁₁OCH₂—Ph—CF=CF—Ph—Ph—CF₂CF₃
CH₃—Cy—CH₂CH₂—Ph—CF=CF—Ph—CF₃ n-C₄H₉OCH₂—Ph—CF=CF—Ph—Ph—CF₂CF₃

Trans-4-[2-(4-methyl-trans-cyclohexyl)ethyl]-4'-trifluoromethyl-α,α'-difluorostilbene

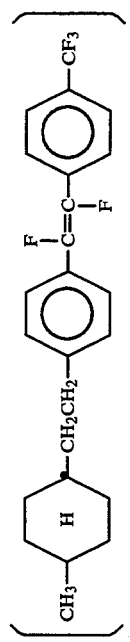

C₂H₅—Cy—CH₂CH₂—Ph—CF=CF—Ph—CF₃
n-C₄H₉—Cy—CH₂CH₂—Ph—CF=CF—Ph—CF₃
n-C₆H₁₃—Cy—CH₂CH₂—Ph—CF=CF—Ph—CF₃
CH₃O—Cy—CH₂CH₂—Ph—CF=CF—Ph—CF₃
n-C₃H₇O—Cy—CH₂CH₂—Ph—CF=CF—Ph—CF₃
n-C₅H₁₁O—Cy—CH₂CH₂—Ph—CF=CF—Ph—CF₃
CH₃OCH₂—Cy—CH₂CH₂—Ph—CF=CF—Ph—CF₃
n-C₃H₇OCH₂—Cy—CH₂CH₂—Ph—CF=CF—Ph—CF₃
n-C₅H₁₁OCH₂—Cy—CH₂CH₂—Ph—CF=CF—Ph—CF₃
CH₃—Cy—CH₂CH₂—Ph—CF=CF—Ph—CH₂CF₃
n-C₃H₇—Cy—CH₂CH₂—Ph—CF=CF—Ph—CH₂CF₃
n-C₅H₁₁—Cy—CH₂CH₂—Ph—CF=CF—Ph—CH₂CF₃
n-C₇H₁₅—Cy—CH₂CH₂—Ph—CF=CF—Ph—CH₂CF₃
CH₃O—Cy—CH₂CH₂—Ph—CF=CF—Ph—CH₂CF₃
n-C₅H₁₁O—Cy—CH₂CH₂—Ph—CF=CF—Ph—CH₂CF₃
CH₃OCH₂—Cy—CH₂CH₂—Ph—CF=CF—Ph—CH₂CF₃
n-C₃H₇OCH₂—Cy—CH₂CH₂—Ph—CF=CF—Ph—CH₂CF₃
n-C₄H₉OCH₂—Cy—CH₂CH₂—Ph—CF=CF—Ph—CH₂CF₃
n-C₅H₁₁OCH₂—Cy—CH₂CH₂—Ph—CF=CF—Ph—CH₂CF₃
CH₃—Cy—CH₂CH₂—Cy—CH₂CH₂—Ph—CF=CF—Ph—CF₂CF₃ n-C₃H₇—Cy—CH₂CH₂—Ph—CF=CF—Ph—CF₂CF₃
n-C₅H₁₁—Cy—CH₂CH₂—Ph—CF=CF—Ph—CF₃
n-C₇H₁₅—Cy—CH₂CH₂—Ph—CF=CF—Ph—CF₃
C₂H₅O—Cy—CH₂CH₂—Ph—CF=CF—Ph—CF₃
n-C₄H₉O—Cy—CH₂CH₂—Ph—CF=CF—Ph—CF₃
n-C₆H₁₃O—Cy—CH₂CH₂—Ph—CF=CF—Ph—CF₃
C₂H₅OCH₂—Cy—CH₂CH₂—Ph—CF=CF—Ph—CF₃
n-C₄H₉OCH₂—Cy—CH₂CH₂—Ph—CF=CF—Ph—CF₃

C₂H₅—Cy—CH₂CH₂—Ph—CF=CF—Ph—CH₂CF₃
n-C₄H₉—Cy—CH₂CH₂—Ph—CF=CF—Ph—CH₂CF₃
n-C₆H₁₃—Cy—CH₂CH₂—Ph—CF=CF—Ph—CH₂CF₃

C₂H₅O—Cy—CH₂CH₂—Ph—CF=CF—Ph—CH₂CF₃
n-C₄H₉O—Cy—CH₂CH₂—Ph—CF=CF—Ph—CH₂CF₃

C₂H₅OCH₂—Cy—CH₂CH₂—Ph—CF=CF—Ph—CH₂CF₃

C₂H₅O—Cy—CH₂CH₂—Ph—CF=CF—Ph—CF₂CF₃
n-C₄H₉O—Cy—CH₂CH₂—Ph—CF=CF—Ph—CF₂CF₃
n-C₆H₁₃O—Cy—CH₂CH₂—Ph—CF=CF—Ph—CF₂CF₃
C₂H₅OCH₂—Cy—CH₂CH₂—Ph—CF=CF—Ph—CF₂CF₃

Trans-4-(4-methyl-trans-cyclohexyl)methoxy-4'-trifluoromethyl-α,α'-difluorostilbene -continued

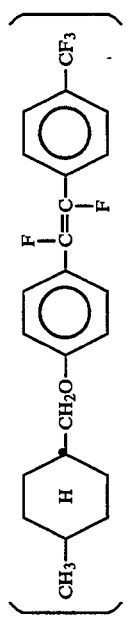

C2H5—Cy—CH2O—Ph—CF=CF—Ph—CF3
n-C4H9—Cy—CH2O—Ph—CF=CF—Ph—CF3
n-C6H13—Cy—CH2O—Ph—CF=CF—Ph—CF3
CH3O—Cy—CH2O—Ph—CF=CF—Ph—CF3
n-C3H7O—Cy—CH2O—Ph—CF=CF—Ph—CF3
n-C5H11O—Cy—CH2O—Ph—CF=CF—Ph—CF3
CH3—Cy—OCH2—Ph—CF=CF—Ph—CF3
n-C3H7—Cy—OCH2—Ph—CF=CF—Ph—CF3
n-C5H11—Cy—OCH2—Ph—CF=CF—Ph—CF3
CH3—Cy—COO—Ph—CF=CF—Ph—CF3
n-C3H7—Cy—COO—Ph—CF=CF—Ph—CF3
n-C5H11—Cy—COO—Ph—CF=CF—Ph—CF3
CH3—Cy—C≡C—Ph—CF=CF—Ph—CF3
n-C3H7—Cy—C≡C—Ph—CF=CF—Ph—CF3
n-C5H11—Cy—C≡C—Ph—CF=CF—Ph—CF3
CH3O—Cy—C≡C—Ph—CF=CF—Ph—CF3
n-C3H7O—Cy—C≡C—Ph—CF=CF—Ph—CF3
n-C5H11O—Cy—C≡C—Ph—CF=CF—Ph—CF3 n-C3H7—Cy—CH2O—Ph—CF=CF—Ph—CF3
n-C5H11—Cy—CH2O—Ph—CF=CF—Ph—CF3

C2H5O—Cy—CH2O—Ph—CF=CF—Ph—CF3
n-C4H9O—Cy—CH2O—Ph—CF=CF—Ph—CF3

C2H5—Cy—OCH2—Ph—CF=CF—Ph—CF3
n-C4H9—Cy—OCH2—Ph—CF=CF—Ph—CF3
n-C6H13—Cy—OCH2—Ph—CF=CF—Ph—CF3
C2H5—Cy—COO—Ph—CF=CF—Ph—CF3
n-C4H9—Cy—COO—Ph—CF=CF—Ph—CF3
n-C6H13—Cy—COO—Ph—CF=CF—Ph—CF3
C2H5—Cy—C≡C—Ph—CF=CF—Ph—CF3
n-C4H9—Cy—C≡C—Ph—CF=CF—Ph—CF3
n-C6H13—Cy—C≡C—Ph—CF=CF—Ph—CF3
C2H5O—Cy—C≡C—Ph—CF=CF—Ph—CF3
n-C4H9O—Cy—C≡C—Ph—CF=CF—Ph—CF3

Further, the following compounds can be prepared by changing tetrafluoroethylene to chlorotrifluoroethylene, perfuluoro-2-butene or perfluoropropene.

CH₃—Ph—CF=CCl—Ph—CF₃
Trans-4-methyl-4'-trifluoromethyl-α-fluoro-α'-chlorostilbene

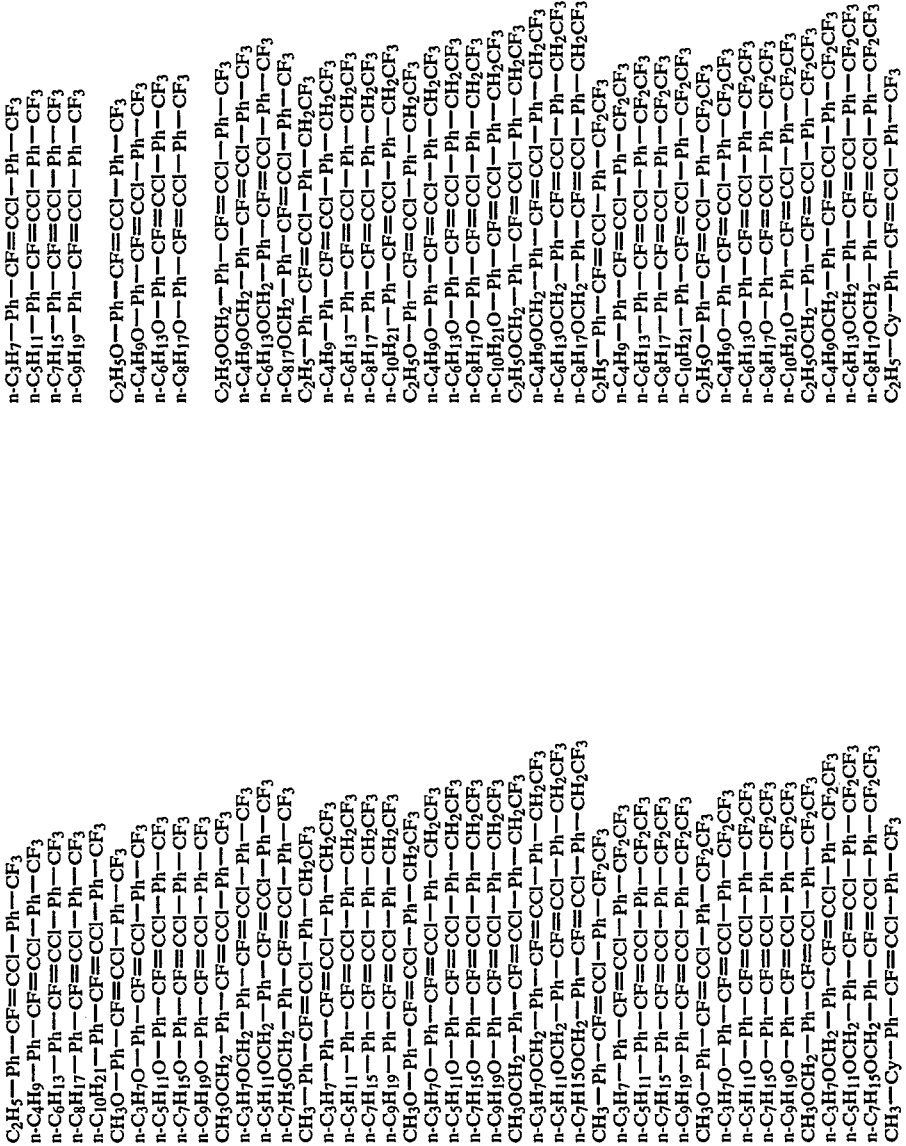

Figure 15:
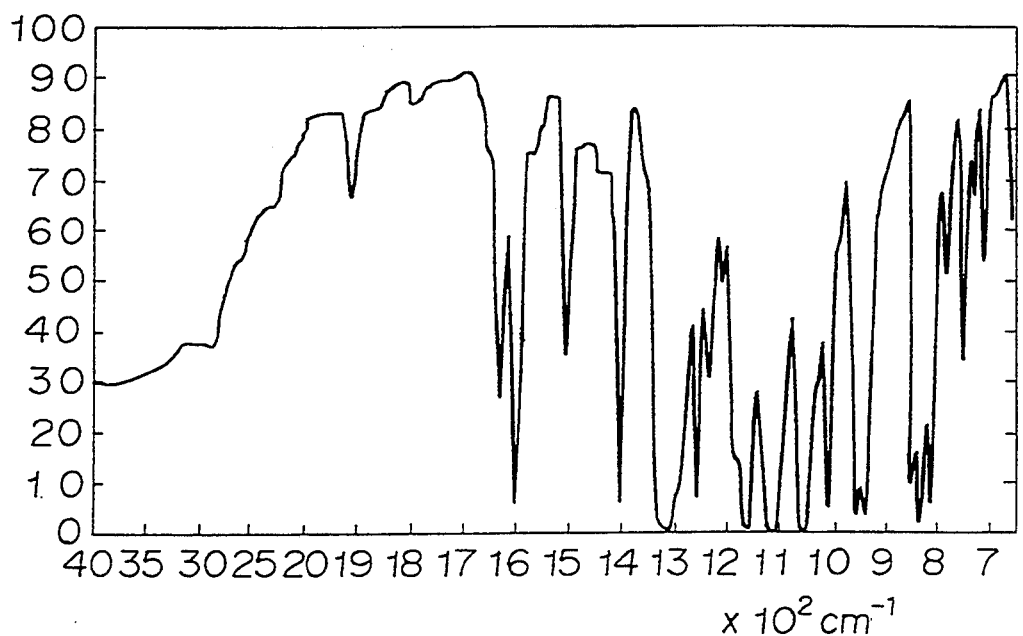

(m.p. 95.1° C, IR spectrum: shown in FIG. 15)

C₂H₅—Ph—CF=CCl—Ph—CF₃
n-C₄H₉—Ph—CF=CCl—Ph—CF₃
n-C₆H₁₃—Ph—CF=CCl—Ph—CF₃
n-C₈H₁₇—Ph—CF=CCl—Ph—CF₃
n-C₁₀H₂₁—Ph—CF=CCl—Ph—CF₃
CH₃O—Ph—CF=CCl—Ph—CF₃
n-C₃H₇O—Ph—CF=CCl—Ph—CF₃
n-C₅H₁₁O—Ph—CF=CCl—Ph—CF₃
n-C₇H₁₅O—Ph—CF=CCl—Ph—CF₃
n-C₉H₁₉O—Ph—CF=CCl—Ph—CF₃
CH₃OCH₂—Ph—CF=CCl—Ph—CF₃
n-C₃H₇OCH₂—Ph—CF=CCl—Ph—CF₃
n-C₅H₁₁OCH₂—Ph—CF=CCl—Ph—CF₃
n-C₇H₁₅OCH₂—Ph—CF=CCl—Ph—CF₃
CH₃—Ph—CF=CCl—Ph—CH₂CF₃
n-C₃H₇—Ph—CF=CCl—Ph—CH₂CF₃
n-C₅H₁₁—Ph—CF=CCl—Ph—CH₂CF₃
n-C₇H₁₅—Ph—CF=CCl—Ph—CH₂CF₃
n-C₉H₁₉—Ph—CF=CCl—Ph—CH₂CF₃
CH₃O—Ph—CF=CCl—Ph—CH₂CF₃
n-C₃H₇O—Ph—CF=CCl—Ph—CH₂CF₃
n-C₅H₁₁O—Ph—CF=CCl—Ph—CH₂CF₃
n-C₇H₁₅O—Ph—CF=CCl—Ph—CH₂CF₃
n-C₉H₁₉O—Ph—CF=CCl—Ph—CH₂CF₃
CH₃OCH₂—Ph—CF=CCl—Ph—CH₂CF₃
n-C₃H₇OCH₂—Ph—CF=CCl—Ph—CH₂CF₃
n-C₅H₁₁OCH₂—Ph—CF=CCl—Ph—CH₂CF₃
n-C₇H₁₅OCH₂—Ph—CF=CCl—Ph—CH₂CF₃
CH₃—Ph—CF=CCl—Ph—CF₂CF₃
n-C₃H₇—Ph—CF=CCl—Ph—CF₂CF₃
n-C₅H₁₁—Ph—CF=CCl—Ph—CF₂CF₃
n-C₇H₁₅—Ph—CF=CCl—Ph—CF₂CF₃
n-C₉H₁₉—Ph—CF=CCl—Ph—CF₂CF₃
CH₃O—Ph—CF=CCl—Ph—CF₂CF₃
n-C₃H₇O—Ph—CF=CCl—Ph—CF₂CF₃
n-C₅H₁₁O—Ph—CF=CCl—Ph—CF₂CF₃
n-C₇H₁₅O—Ph—CF=CCl—Ph—CF₂CF₃
n-C₃H₇OCH₂—Ph—CF=CCl—Ph—CF₂CF₃
n-C₅H₁₁OCH₂—Ph—CF=CCl—Ph—CF₂CF₃
n-C₇H₁₅OCH₂—Ph—CF=CCl—Ph—CF₂CF₃
CH₃—Cy—Ph—CF=CCl—Ph—CF₃ n-C₃H₇—Ph—CF=CCl—Ph—CF₃
n-C₅H₁₁—Ph—CF=CCl—Ph—CF₃
n-C₇H₁₅—Ph—CF=CCl—Ph—CF₃
n-C₉H₁₉—Ph—CF=CCl—Ph—CF₃

C₂H₅O—Ph—CF=CCl—Ph—CF₃
n-C₄H₉O—Ph—CF=CCl—Ph—CF₃
n-C₆H₁₃O—Ph—CF=CCl—Ph—CF₃
n-C₈H₁₇O—Ph—CF=CCl—Ph—CF₃

C₂H₅OCH₂—Ph—CF=CCl—Ph—CF₃
n-C₄H₉OCH₂—Ph—CF=CCl—Ph—CF₃
n-C₆H₁₃OCH₂—Ph—CF=CCl—Ph—CF₃
n-C₈H₁₇OCH₂—Ph—CF=CCl—Ph—CF₃
C₂H₅—Ph—CF=CCl—Ph—CH₂CF₃
n-C₄H₉—Ph—CF=CCl—Ph—CH₂CF₃
n-C₆H₁₃—Ph—CF=CCl—Ph—CH₂CF₃
n-C₈H₁₇—Ph—CF=CCl—Ph—CH₂CF₃
n-C₁₀H₂₁—Ph—CF=CCl—Ph—CH₂CF₃
C₂H₅O—Ph—CF=CCl—Ph—CH₂CF₃
n-C₄H₉O—Ph—CF=CCl—Ph—CH₂CF₃
n-C₆H₁₃O—Ph—CF=CCl—Ph—CH₂CF₃
n-C₈H₁₇O—Ph—CF=CCl—Ph—CH₂CF₃
n-C₁₀H₂₁O—Ph—CF=CCl—Ph—CH₂CF₃
C₂H₅OCH₂—Ph—CF=CCl—Ph—CH₂CF₃
n-C₄H₉OCH₂—Ph—CF=CCl—Ph—CH₂CF₃
n-C₆H₁₃OCH₂—Ph—CF=CCl—Ph—CH₂CF₃
n-C₈H₁₇OCH₂—Ph—CF=CCl—Ph—CH₂CF₃
C₂H₅—Ph—CF=CCl—Ph—CF₂CF₃
n-C₄H₉—Ph—CF=CCl—Ph—CF₂CF₃
n-C₆H₁₃—Ph—CF=CCl—Ph—CF₂CF₃
n-C₈H₁₇—Ph—CF=CCl—Ph—CF₂CF₃
n-C₁₀H₂₁—Ph—CF=CCl—Ph—CF₂CF₃
C₂H₅O—Ph—CF=CCl—Ph—CF₂CF₃
n-C₄H₉O—Ph—CF=CCl—Ph—CF₂CF₃
n-C₆H₁₃O—Ph—CF=CCl—Ph—CF₂CF₃
n-C₈H₁₇O—Ph—CF=CCl—Ph—CF₂CF₃
n-C₁₀H₂₁O—Ph—CF=CCl—Ph—CF₂CF₃
C₂H₅OCH₂—Ph—CF=CCl—Ph—CF₂CF₃
n-C₄H₉OCH₂—Ph—CF=CCl—Ph—CF₂CF₃
n-C₆H₁₃OCH₂—Ph—CF=CCl—Ph—CF₂CF₃
n-C₈H₁₇OCH₂—Ph—CF=CCl—Ph—CF₂CF₃
C₂H₅—Cy—Ph—CF=CCl—Ph—CF₂CF₃

-continued n-C3H7—Cy—Ph—CF=CCl—Ph—CF3
n-C5H11—Cy—Ph—CF=CCl—Ph—CF3
n-C7H15—Cy—Ph—CF=CCl—Ph—CF3
CH3O—Cy—Ph—CF=CCl—Ph—CF3
n-C3H7O—Cy—Ph—CF=CCl—Ph—CF3
n-C5H11O—Cy—Ph—CF=CCl—Ph—CF3
CH3OCH2—Cy—Ph—CF=CCl—Ph—CF3
n-C3H7OCH2—Cy—Ph—CF=CCl—Ph—CF3
n-C5H11OCH2—Cy—Ph—CF=CCl—Ph—CF3
CH3—Cy—Ph—CF=CCl—Ph—CH2CF3
n-C3H7—Cy—Ph—CF=CCl—Ph—CH2CF3
n-C5H11—Cy—Ph—CF=CCl—Ph—CH2CF3
CH3O—Cy—Ph—CF=CCl—Ph—CH2CF3
n-C5H11O—Cy—Ph—CF=CCl—Ph—CH2CF3
CH3—Ph—Ph—CF=CCl—Ph—CF3
n-C3H7—Ph—Ph—CF=CCl—Ph—CF3
n-C5H11—Ph—Ph—CF=CCl—Ph—CF3
n-C7H15—Ph—Ph—CF=CCl—Ph—CF3
CH3O—Ph—Ph—CF=CCl—Ph—CF3
n-C3H7O—Ph—Ph—CF=CCl—Ph—CF3
n-C5H11O—Ph—Ph—CF=CCl—Ph—CF3
CH3—Ph—Ph—CF=CCl—Ph—CH2CF3
n-C3H7—Ph—Ph—CF=CCl—Ph—CH2CF3
n-C5H11—Ph—Ph—CF=CCl—Ph—CH2CF3
CH3O—Ph—Ph—CF=CCl—Ph—CH2CF3
n-C5H11O—Ph—Ph—CF=CCl—Ph—CH2CF3
CH3—Cy—CH2CH2—Ph—CF=CCl—Ph—CF3
n-C3H7—Cy—CH2CH2—Ph—CF=CCl—Ph—CF3
n-C5H11—Cy—CH2CH2—Ph—CF=CCl—Ph—CF3
n-C7H15—Cy—CH2CH2—Ph—CF=CCl—Ph—CF3
CH3O—Cy—CH2CH2—Ph—CF=CCl—Ph—CF3
n-C3H7O—Cy—CH2CH2—Ph—CF=CCl—Ph—CF3
n-CF5H11O—Cy—CH2CH2—Ph—CF=CCl—Ph—CF3
CH3—Cy—CH2CH2—Ph—CF=CCl—Ph—CH2CF3
n-C3H7—Cy—CH2CH2—Ph—CF=CCl—Ph—CH2CF3
n-C5H11—Cy—CH2CH2—Ph—CF=CCl—Ph—CH2CF3
CH3O—Cy—CH2CH2—Ph—CF=CCl—Ph—CH2CF3
n-C3H7O—Cy—CH2CH2—Ph—CF=CCl—Ph—CH2CF3
n-C5H11O—Cy—CH2CH2—Ph—CF=CCl—Ph—CH2CF3
CH3OCH2—Cy—CH2CH2—Ph—CF=CCl—Ph—CH2CF3
n-C4H9OCH2—Cy—CH2CH2—Ph—CF=CCl—Ph—CH2CF3
n-C5H11OCH2—Cy—CH2CH2—Ph—CF=CCl—Ph—CH2CF3
CH3—Ph—CCl=CF—Ph—CF3
n-C3H7—Ph—CCl=CF—Ph—CF3
n-C5H11—Ph—CCl=CF—Ph—CF3
n-C7H15—Ph—CCl=CF—Ph—CF3
n-C9H19—Ph—CCl=CF—Ph—CF3
CH3O—Ph—CCl=CF—Ph—CF3
n-C5H11O—Ph—CCl=CF—Ph—CF3 n-C4H9—Cy—Ph—CF=CCl—Ph—CF3
n-C6H13—Cy—Ph—CF=CCl—Ph—CF3

C2H5O—Cy—Ph—CF=CCl—Ph—CF3
n-C4H9O—Cy—Ph—CF=CCl—Ph—CF3
n-C6H13O—Cy—Ph—CF=CCl—Ph—CF3
C2H5OCH2—Cy—Ph—CF=CCl—Ph—CF3
n-C4H9OCH2—Cy—Ph—CF=CCl—Ph—CF3

C2H5—C3—Ph—CF=CCl—Ph—CH2CF3
n-C4H9—Cy—Ph—CF=CCl—Ph—CH2CF3

C2H5O—Cy—Ph—CF=CCl—Ph—CH2CF3
n-C4H9O—Cy—Ph—CF=CCl—Ph—CH2CF3

C2H5—Ph—Ph—CF=CCl—Ph—CF3
n-C4H9—Ph—Ph—CF=CCl—Ph—CF3
n-C6H13—Ph—Ph—CF=CCl—Ph—CF3

C2H5O—Ph—Ph—CF=CCl—Ph—CF3
n-C4H9O—Ph—Ph—CF=CCl—Ph—CF3
n-C6H13O—Ph—Ph—CF=CCl—Ph—CF3
C2H5—Ph—Ph—CF=CCl—Ph—CH2CF3
n-C4H9—Ph—Ph—CF=CCl—Ph—CH2CF3
n-C6H13—Ph—Ph—CF=CCl—Ph—CH2CF3
C2H5O—Ph—Ph—CF=CCl—Ph—CH2CF3
n-C4H9O—Ph—Ph—CF=CCl—Ph—CH2CF3

C2H5—Cy—CH2CH2—Ph—CF=CCl—Ph—CF3
n-C4H9—Cy—CH2CH2—Ph—CF=CCl—Ph—CF3
n-C6H13—Cy—CH2CH2—Ph—CF=CCl—Ph—CF3

C2H5O—Cy—CH2CH2—Ph—CF=CCl—Ph—CF3
n-C4H9O—Cy—CH2CH2—Ph—CF=CCl—Ph—CF3

C2H5—Cy—CH2CH2—Ph—CF=CCl—Ph—CH2CF3
n-C4H9—Cy—CH2CH2—Ph—CF=CCl—Ph—CH2CF3
n-C6H13—Cy—CH2CH2—Ph—CF=CCl—Ph—CH2CF3

C2H5O—Cy—CH2CH2—Ph—CF=CCl—Ph—CH2CF3
n-C4H9O—Cy—CH2CH2—Ph—CF=CCl—Ph—CH2CF3

C2H5OCH2—Cy—CH2CH2—Ph—CF=CCl—Ph—CH2CF3

C2H5—Ph—CCl=CF—Ph—CF3
n-C4H9—Ph—CCl=CF—Ph—CF3
n-C6H13—Ph—CCl=CF—Ph—CF3
n-C8H17—Ph—CCl=CF—Ph—CF3
n-C10H21—Ph—CCl=CF—Ph—CF3
C2H5O—Ph—CCl=CF—Ph—CF3
n-C4H9O—Ph—CCl=CF—Ph—CF3
n-C6H13O—Ph—CCl=CF—Ph—CF3

-continued n-C₇H₁₅O—Ph—CCl=CF—Ph—CF₃
n-C₉H₁₉O—Ph—CCl=CF—Ph—CF₃
CH₃OCH₂—Ph—CCl=CF—Ph—CF₃
n-C₃H₇OCH₂—Ph—CCl=CF—Ph—CF₃
n-C₅H₁₁OCH₂—Ph—CCl=CF—Ph—CF₃
n-C₇H₁₅OCH₂—Ph—CCl=CF—Ph—CF₃
CH₃—Ph—CCl=CF—Ph—CH₂CF₃
n-C₃H₇—Ph—CCl=CF—Ph—CH₂CF₃
n-C₅H₁₁—Ph—CCl=CF—Ph—CH₂CF₃
n-C₇H₁₅—Ph—CCl=CF—Ph—CH₂CF₃
n-C₉H₁₉—Ph—CCl=CF—Ph—CH₂CF₃
n-C₁₀H₂₁—Ph—CCl=CF—Ph—CH₂CF₃
CH₃O—Ph—CCl=CF—Ph—CH₂CF₃
n-C₃H₇O—Ph—CCl=CF—Ph—CH₂CF₃
n-C₅H₁₁O—Ph—CCl=CF—Ph—CH₂CF₃
n-C₇H₁₅O—Ph—CCl=CF—Ph—CH₂CF₃
n-C₉H₁₉O—Ph—CCl=CF—Ph—CH₂CF₃
CH₃OCH₂—Ph—CCl=CF—Ph—CH₂CF₃
n-C₃H₇OCH₂—Ph—CCl=CF—Ph—CH₂CF₃
n-C₅H₁₁OCH₂—Ph—CCl=CF—Ph—CH₂CF₃
n-C₇H₁₅OCH₂—Ph—CCl=CF—Ph—CH₂CF₃
CH₃—Ph—CCl=CF—Ph—CF₂CF₃
n-C₃H₇—Ph—CCl=CF—Ph—CF₂CF₃
n-C₅H₁₁—Ph—CCl=CF—Ph—CF₂CF₃
n-C₇H₁₅—Ph—CCl=CF—Ph—CF₂CF₃ n-C₈H₁₇O—Ph—CCl=CF—Ph—CF₃

C₂H₅OCH₂—Ph—CCl=CF—Ph—CF₃
n-C₄H₉OCH₂—Ph—CCl=CF—Ph—CF₃
n-C₆H₁₃OCH₂—Ph—CCl=CF—Ph—CF₃
n-C₈H₁₇OCH₂—Ph—CCl=CF—Ph—CF₃
C₂H₅—Ph—CCl=CF—Ph—CH₂CF₃,
n-C₄H₉—Ph—CCl=CF—Ph—CH₂CF₃
n-C₆H₁₃—Ph—CCl=CF—Ph—CH₂CF₃
n-C₈H₁₇—Ph—CCl=CF—Ph—CH₂CF₃
n-C₁₀H₂₁—Ph—CCl=CF—Ph—CH₂CF₃
CH₃O—Ph—CCl=CF—Ph—CH₂CF₃
C₂H₅O—Ph—CCl=CF—Ph—CH₂CF₃
n-C₄H₉O—Ph—CCl=CF—Ph—CH₂CF₃
n-C₆H₁₃O—Ph—CCl=CF—Ph—CH₂CF₃
n-C₈H₁₇O—Ph—CCl=CF—Ph—CH₂CF₃
C₂H₅OCH₂—Ph—CCl=CF—Ph—CH₂CF₃
n-C₄H₉OCH₂—Ph—CCl=CF—Ph—CH₂CF₃
n-C₆H₁₃OCH₂—Ph—CCl=CF—Ph—CH₂CF₃
n-C₈H₁₇OCH₂—Ph—CCl=CF—Ph—CH₂CF₃
C₂H₅—Ph—CCl=CF—Ph—CF₂CF₃
n-C₄H₉—Ph—CCl=CF—Ph—CF₂CF₃
n-C₆H₁₃—Ph—CCl=CF—Ph—CF₂CF₃
n-C₈H₁₇—Ph—CCl=CF—Ph—CF₂CF₃ n-C₆H₁₉—Ph—CCl=CF—Ph—CF₂CF₃
CH₃O—Ph—CCl=CF—Ph—CF₂CF₃
n-C₃H₇O—Ph—CCl=CF—Ph—CF₂CF₃
n-C₅H₁₁O—Ph—CCl=CF—Ph—CF₂CF₃
n-C₇H₁₅O—Ph—CCl=CF—Ph—CF₂CF₃
n-C₉H₁₉O—Ph—CCl=CF—Ph—CF₂CF₃
CH₃OCH₂—Ph—CCl=CF—Ph—CF₂CF₃
n-C₃H₇OCH₂—Ph—CCl=CF—Ph—CF₂CF₃
n-C₅H₁₁OCH₂—Ph—CCl=CF—Ph—CF₂CF₃
n-C₇H₁₅OCH₂—Ph—CCl=CF—Ph—CF₂CF₃
CH₃—Cy—Ph—CCl=CF—Ph—CF₃
n-C₃H₇—Cy—Ph—CCl=CF—Ph—CF₃
n-C₅H₁₁—Cy—Ph—CCl=CF—Ph—CF₃
n-C₇H₁₅—Cy—Ph—CCl=CF—Ph—CF₃
CH₃O—Cy—Ph—CCl=CF—Ph—CF₃
n-C₃H₇O—Cy—Ph—CCl=CF—Ph—CF₃
n-C₅H₁₁O—Cy—Ph—CCl=CF—Ph—CF₃
CH₃OCH₂—Cy—Ph—CCl=CF—Ph—CF₃
n-C₃H₇OCH₂—Cy—Ph—CCl=CF—Ph—CF₃
n-C₅H₁₁OCH₂—Cy—Ph—CCl=CF—Ph—CF₃
CH₃—Cy—Ph—CCl=CF—Ph—CH₂CF₃
n-C₃H₇—Cy—Ph—CCl=CF—Ph—CH₂CF₃
C₂H₅O—Ph—Ph—CCl=CF—Ph—CF₃
n-C₄H₉O—Ph—Ph—CCl=CF—Ph—CF₃
n-C₆H₁₃O—Ph—Ph—CCl=CF—Ph—CF₃
CH₃—Ph—Ph—CCl=CF—Ph—CH₂CF₃
n-C₃H₇—Ph—Ph—CCl=CF—Ph—CH₂CF₃
n-C₅H₁₁—Ph—Ph—CCl=CF—Ph—CH₂CF₃
CH₃O—Ph—Ph—CCl=CF—Ph—CH₂CF₃
n-C₃H₇O—Ph—Ph—CCl=CF—Ph—CH₂CF₃
n-C₅H₁₁O—Ph—Ph—CCl=CF—Ph—CH₂CF₃
CH₃—Cy—CH₂CH₂—Ph—CCl=CF—Ph—CF₃
n-C₃H₇—Cy—CH₂CH₂—Ph—CCl=CF—Ph—CF₃
n-C₅H₁₁—Cy—CH₂CH₂—Ph—CCl=CF—Ph—CF₃
n-C₇H₁₅—Cy—CH₂CH₂—Ph—CCl=CF—Ph—CF₃
CH₃O—Cy—CH₂CH₂—Ph—CCl=CF—Ph—CF₃
n-C₃H₇O—Cy—CH₂CH₂—Ph—CCl=CF—Ph—CF₃
n-C₅H₁₁O—Cy—CH₂CH₂—Ph—CCl=CF—Ph—CF₃
CH₃—Cy—CH₂CH₂—Ph—CCl=CF—Ph—CH₂CF₃
n-C₃H₇—Cy—CH₂CH₂—Ph—CCl=CF—Ph—CH₂CF₃
n-C₅H₁₁—Cy—CH₂CH₂—Ph—CCl=CF—Ph—CH₂CF₃
CH₃O—Cy—CH₂CH₂—Ph—CCl=CF—Ph—CH₂CF₃
n-C₃H₇O—Cy—CH₂CH₂—Ph—CCl=CF—Ph—CH₂CF₃
n-C₅H₁₁O—Cy—CH₂CH₂—Ph—CCl=CF—Ph—CH₂CF₃
CH₃—Ph—CCl=CCl—Ph—CF₃
n-C₃H₇—Ph—CCl=CCl—Ph—CF₃
n-C₅H₁₁—Ph—CCl=CCl—Ph—CF₃
n-C₇H₁₅—Ph—CCl=CCl—Ph—CF₃
n-C₉H₁₉—Ph—CCl=CCl—Ph—CF₃
CH₃O—Ph—CCl=CCl—Ph—CF₃
n-C₃H₇O—Ph—CCl=CCl—Ph—CF₃
n-C₅H₁₁O—Ph—CCl=CCl—Ph—CF₃
n-C₇H₁₅O—Ph—CCl=CCl—Ph—CF₃
n-C₉H₁₉O—Ph—CCl=CCl—Ph—CF₃ n-C₁₀H₂₁—Ph—CCl=CF—Ph—CF₂CF₃
C₂H₅O—Ph—CCl=CF—Ph—CF₂CF₃
n-C₄H₉O—Ph—CCl=CF—Ph—CF₂CF₃
n-C₆H₁₃O—Ph—CCl=CF—Ph—CF₂CF₃
n-C₈H₁₇O—Ph—CCl=CF—Ph—CF₂CF₃
C₂H₅OCH₂—Ph—CCl=CF—Ph—CF₂CF₃
n-C₄H₉OCH₂—Ph—CCl=CF—Ph—CF₂CF₃
n-C₆H₁₃OCH₂—Ph—CCl=CF—Ph—CF₂CF₃
n-C₈H₁₇OCH₂—Ph—CCl=CF—Ph—CF₂CF₃
C₂H₅—Cy—Ph—CCl=CF—Ph—CF₃
n-C₄H₉—Cy—Ph—CCl=CF—Ph—CF₃
n-C₆H₁₃—Cy—Ph—CCl=CF—Ph—CF₃
C₂H₅O—Cy—Ph—CCl=CF—Ph—CF₃
n-C₄H₉O—Cy—Ph—CCl=CF—Ph—CF₃
n-C₆H₁₃O—Cy—Ph—CCl=CF—Ph—CF₃
C₂H₅OCH₂—Cy—Ph—CCl=CF—Ph—CF₃
n-C₄H₉OCH₂—Cy—Ph—CCl=CF—Ph—CF₃
C₂H₅OCH₂—Ph—CCl=CF—Ph—CH₂CF₃
n-C₄H₉—Cy—Ph—CCl=CF—Ph—CH₂CF₃
n-C₆H₁₃—Cy—Ph—CCl=CF—Ph—CH₂CF₃
C₂H₅—Ph—Ph—CCl=CF—Ph—CF₃
n-C₄H₉—Ph—Ph—CCl=CF—Ph—CF₃
n-C₆H₁₃—Ph—Ph—CCl=CF—Ph—CF₃
C₂H₅O—Ph—Ph—CCl=CF—Ph—CH₂CF₃
n-C₄H₉O—Ph—Ph—CCl=CF—Ph—CH₂CF₃
n-C₆H₁₃O—Ph—Ph—CCl=CF—Ph—CH₂CF₃
C₂H₅—Cy—CH₂CH₂—Ph—CCl=CF—Ph—CF₃
n-C₄H₉—Cy—CH₂CH₂—Ph—CCl=CF—Ph—CF₃
n-C₆H₁₃—Cy—CH₂CH₂—Ph—CCl=CF—Ph—CF₃
C₂H₅O—Cy—CH₂CH₂—Ph—CCl=CF—Ph—CF₃
n-C₄H₉O—Cy—CH₂CH₂—Ph—CCl=CF—Ph—CF₃
n-C₆H₁₃O—Cy—CH₂CH₂—Ph—CCl=CF—Ph—CF₃
C₂H₅—Cy—CH₂CH₂—Ph—CCl=CF—Ph—CH₂CF₃
n-C₄H₉—Cy—CH₂CH₂—Ph—CCl=CF—Ph—CH₂CF₃
n-C₆H₁₃—Cy—CH₂CH₂—Ph—CCl=CF—Ph—CH₂CF₃
C₂H₅O—Cy—CH₂CH₂—Ph—CCl=CF—Ph—CH₂CF₃
n-C₄H₉O—Cy—CH₂CH₂—Ph—CCl=CF—Ph—CH₂CF₃
n-C₆H₁₃O—Cy—CH₂CH₂—Ph—CCl=CF—Ph—CH₂CF₃
C₂H₅—Ph—CCl=CCl—Ph—CF₃
n-C₄H₉—Ph—CCl=CCl—Ph—CF₃
n-C₆H₁₃—Ph—CCl=CCl—Ph—CF₃
n-C₈H₁₇—Ph—CCl=CCl—Ph—CF₃
n-C₁₀H₂₁—Ph—CCl=CCl—Ph—CF₃
C₂H₅O—Ph—CCl=CCl—Ph—CF₃
n-C₄H₉O—Ph—CCl=CCl—Ph—CF₃
n-C₆H₁₃O—Ph—CCl=CCl—Ph—CF₃
n-C₈H₁₇O—Ph—CCl=CCl—Ph—CF₃

-continued

CH₃—Ph—CCl=CCl—Ph—CH₂CF₃
n-C₃H₇—Ph—CCl=CCl—Ph—CH₂CF₃
n-C₅H₁₁—Ph—CCl=CCl—Ph—CH₂CF₃
n-C₇H₁₅—Ph—CCl=CCl—Ph—CH₂CF₃
n-C₉H₁₉—Ph—CCl=CCl—Ph—CH₂CF₃
CH₃O—Ph—CCl=CCl—Ph—CH₂CF₃
n-C₃H₇O—Ph—CCl=CCl—Ph—CH₂CF₃
n-C₅H₁₁O—Ph—CCl=CCl—Ph—CH₂CF₃
CH₃—Ph—CCl=CCl—Ph—CF₂CF₃
n-C₃H₇—Ph—CCl=CCl—Ph—CF₂CF₃
n-C₅H₁₁—Ph—CCl=CCl—Ph—CF₂CF₃
n-C₇H₁₅—Ph—CCl=CCl—Ph—CF₂CF₃
CH₃O—Ph—CCl=CCl—Ph—CF₂CF₃
n-C₃H₇O—Ph—CCl=CCl—Ph—CF₂CF₃
n-C₅H₁₁O—Ph—CCl=CCl—Ph—CF₂CF₃
CH₃—Cy—Ph—CCl=CCl—Ph—CF₃
n-C₃H₇—Cy—Ph—CCl=CCl—Ph—CF₃
n-C₅H₁₁—Cy—Ph—CCl=CCl—Ph—CF₃
n-C₇H₁₅—Cy—Ph—CCl=CCl—Ph—CF₃
CH₃O—Cy—Ph—CCl=CCl—Ph—CF₃
n-C₃H₇O—Cy—Ph—CCl=CCl—Ph—CF₃
n-C₅H₁₁O—Cy—Ph—CCl=CCl—Ph—CF₃
CH₃OCH₂—Cy—Ph—CCl=CCl—Ph—CF₃
n-C₃H₇OCH₂—Cy—Ph—CCl=CCl—Ph—CF₃
n-C₅H₁₁OCH₂—Cy—Ph—CCl=CCl—Ph—CF₃
CH₃—Cy—Ph—CCl=CCl—Ph—CH₂CF₃
n-C₃H₇—Cy—Ph—CCl=CCl—Ph—CH₂CF₃
n-C₅H₁₁—Cy—Ph—CCl=CCl—Ph—CH₂CF₃
CH₃O—Cy—Ph—CCl=CCl—Ph—CH₂CF₃
n-C₃H₇O—Cy—Ph—CCl=CCl—Ph—CH₂CF₃
n-C₅H₁₁O—Cy—Ph—CCl=CCl—Ph—CH₂CF₃
CH₃—Ph—Ph—CCl=CCl—Ph—CF₃
n-C₃H₇—Ph—Ph—CCl=CCl—Ph—CF₃
n-C₅H₁₁—Ph—Ph—CCl=CCl—Ph—CF₃
n-C₇H₁₅—Ph—Ph—CCl=CCl—Ph—CF₃
CH₃O—Ph—Ph—CCl=CCl—Ph—CF₃
n-C₃H₇O—Ph—Ph—CCl=CCl—Ph—CF₃
n-C₅H₁₁O—Ph—Ph—CCl=CCl—Ph—CF₃
CH₃—Ph—Ph—CCl=CCl—Ph—CH₂CF₃
n-C₃H₇—Ph—Ph—CCl=CCl—Ph—CH₂CF₃
n-C₅H₁₁—Ph—Ph—CCl=CCl—Ph—CH₂CF₃
CH₃O—Ph—Ph—CCl=CCl—Ph—CH₂CF₃
n-C₃H₇O—Ph—Ph—CCl=CCl—Ph—CH₂CF₃
n-C₅H₁₁O—Ph—Ph—CCl=CCl—Ph—CH₂CF₃
CH₃—Cy—CH₂CH₂—Ph—CCl=CCl—Ph—CF₃
n-C₃H₇—Cy—CH₂CH₂—Ph—CCl=CCl—Ph—CF₃
n-C₅H₁₁—Cy—CH₂CH₂—Ph—CCl=CCl—Ph—CF₃
n-C₇H₁₅—Cy—CH₂CH₂—Ph—CCl=CCl—Ph—CF,
CH₃O—Cy—CH₂CH₂—Ph—CCl=CCl—Ph—CF₃
n-C₃H₇O—Cy—CH₂CH₂—Ph—CCl=CCl—Ph—CF₃
n-C₅H₁₁O—Cy—CH₂CH₂—Ph—CCl=CCl—Ph—CF₃
CH₃—Ph—CH₂CH₂—Ph—CCl=CCl—Ph—CF₃
n-C₃H₇—Ph—CH₂CH₂—Ph—CCl=CCl—Ph—CF₃
n-C₅H₁₁—Ph—CH₂CH₂—Ph—CCl=CCl—Ph—CF₃
n-C₇H₁₅—Ph—CH₂CH₂—Ph—CCl=CCl—Ph—CF₃
CH₃O—Ph—CH₂CH₂—Ph—CCl=CCl—Ph—CF₃
n-C₃H₇O—Ph—CH₂CH₂—Ph—CCl=CCl—Ph—CF₃
n-C₅H₁₁O—Ph—CH₂CH₂—Ph—CCl=CCl—Ph—CF₃
CH₃—Cy—CH₂CH₂—Ph—CCl=CCl—Ph—CH₂CF₃
n-C₃H₇—Cy—CH₂CH₂—Ph—CCl=CCl—Ph—CH₂CF₃
n-C₅H₁₁—Cy—CH₂CH₂—Ph—CCl=CCl—Ph—CH₂CF₃

C₂H₅—Ph—CCl=CCl—Ph—CH₂CF₃
n-C₄H₉—Ph—CCl=CCl—Ph—CH₂CF₃
n-C₆H₁₃—Ph—CCl=CCl—Ph—CH₂CF₃
n-C₈H₁₇—Ph—CCl=CCl—Ph—CH₂CF₃
n-C₁₀H₂₁—Ph—CCl=CCl—Ph—CH₂CF₃
C₂H₅O—Ph—CCl=CCl—Ph—CH₂CF₃
n-C₄H₉O—Ph—CCl=CCl—Ph—CH₂CF₃
C₂H₅—Ph—CCl=CCl—Ph—CF₂CF₃
n-C₄H₉—Ph—CCl=CCl—Ph—CF₂CF₃
n-C₆H₁₃—Ph—CCl=CCl—Ph—CF₂CF₃
C₂H₅O—Ph—CCl=CCl—Ph—CF₂CF₃
n-C₄H₉O—Ph—CCl=CCl—Ph—CF₂CF₃
C₂H₅—Cy—Ph—CCl=CCl—Ph—CF₃
n-C₄H₉—Cy—Ph—CCl=CCl—Ph—CF₃
n-C₆H₁₃—Cy—Ph—CCl=CCl—Ph—CF₃
C₂H₅O—Cy—Ph—CCl=CCl—Ph—CF₃
n-C₄H₉O—Cy—Ph—CCl=CCl—Ph—CF₃
n-C₆H₁₃O—Cy—Ph—CCl=CCl—Ph—CF₃
C₂H₅OCH₂—Cy—Ph—CCl=CCl—Ph—CF₃
n-C₄H₉OCH₂—Cy—Ph—CCl=CCl—Ph—CF₃
C₂H₅—Cy—Ph—CCl=CCl—Ph—CH₂CF₃
n-C₄H₉—Cy—Ph—CCl=CCl—Ph—CH₂CF₃
n-C₆H₁₃—Cy—Ph—CCl=CCl—Ph—CH,CF₃
C₂H₅O—Cy—Ph—CCl=CCl—Ph—CH₂CF₃
n-C₄H₉O—Cy—Ph—CCl=CCl—Ph—CH₂CF₃
C₂H₅—Ph—Ph—CCl=CCl—Ph—CF₃
n-C₄H₉—Ph—Ph—CCl=CCl—Ph—CF₃
n-C₆H₁₁—Ph—Ph—CCl=CCl—Ph—CF₃
C₂H₅O—Ph—Ph—CCl=CCl—Ph—CF₃
n-C₄H₉O—Ph—Ph—CCl=CCl—Ph—CF₃
n-C₆H₁₃O—Ph—Ph—CCl=CCl—Ph—CF₃
C₂H₅—Ph—Ph—CCl=CCl—Ph—CH₂CF₃
n-C₄H₉—Ph—Ph—CCl=CCl—Ph—CH₂CF₃
n-C₆H₁₃—Ph—Ph—CCl=CCl—Ph—CH₂CF₃
C₂H₅O—Ph—Ph—CCl=CCl—Ph—CH₂CF₃
n-C₄H₉O—Ph—Ph—CCl=CCl—Ph—CH₂CF₃
C₂H₅—Cy—CH₂CH₂—Ph—CCl=CCl—Ph—CF₃
n-C₄H₉—Cy—CH₂CH₂—Ph—CCl=CCl—Ph—CF₃
n-C₆H₁₃—Cy—CH₂CH₂—Ph—CCl=CCl—Ph—CF₃
C₂H₄O—Cy—CH₂CH₂—Ph—CCl=CCl—Ph—CH₂CF₃
n-C₄H₉O—Cy—CH₂CH₂—Ph—CCl=CCl—Ph—CH₂CF₃
C₂H₅—Cy—CH₂CH₂—Ph—CCl=CCl—Ph—CH₂CF₃
n-C₄H₉—Cy—CH₂CH₂—Ph—CCl=CCl—Ph—CH₂CF₃

-continued

C₂H₅O—Cy—CH₂CH₂—Ph—CCl=CCl—Ph—CH₂CF₃
n-C₄H₉O—Cy—CH₂CH₂—Ph—CCl=CCl—Ph—CH₂CF₃

CH₃O—Cy—CH₂CH₂—Ph—CCl=CCl—Ph—CH₂CF₃
n-C₃H₇O—Cy—CH₂CH₂—Ph—CCl=CCl—Ph—CH₂CF₃
n-C₅H₁₁O—Cy—CH₂CH₂—Ph—CCl=CCl—Ph—CH₂CF₃
CH₃—Ph—CCF₃=CCF₃—Ph—CF₃

Trans-4-methyl-α,α',4'-tri-(trifluoromethyl)stilbene

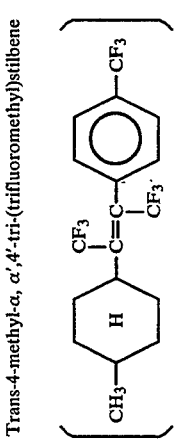

C₂H₅—Ph—CCF₃=CCF₃—Ph—CF₃
n-C₄H₉—Ph—CCF₃=CCF₃—Ph—CF₃
n-C₆H₁₃—Ph—CCF₃=CCF₃—Ph—CF₃
n-C₈H₁₇—Ph—CCF₃=CCF₃—Ph—CF₃
n-C₁₀H₂₁—Ph—CCF₃=CCF₃—Ph—CF₃
CH₃O—Ph—CCF₃=CCF₃—Ph—CF₃
n-C₃H₇O—Ph—CCF₃=CCF₃—Ph—CF₃
n-C₅H₁₁O—Ph—CCF₃=CCF₃—Ph—CF₃
n-C₇H₁₅O—Ph—CCF₃=CCF₃—Ph—CF₃
n-C₉H₁₉O—Ph—CCF₃=CCF₃—Ph—CF₃
CH₃—Ph—CCF₃=CCF₃—Ph—CH₂CF₃
n-C₃H₇—Ph—CCF₃=CCF₃—Ph—CH₂CF₃
n-C₅H₁₁—Ph—CCF₃=CCF₃—Ph—CH₂CF₃
n-C₇H₁₅—Ph—CCF₃=CCF₃—Ph—CH₂CF₃
n-C₉H₁₉—Ph—CCF₃=CCF₃—Ph—CH₂CF₃
CH₃O—Ph—CCF₃=CCF₃—Ph—CH₂CF₃
n-C₃H₇O—Ph—CCF₃=CCF₃—Ph—CH₂CF₃
n-C₅H₁₁O—Ph—CCF₃=CCF₃—Ph—CH₂CF₃
CH₃—Ph—CCF₃=CCF₃—Ph—CF₂CF₃
n-C₃H₇—Ph—CCF₃=CCF₃—Ph—CF₂CF₃
n-C₅H₁₁—Ph—CCF₃=CCF₃—Ph—CF₂CF₃
n-C₇H₁₅—Ph—CCF₃=CCF₃—Ph—CF₂CF₃
CH₃O—Ph—CCF₃=CCF₃—Ph—CF₂CF₃
n-C₃H₇O—Ph—CCF₃=CCF₃—Ph—CF₂CF₃
n-C₅H₁₁O—Ph—CCF₃=CCF₃—Ph—CF₂CF₃
CH₃—Cy—Ph—CCF₃=CCF₃—Ph—CF₃
n-C₃H₇—Cy—Ph—CCF₃=CCF₃—Ph—CF₃
n-C₅H₁₁—Cy—Ph—CCF₃=CCF₃—Ph—CF₃
n-C₇H₁₅—Cy—Ph—CCF₃=CCF₃—Ph—CF₃
CH₃O—Cy—Ph—CCF₃=CCF₃—Ph—CF₃
n-C₃H₇O—Cy—Ph—CCF₃=CCF₃—Ph—CF₃
n-C₅H₁₁O—Cy—Ph—CCF₃=CCF₃—Ph—CF₃
CH₃OCH₂—Cy—Ph—CCF₃=CCF₃—Ph—CF₃
n-C₃H₇OCH₂—Cy—Ph—CCF₃=CCF₃—Ph—CF₃
n-C₅H₁₁OCH₂—Cy—Ph—CCF₃=CCF₃—Ph—CF₃
CH₃—Cy—Ph—CCF₃=CCF₃—Ph—CH₂CF₃
n-C₃H₇—Cy—Ph—CCF₃=CCF₃—Ph—CH₂CF₃
n-C₅H₁₁—Cy—Ph—CCF₃=CCF₃—Ph—CH₂CF₃
CH₃O—Cy—Ph—CCF₃=CCF₃—Ph—CH₂CF₃
n-C₃H₇O—Cy—Ph—CCF₃=CCF₃—Ph—CH₂CF₃
n-C₅H₁₁O—Cy—Ph—CCF₃=CCF₃—Ph—CH₂CF₃
CH₃—Ph—Ph—CCF₃=CCF₃—Ph—CF₃
n-C₃H₇—Ph—Ph—CCF₃=CCF₃—Ph—CF₃
n-C₅H₁₁—Ph—Ph—CCF₃=CCF₃—Ph—CF₃
CH₃O—Ph—Ph—CCF₃=CCF₃—Ph—CF₃ n-C₃H₇—Ph—CCF₃=CCF₃—Ph—CF₃
n-C₅H₁₁—Ph—CCF₃=CCF₃—Ph—CF₃
n-C₇H₁₅—Ph—CCF₃=CCF₃—Ph—CF₃
n-C₉H₁₉—Ph—CCF₃=CCF₃—Ph—CF₃

C₂H₅O—Ph—CCF₃=CCF₃—Ph—CF₃
n-C₄H₉O—Ph—CCF₃=CCF₃—Ph—CF₃
n-C₆H₁₃O—Ph—CCF₃=CCF₃—Ph—CF₃
n-C₈H₁₇O—Ph—CCF₃=CCF₃—Ph—CF₃

C₂H₅—Ph—CCF₃=CCF₃—Ph—CH₂CF₃
n-C₄H₉—Ph—CCF₃=CCF₃—Ph—CH₂CF₃
n-C₆H₁₃—Ph—CCF₃=CCF₃—Ph—CH₂CF₃
n-C₈H₁₇—Ph—CCF₃=CCF₃—Ph—CH₂CF₃
n-C₁₀H₂₁—Ph—CCF₃=CCF₃—Ph—CH₂CF₃
C₂H₅O—Ph—CCF₃=CCF₃—Ph—CH₂CF₃
n-C₄H₉O—Ph—CCF—₃=CCF₃—Ph—CH₂CF₃

C₂H₅—Ph—CCF₃=CCF₃—Ph—CF₂CF₃
n-C₄H₉—Ph—CCF₃=CCF₃—Ph—CF₂CF₃
n-C₆H₁₃—Ph—CCF₃=CCF₃—Ph—CF₂CF₃

C₂H₅O—Ph—CCF₃=CCF₃—Ph—CF₂CF₃
n-C₄H₉O—Ph—CCF₃=CCF₃—Ph—CF₂CF₃

C₂H₅—Cy—Ph—CCF₃=CCF₃—Ph—CF₃
n-C₄H₉—Cy—Ph—CCF₃=CCF₃—Ph—CF₃
n-C₆H₁₃—Cy—Ph—CCF₃=CCF₃—Ph—CF₃

C₂H₅O—Cy—Ph—CCF₃=CCF₃—Ph—CF₃
n-C₄H₉O—Cy—Ph—CCF₃=CCF₃—Ph—CF₃
n-C₆H₁₃O—Cy—Ph—CCF₃=CCF₃—Ph—CF₃
C₂H₅OCH₂—Cy—Ph—CCF₃=CCF₃—Ph—CF₃
n-C₄H₉OCH₂—Cy—Ph—CCF₃=CCF₃—Ph—CF₃

C₂H₅—Cy—Ph—CCF₃=CCF₃—Ph—CH₂CF₃
n-C₄H₉—Cy—Ph—CCF₃=CCF₃—Ph—CH₂CF₃

C₂H₅O—Cy—Ph—CCF₃=CCF₃—Ph—CH₂CF₃
n-C₄H₉O—Cy—Ph—CCF₃=CCF₃—Ph—CH₂CF₃

C₂H₅—Ph—Ph—CCF₃=CCF₃—Ph—CF₃
n-C₄H₉—Ph—Ph—CCF₃=CCF₃—Ph—CF₃
n-C₆H₁₃—Ph—Ph—CCF₃=CCF₃—Ph—CF₃
C₂H₅O—Ph—Ph—CCF₃=CCF₃—Ph—CF₃

-continued n-C4H9O—Ph—Ph—CCF3=CCF3—Ph—CF3

C2H5—Ph—Ph—CCF3=CCF3—Ph—CF3
n-C4H9—Ph—Ph—CCF3=CCF3—Ph—CH2CF3
n-C6H13—Ph—Ph—CCF3=CCF3—Ph—CH2CF3
n-C5H11—Ph—Ph—CCF3=CCF3—Ph—CH2CF3
C2H5O—Ph—Ph—CCF3=CCF3—Ph—CH2CF3
n-C4H9O—Ph—Ph—CCF3=CCF3—Ph—CH2CF3

C2H5—Cy—CH2CH2—Ph—CCF3=CCF3—Ph—CF3
n-C4H9—Cy—CH2CH2—Ph—CCF3=CCF3—Ph—CF3
n-C6H13—Cy—CH2CH2—Ph—CCF3=CCF3—Ph—CF3

C2H5O—Cy—CH2CH2—Ph—CCF3=CCF3—Ph—CF3
n-C4H9O—Cy—CH2CH2—Ph—CCF3=CCF3—Ph—CF3

C2H5—Cy—CH2CH2—Ph—CCF3=CCF3—Ph—CH2CF3 n-C3H7—Cy—CH2CH2—Ph—CCF3=CCF3—Ph—CF3
n-C5H11—Cy—CH2CH2—Ph—CCF3=CCF3—Ph—CF3
n-C7H15—Cy—CH2CH2—Ph—CCF3=CCF3—Ph—CF3
C2H5O—Cy—CH2CH2—Ph—CCF3=CCF3—Ph—CF3

C2H5—Ph—CCF3=CF—Ph—CF3
n-C4H9—Ph—CCF3=CF—Ph—CF3
n-C6H13—Ph—CCF3=CF—Ph—CF3
n-C5H17—Ph—CCF3=CF—Ph—CF3
n-C10H21—Ph—CCF3=CF—Ph—CF3
CH3O—Ph—CCF3=CF—Ph—CF3
C2H5O—Ph—CCF3=CF—Ph—CF3
n-C4H9O—Ph—CCF3=CF—Ph—CF3
n-C6H13O—Ph—CCF3=CF—Ph—CF3
n-C5H17O—Ph—CCF3=CF—Ph—CF3

C2H5—Ph—CCF3=CF—Ph—CH2CF3
n-C4H9—Ph—CCF3=CF—Ph—CH2CF3 n-C3H7O—Ph—Ph—Ph—CCF3=CCF3—Ph—CF3
n-C5H11O—Ph—Ph—Ph—CCF3=CCF3—Ph—CF3
CH3—Ph—Ph—Ph—CCF3=CCF3—Ph—CH2CF3
n-C3H7—Ph—Ph—Ph—CCF3=CCF3—Ph—CH2CF3
n-C5H11—Ph—Ph—Ph—CCF3=CCF3—Ph—CH2CF3
CH3O—Ph—Ph—Ph—CCF3=CCF3—Ph—CH2CF3
n-C3H7O—Ph—Ph—Ph—CCF3=CCF3—Ph—CH2CF3
n-C5H11O—Ph—Ph—Ph—CCF3=CCF3—Ph—CH2CF3
CH3—Cy—CH2CH2—Ph—CCF3=CCF3—Ph—CF3
n-C3H7—Cy—CH2CH2—Ph—CCF3=CCF3—Ph—CF3
n-C5H11—Cy—CH2CH2—Ph—CCF3=CCF3—Ph—CF3
n-C7H15—Cy—CH2CH2—Ph—CCF3=CCF3—Ph—CF3
CH3O—Cy—CH2CH2—Ph—CCF3=CCF3—Ph—CF3
n-C3H7O—Cy—CH2CH2—Ph—CCF3=CCF3—Ph—CF3
n-C5H11O—Cy—CH2CH2—Ph—CCF3=CCF3—Ph—CF3
CH3—Cy—CH2CH2—Ph—CCF3=CCF3—Ph—CH2CF3
n-C3H7—Cy—CH2CH2—Ph—CCF3=CCF3—Ph—CH2CF3
C2H5—Cy—CH2CH2—Ph—CCF3=CCF3—Ph—CH2CF3
n-C4H9—Cy—CH2CH2—Ph—CCF3=CCF3—Ph—CH2CF3
n-C6H13—Cy—CH2CH2—Ph—CCF3=CCF3—Ph—CH2CF3
CH3O—Cy—CH2CH2—Ph—CCF3=CCF3—Ph—CH2CF3
n-C3H7O—Cy—CH2CH2—Ph—CCF3=CCF3—Ph—CH2CF3
n-C4H9O—Cy—CH2CH2—Ph—CCF3=CCF3—Ph—CH2CF3
CH3—Cy—CH2CH2—Ph—CCF3=CCF3—Ph—CH2CF3
C2H5—Cy—CH2CH2—Ph—CCF3=CCF3—Ph—CH2CF3
n-C3H7—Cy—CH2CH2—Ph—CCF3=CCF3—Ph—CH2CF3
n-C5H11—Cy—CH2CH2—Ph—CCF3=CCF3—Ph—CH2CF3
CH3O—Cy—CH2CH2—Ph—CCF3=CCF3—Ph—CH2CF3
C2H5O—Cy—CH2CH2—Ph—CCF3=CCF3—Ph—CH2CF3
n-C3H7O—Cy—CH2CH2—Ph—CCF3=CCF3—Ph—CH2CF3
n-C4H9O—Cy—CH2CH2—Ph—CCF3=CCF3—Ph—CH2CF3
n-C5H11O—Cy—CH2CH2—Ph—CCF3=CCF3—Ph—CH2CF3
CH3—Ph—CCF3=CF—Ph—CF3
n-C3H7—Ph—CCF3=CF—Ph—CF3
n-C5H11—Ph—CCF3=CF—Ph—CF3
n-C7H15—Ph—CCF3=CF—Ph—CF3
n-C9H19—Ph—CCF3=CF—Ph—CF3
n-C10H21—Ph—CCF3=CF—Ph—CF3
CH3O—Ph—CCF3=CF—Ph—CF3
n-C3H7O—Ph—CCF3=CF—Ph—CF3
n-C5H11O—Ph—CCF3=CF—Ph—CF3
n-C7H15O—Ph—CCF3=CF—Ph—CF3
n-C9H19O—Ph—CCF3=CF—Ph—CF3
CH3—Ph—CCF3=CF—Ph—CH2CF3
n-C3H7—Ph—CCF3=CF—Ph—CH2CF3

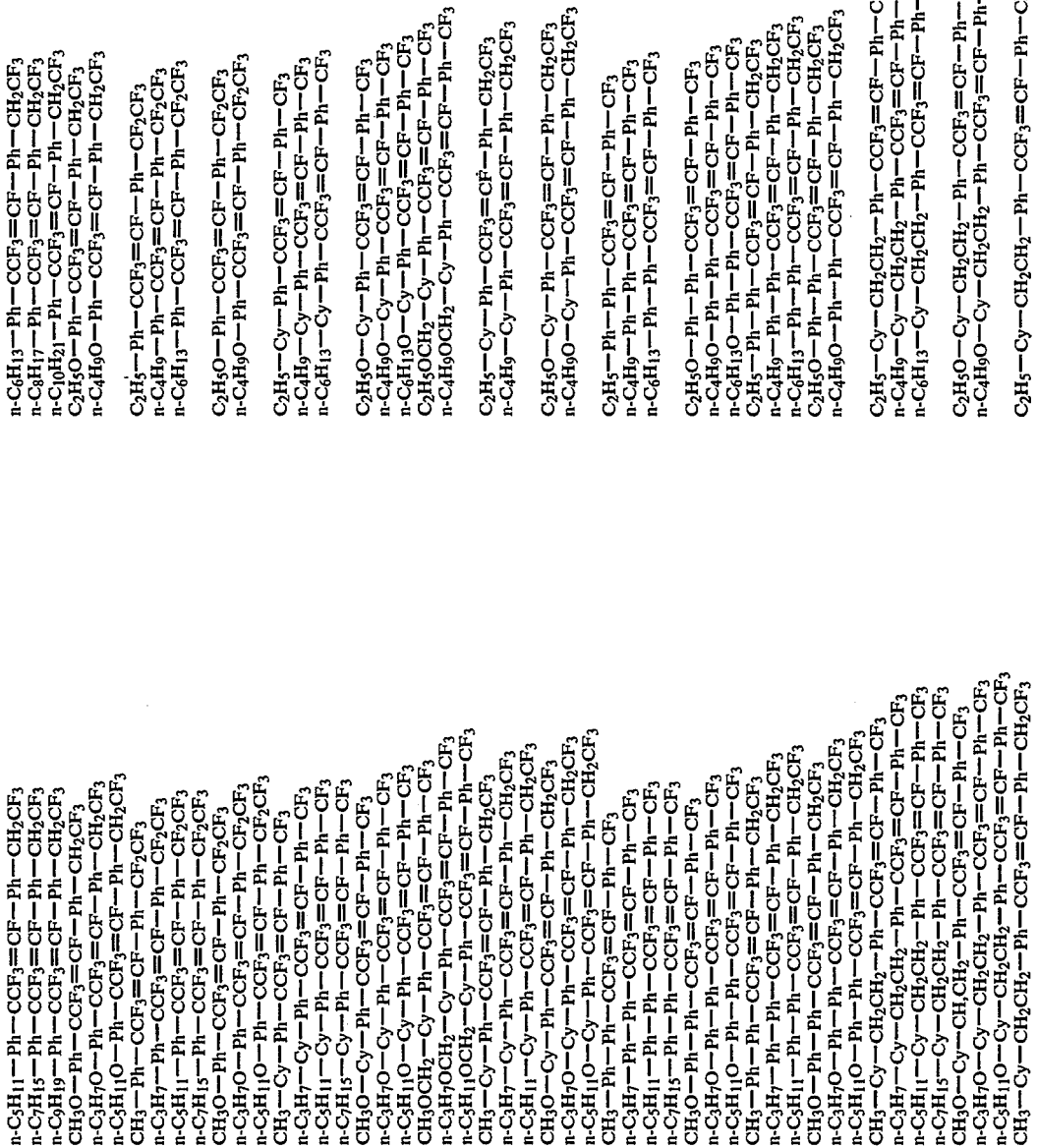

n-C₃H₇—Cy—CH₂CH₂—Ph—CCF₃=CF—Ph—CH₂CF₃
n-C₅H₁₁—Cy—CH₂CH₂—Ph—CCF₃=CF—Ph—CH₂CF₃
CH₃O—Cy—CH₂CH₂—Ph—CCF₃=CF—Ph—CH₂CF₃
n-C₃H₇O—Cy—CH₂CH₂—Ph—CCF₃=CF—Ph—CH₂CF₃
n-C₅H₁₁O—Cy—CH₂CH₂—Ph—CCF₃=CF—Ph—Cn₂CF₃
CH₃—Ph—CF=CCF₃—Ph—CF₃
n-C₃H₇—Ph—CF=CCF₃—Ph—CF₃
n-C₅H₁₁—Ph—CF=CCF₃—Ph—CF₃
n-C₇H₁₅—Ph—CF=CCF₃—Ph—CF₃
n-C₉H₁₉—Ph—CF=CCF₃—Ph—CF₃
CH₃O—Ph—CF=CCF₃—Ph—CF₃
n-C₃H₇O—Ph—CF=CCF₃—Ph—CF₃
n-C₅H₁₁O—Ph—CF=CCF₃—Ph—CF₃
n-C₇H₁₅O—Ph—CF=CCF₃—Ph—CF₃
n-C₉H₁₉O—Ph—CF=CCF₃—Ph—CF₃
CH₃—Ph—CF=CCF₃—Ph—CH₂CF₃
n-C₃H₇—Ph—CF=CCF₃—Ph—CH₂CF₃
n-C₅H₁₁—Ph—CF=CCF₃—Ph—CH₂CF₃
n-C₇H₁₅—Ph—CF=CCF₃—Ph—CH₂CF₃
n-C₉H₁₉—Ph—CF=CCF₃—Ph—CH₂CF₃
CH₃O—Ph—CF=CCF₃—Ph—CH₂CF₃
n-C₃H₇O—Ph—CF=CCF₃—Ph—CH₂CF₃
n-C₅H₁₁O—Ph—CF=CCF₃—Ph—CH₂CF₃
CH₃—Ph—CF=CCF₃—Ph—CF₂CF₃
n-C₃H₇—Ph—CF=CCF₃—Ph—CF₂CF₃
n-C₅H₁₁—Ph—CF=CCF₃—Ph—CF₂CF₃
n-C₇H₁₅—Ph—CF=CCF₃—Ph—CF₂CF₃
CH₃O—Ph—CF=CCF₃—Ph—CF₂CF₃
n-C₃H₇O—Ph—CF=CCF₃—Ph—CF₂CF₃
n-C₅H₁₁O—Ph—CF=CCF₃—Ph—CF₂CF₃
CH₃—Cy—Ph—CF=CCF₃—Ph—CF₃
n-C₃H₇—Cy—Ph—CF=CCF₃—Ph—CF₃
n-C₅H₁₁—Cy—Ph—CF=CCF₃—Ph—CF₃
n-C₇H₁₅—Cy—Ph—CF=CCF₃—Ph—CF₃
CH₃O—Cy—Ph—CF=CCF₃—Ph—CF₃ n-C₄H₉—Cy—CH₂CH₂—Ph—CCF₃=CF—Ph—CH₂CF₃
C₂H₅O—Cy—CH₂CH₂—Ph—CCF₃=CF—Ph—CH₂CF₃
n-C₄H₉O—Cy—CH₂CH₂—Ph—CCF₃=CF—Ph—CH₂CF₃
C₂H₅—Ph—CF=CCF₃—Ph—CF₃
n-C₄H₉—Ph—CF=CCF₃—Ph—CF₃
n-C₆H₁₃—Ph—CF=CCF₃—Ph—CF₃
n-C₈H₁₇—Ph—CF=CCF₃—Ph—CF₃
n-C₁₀H₂₁—Ph—CF=CCF₃—Ph—CF₃
C₂H₅O—Ph—CF=CCF₃—Ph—CF₃
n-C₄H₉O—Ph—CF=CCF₃—Ph—CF₃
n-C₆H₁₃O—Ph—CF=CCF₃—Ph—CF₃
n-C₈H₁₇O—Ph—CF=CCF₃—Ph—CF₃
C₂H₅—Ph—CF=CCF₃—Ph—CH₂CF₃
n-C₄H₉—Ph—CF=CCF₃—Ph—CH₂CF₃
n-C₆H₁₃—Ph—CF=CCF₃—Ph—CH₂CF₃
n-C₈H₁₇—Ph—CF=CCF₃—Ph—CH₂CF₃
n-C₁₀H₂₁—Ph—CF=CCF₃—Ph—CH₂CF₃
C₂H₅O—Ph—CF=CCF₃—Ph—CH₂CF₃
n-C₄H₉O—Ph—CF=CCF₃—Ph—CH₂CF₃
C₂H₅—Ph—CF=CCF₃—Ph—CF₂CF₃
n-C₄H₉—Ph—CF=CCF₃—Ph—CF₂CF₃
n-C₆H₁₃—Ph—CF=CCF₃—Ph—CF₂CF₃
C₂H₅O—Ph—CF=CCF₃—Ph—CF₂CF₃
n-C₄H₉O—Ph—CF=CCF₃—Ph—CF₂CF₃
C₂H₅—Cy—Ph—CF=CCF₃—Ph—CF₃
n-C₄H₉—Cy—Ph—CF=CCF₃—Ph—CF₃
n-C₆H₁₃—Cy—Ph—CF=CCF₃—Ph—CF₃
C₂H₅O—Cy—Ph—CF=CCF₃—Ph—CF₃

In the same manner, the following compounds can be prepared.

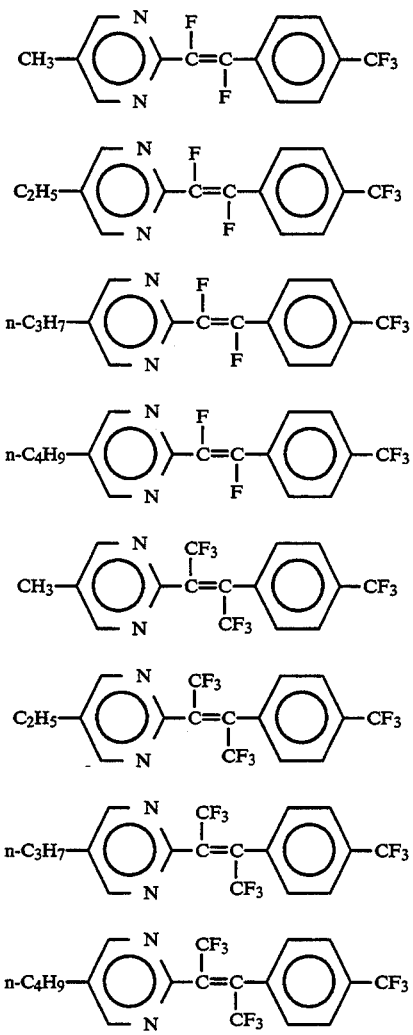

EXAMPLE 5

The anisotropy of refractive index (Δn) of a liquid crystal composition of Merck Co. "ZLI-1565" was 0.1245. When 5 wt % of the compound of Example 1 was added to 95 wt % of this liquid crystal composition, the anisotropy of refractive index (Δn) of the liquid crystal composition became 0.1371.

Each of such liquid crystal compositions was injected into a cell prepared by combining ITO transparent electrodes coated with polyimide and subjected to rubbing treatment and having a space of 8 μm between the substrates, and the cell was operated by multiplex drive at 25° C. to measure the response speed. The liquid crystal device using the liquid crystal composition of the present invention showed a response speed quicker by about 20% than the liquid crystal device using the conventional composition.

EXAMPLE 6

The anisotropy of refractive index (Δn) of a liquid crystal composition prepared by adding 2.5 wt % of the compound of Example 4 to 97.5 wt % of the liquid crystal composition of Merck Co. "ZLI-1565" was 0.1279. Each of the liquid crystal compositions was injected into a cell prepared by combining ITO transparent electrodes coated with polyimide and subjected to rubbing treatment and having a space of 8 μm between the substrates, and the cell was operated by multiplex drive at 25° C. to measure the response speed. The liquid crystal device using the liquid crystal composition of the present invention showed a response speed quicker by about 10% than the liquid crystal device using the conventional composition.

As described in the foregoing, the present invention provides trans-dihalogenostilbene compounds of the formula:

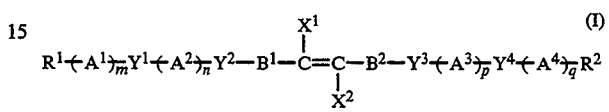

particularly trans-dihalogenostilbene compounds of the formula:

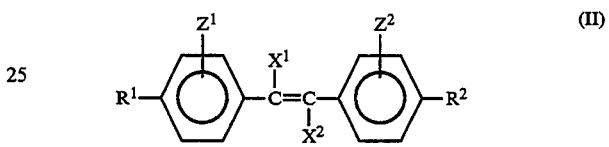

as novel compounds, and a liquid crystal composition containing at least one of such compounds and a liquid crystal electro-optical display device having such a liquid crystal composition interposed between a pair of substrates provided with electrodes, whereby it is possible to increase the anisotropy of refractive index (Δn) and to obtain a liquid crystal device having a high response speed.

What is claimed is:

1. A liquid crystal composition containing at least one trans-dihalogenostilbene compound of the formula:

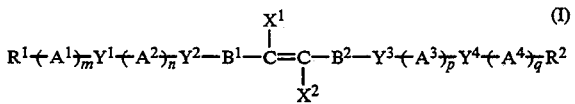

wherein each of $A^1$ to $A^4$, which are independent from one another, is a trans-1,4-cyclohexylene group or a 1,4-phenylene group, which is unsubstituted or substituted by one or more halogen atoms, methyl groups or nitrile groups and in which one or more CH groups may be substituted by nitrogen atoms, and one or more $CH_2$ groups may be substituted by oxygen atoms or sulfur atoms; each of $B^1$ and $B^2$, which are independent from each other, is a 1,4-phenylene group, which is unsubstituted or substituted by one or more halogen atoms, methyl groups or nitrile groups and in which one or more CH groups may be substituted by nitrogen atoms; each of $Y^1$ to $Y^4$, which are independent from one another, is —COO—, —O—, —OCO—, —CH$_2$CH$_2$—, —CH$_2$—, —CH=CH—, —OCH$_2$—, —CH$_2$O—, —CH=N—, —NO=N—, —N=ON—, —C≡C—, —N=N— or a single bond; each of $X^1$ and $X^2$ are fluorine atoms; each of m, n, p and q is 0 or 1; and each of $R^1$ and $R^2$, which are independent from each other, is a $C_1$-$C_{10}$ alkyl group, a halogen atom, a nitrile group or an isothiacyanate group, provided that in the case of the alkyl group, an oxygen atom may be interposed in a carbon-carbon bond of the group or in a carbon-carbon bond between this group and the adjacent ring, and in a case where $R^1$ or $R^2$ is the alkyl group, some of hydrogen atoms in the group may be substituted by fluorine atoms.

2. The liquid crystal composition according to claim 1, wherein the compound of the formula (I) is represented by the formula:

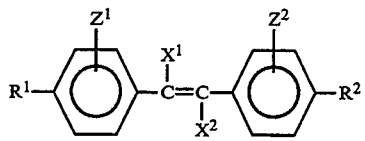

(II)

wherein each of $Z^1$ and $Z^2$, which are independent from each other, is a fluorine atom, a chlorine atom or a hydrogen atom.

3. The liquid crystal composition according to claim 1, which contains cholesteric liquid crystal or a chiral compound capable of imparting natural twist to liquid crystal.

4. A liquid crystal electro-optical device having the liquid crystal composition of claim 1 interposed between a pair of substrates provided with electrodes.

5. The liquid crystal electro-optical device according to claim 4, wherein the substrates provided with electrodes are coated with a polyimide and have rubbing treatment applied thereto.

6. The liquid crystal electro-optical device according to claim 4, which is a liquid display device adapted for multiplex drive.

7. The liquid display device according to claim 6, wherein the liquid composition used is a liquid crystal composition containing a chiral compound or cholesteric liquid crystal, and the electrodes on the pair of substrates or the coating layers on the electrodes are treated by rubbing treatment so that liquid crystal molecules are twisted to an angle of from 180° to 360°.

8. The liquid crystal composition according to claim 1, wherein the compound of the formula (I) is represented by the formula:

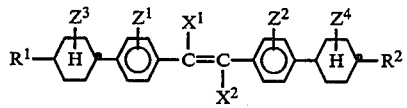

(III)

wherein each of $Z^1$, $Z^2$, $Z^3$ and $Z^4$, which are independent from one another, is a fluorine atom, a chlorine atom or a hydrogen atom.

9. The liquid crystal composition according to claim 1, wherein the compound of the formula (I) is represented by the formula:

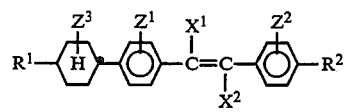

(IV)

wherein each of $Z^1$, $Z^2$ and $Z^3$, which are independent from one another, is a fluorine atom, a chlorine atom or a hydrogen atom.

10. The liquid crystal composition according to claim 1, wherein the compound of the formula (I) is represented by the formula:

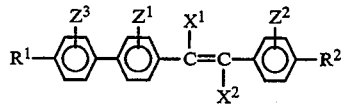

(V)

wherein each of $Z^1$, $Z^2$ and $Z^3$, which are independent from one another, is a fluorine atom, a chlorine atom or a hydrogen atom.

11. The liquid crystal composition according to claim 1, wherein the compound of the formula (I) is represented by the formula:

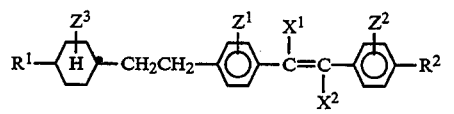

(VI)

wherein each of $Z^1$, $Z^2$ and $Z^3$, which are independent from one another, is a fluorine atom, a chlorine atom or a hydrogen atom.

12. The liquid crystal composition according to claim 1, wherein each of $A^1$ to $A^4$, which are independent from one another, is a 1,4-phenylene group which is unsubstituted or substituted by one or more halogen atoms, methyl groups or nitrile groups and in which one or more CH groups may be substituted by nitrogen atoms;
   wherein each of $R^1$ and $R^2$ is a $C_1$-$C_{10}$-alkyl group, wherein an oxygen atom may be interposed in a carbon-carbon bond of the group or in a carbon-carbon bond between this group and the adjacent phenylene ring.

13. The liquid crystal composition according to claim 12, wherein the alkyl group is a linear alkyl group.

14. The liquid crystal composition according to claim 12, wherein some of hydrogen atoms of the alkyl group are substituted by fluorine atoms.

15. The liquid crystal composition according to claim 14, wherein the alkyl group is a linear alkyl group.

16. The liquid crystal composition according to claim 2, wherein each of $Z^1$ and $Z^2$ is a hydrogen atom.

17. The liquid crystal composition according to claim 1, wherein either $Z^1$ or $Z^2$ is a fluorine atom, a chlorine atom or a bromine atom.

18. The liquid crystal composition according to claim 2, wherein at least one of $R^1$ and $R^2$ is a $C_1$-$C_{10}$-alkyl group, wherein an oxygen atom may be interposed in a carbon-carbon bond of the group or in a carbon-carbon bond between this group and the adjacent phenylene ring.

* * * * *